United States Patent [19]
Trofatter et al.

[11] Patent Number: 6,077,685
[45] Date of Patent: Jun. 20, 2000

[54] TUMOR SUPPRESSOR MERLIN AND ANTIBODIES THEREOF

[75] Inventors: James A. Trofatter, Charlestown; Mia M. MacCollin, Medford; James F. Gusella, Framingham, all of Mass.

[73] Assignee: The General Hospital Corporation, Boston, Mass.

[21] Appl. No.: 08/478,087

[22] Filed: Jun. 7, 1995

Related U.S. Application Data

[60] Division of application No. 08/171,718, Dec. 22, 1993, which is a continuation-in-part of application No. 08/108,808, Aug. 19, 1993, abandoned, which is a continuation-in-part of application No. 08/026,063, Mar. 4, 1993, abandoned, which is a continuation-in-part of application No. 08/022,034, Feb. 25, 1993, abandoned.

[51] Int. Cl.[7] .......................... C07K 14/82; C07K 16/30; C12N 15/12; A61K 48/00
[52] U.S. Cl. ................. 435/69.1; 435/172.1; 435/320.1; 514/12; 935/62; 530/350; 530/387.1; 530/387.3; 530/387.7
[58] Field of Search ................................. 530/350, 387.1, 530/387.3, 387.7; 435/69.1, 172.1, 320.1; 514/12; 935/62

[56] References Cited

U.S. PATENT DOCUMENTS 5,578,462  11/1996  Seizinger et al. ...................... 435/69.1

FOREIGN PATENT DOCUMENTS

WO 90/09441  8/1990  WIPO .
WO 93/03743  3/1993  WIPO .

*Primary Examiner*—Lila Feisee
*Assistant Examiner*—John Lucas
*Attorney, Agent, or Firm*—Sterne, Kessler, Goldstein & Fox P.L.L.C.

[57] ABSTRACT

A novel tumor suppressor protein, merlin, is described, including DNA sequences encoding merlin, and recombinant vectors and hosts capable of expressing merlin. Method for the diagnosis and treatment of merlin-associated tumors, and for the diagnosis and treatment of the disease neurofibromatosis 2 (NF2) are also provided.

16 Claims, 28 Drawing Sheets

```
ACGGCAGCCG TCAGGGACCG TCCCCCAACT CCCCTTTCCG CTCAGGCAGG GTCCTCGCGG      60

CCCATGCTGG CCGCTGGGGA CCCGCGCAGC CCAGACCGTT CCCGGGCCGG CCAGCCGGCA     120

CCATGGTGGC CCTGAGGCCT GTGCAGCAAC TCCAGGGGGG CTAAAGGGCT CAGAGTGCAG     180

GCCGTGGGGC GCGAGGGTCC CGGGCCTGAG CCCCGCGCC ATG GCC GGG GCC ATC        234
                                           Met Ala Gly Ala Ile
                                             1               5

GCT TCC CGC ATG AGC TTC AGC TCT CTC AAG AGG AAG CAA CCC AAG ACG       282
Ala Ser Arg Met Ser Phe Ser Ser Leu Lys Arg Lys Gln Pro Lys Thr
              10                  15                  20

TTC ACC GTG AGG ATC GTC ACC ATG GAC GCC GAG ATG GAG TTC AAT TGC       330
Phe Thr Val Arg Ile Val Thr Met Asp Ala Glu Met Glu Phe Asn Cys
              25                  30                  35

GAG ATG AAG TGG AAA GGG AAG GAC CTC TTT GAT TTG GTG TGC CGG ACT       378
Glu Met Lys Trp Lys Gly Lys Asp Leu Phe Asp Leu Val Cys Arg Thr
              40                  45                  50

CTG GGG CTC CGA GAA ACC TGG TTC TTT GGA CTG CAG TAC ACA ATC AAG       426
Leu Gly Leu Arg Glu Thr Trp Phe Phe Gly Leu Gln Tyr Thr Ile Lys
          55                  60                  65

GAC ACA GTG GCC TGG CTC AAA ATG GAC AAG AAG GTA CTG GAT CAT GAT       474
Asp Thr Val Ala Trp Leu Lys Met Asp Lys Lys Val Leu Asp His Asp
          70                  75                  80              85
```

FIG.3A

```
GTT TCA AAG GAA GAA CCA GTC ACC TTT CAC TTC TTG GCC AAA TTT TAT          522
Val Ser Lys Glu Glu Pro Val Thr Phe His Phe Leu Ala Lys Phe Tyr
            90                  95                 100

CCT GAG AAT GCT GAA GAG GAG CTG GTT CAG GAG ATC ACA CAA CAT TTA          570
Pro Glu Asn Ala Glu Glu Glu Leu Val Gln Glu Ile Thr Gln His Leu
            105                 110                115

TTC TTC TTA CAG GTA AAG AAG CAG ATT TTA GAT GAA AAG ATC TAC TGC          618
Phe Phe Leu Gln Val Lys Lys Gln Ile Leu Asp Glu Lys Ile Tyr Cys
            120                 125                130

CCT CCT GAG GCT TCT GTG CTC CTG GCT TCT TAC GCC GTC CAG GCC AAG          666
Pro Pro Glu Ala Ser Val Leu Leu Ala Ser Tyr Ala Val Gln Ala Lys
            135                 140                145

TAT GGT GAC TAC GAC CCC AGT GTT CAC AAG CGG GGA TTT TTG GCC CAA          714
Tyr Gly Asp Tyr Asp Pro Ser Val His Lys Arg Gly Phe Leu Ala Gln
150                 155                 160                165

GAG GAA TTG CTT CCA AAA AGG GTA ATA AAT CTG TAT CAG ATG ACT CCG          762
Glu Glu Leu Leu Pro Lys Arg Val Ile Asn Leu Tyr Gln Met Thr Pro
            170                 175                180

GAA ATG TGG GAG GAG AGA ATT ACT GCT TGG TAC GCA GAG CAC CGA GGC          810
Glu Met Trp Glu Glu Arg Ile Thr Ala Trp Tyr Ala Glu His Arg Gly
            185                 190                195

CGA GCC AGG GAT GAA GCT GAA ATG GAA TAT CTG AAG ATA GCT CAG GAC          858
Arg Ala Arg Asp Glu Ala Glu Met Glu Tyr Leu Lys Ile Ala Gln Asp
```

FIG.3B

```
                    200                      205                        210
CTG GAG ATG TAC GGT GTG AAC TAC TTT GCA ATC CGG AAT AAA AAG GGC                906
Leu Glu Met Tyr Gly Val Asn Tyr Phe Ala Ile Arg Asn Lys Lys Gly
        215                      220                      225

ACA GAG CTG CTG CTT GGA GTG GAT GCC CTG GGG CTT CAC ATT TAT GAC                954
Thr Glu Leu Leu Leu Gly Val Asp Ala Leu Gly Leu His Ile Tyr Asp
230                      235                      240                 245

CCT GAG AAC AGA CTG ACC CCC AAG ATC TCC TTC CCG TGG AAT GAA ATC                1002
Pro Glu Asn Arg Leu Thr Pro Lys Ile Ser Phe Pro Trp Asn Glu Ile
                    250                      255                 260

CGA AAC ATC TCG TAC AGT GAC AAG GAG TTT ACT ATT AAA CCA CTG GAT                1050
Arg Asn Ile Ser Tyr Ser Asp Lys Glu Phe Thr Ile Lys Pro Leu Asp
                265                      270                      275

AAG AAA ATT GAT GTC TTC AAG TTT AAC TCC TCA AAG CTT CGT GTT AAT                1098
Lys Lys Ile Asp Val Phe Lys Phe Asn Ser Ser Lys Leu Arg Val Asn
            280                      285                      290

AAG CTG ATT CTC CAG CTA TGT ATC GGG AAC CAT GAT CTA TTT ATG AGG                1146
Lys Leu Ile Leu Gln Leu Cys Ile Gly Asn His Asp Leu Phe Met Arg
        295                      300                      305

AGA AGG AAA GCC GAT TCT TTG GAA GTT CAG CAG ATG AAA GCC CAG GCC                1194
Arg Arg Lys Ala Asp Ser Leu Glu Val Gln Gln Met Lys Ala Gln Ala
310                      315                      320                 325

AGG GAG GAG AAG GCT AGA AAG CAG ATG GAG CGG CAG CGC CTC GCT CGA                1242
Arg Glu Glu Lys Ala Arg Lys Gln Met Glu Arg Gln Arg Leu Ala Arg
```

FIG.3C

```
                    330                   335                      340
GAG AAG CAG ATG AGG GAG GAG GCT GAA CGC ACG AGG GAT GAG TTG GAG          1290
Glu Lys Gln Met Arg Glu Glu Ala Glu Arg Thr Arg Asp Glu Leu Glu
            345                 350                 355

AGG AGG CTG CTG CAG ATG AAA GAA GAA GCA ACA ATG GCC AAC GAA GCA          1338
Arg Arg Leu Leu Gln Met Lys Glu Glu Ala Thr Met Ala Asn Glu Ala
            360                 365                 370

CTG ATG CGG TCT GAG GAG ACA GCT GAC CTG TTG GCT GAA AAG GCC CAG          1386
Leu Met Arg Ser Glu Glu Thr Ala Asp Leu Leu Ala Glu Lys Ala Gln
            375                 380                 385

ATC ACC GAG GAG GAG GCA AAA CTT CTG GCC CAG AAG GCC GCA GAG GCT          1434
Ile Thr Glu Glu Glu Ala Lys Leu Leu Ala Gln Lys Ala Ala Glu Ala
390                 395                 400                 405

GAG CAG GAA ATG CAG CGC ATC AAG GCC ACA GCG ATT CGC ACG GAG GAG          1482
Glu Gln Glu Met Gln Arg Ile Lys Ala Thr Ala Ile Arg Thr Glu Glu
            410                 415                 420

GAG AAG CGC CTG ATG GAG CAG AAG GTG CTG GAA GCC GAG GTG CTG GCA          1530
Glu Lys Arg Leu Met Glu Gln Lys Val Leu Glu Ala Glu Val Leu Ala
            425                 430                 435

CTG AAG ATG GCT GAG GAG TCA GAG AGG AGG GCC AAA GAG GCA GAT CAG          1578
Leu Lys Met Ala Glu Glu Ser Glu Arg Arg Ala Lys Glu Ala Asp Gln
            440                 445                 450

CTG AAG CAG GAC CTG CAG GAA GCA CGC GAG GCG GAG CGA AGA GCC AAG          1626
Leu Lys Gln Asp Leu Gln Glu Ala Arg Glu Ala Glu Arg Arg Ala Lys
```

CAG AAG CTC CTG GAG ATT GCC ACC AAG CCC ACG TAC CCG CCC ATG AAC         1674
Gln Lys Leu Leu Glu Ile Ala Thr Lys Pro Thr Tyr Pro Pro Met Asn
470              475              480              485

CCA ATT CCA GCA CCG TTG CCT CCT GAC ATA CCA AGC TTC AAC CTC ATT         1722
Pro Ile Pro Ala Pro Leu Pro Pro Asp Ile Pro Ser Phe Asn Leu Ile
                 490              495              500

GGT GAC AGC CTG TCT TTC GAC TTC AAA GAT ACT GAC ATG AAG CGG CTT         1770
Gly Asp Ser Leu Ser Phe Asp Phe Lys Asp Thr Asp Met Lys Arg Leu
             505              510              515

TCC ATG GAG ATA GAG AAA GAA AAA GTG GAA TAC ATG GAA AAG AGC AAG         1818
Ser Met Glu Ile Glu Lys Glu Lys Val Glu Tyr Met Glu Lys Ser Lys
         520              525              530

CAT CTG CAG GAG CAG CTC AAT GAA CTC AAG ACA GAA ATC GAG GCC TTG         1866
His Leu Gln Glu Gln Leu Asn Glu Leu Lys Thr Glu Ile Glu Ala Leu
     535              540              545

AAA CTG AAA GAG AGG GAG ACA GCT CTG GAT ATT CTG CAC AAT GAG AAC         1914
Lys Leu Lys Glu Arg Glu Thr Ala Leu Asp Ile Leu His Asn Glu Asn
550              555              560              565

TCC GAC AGG GGT GGC AGC AGC AAG CAC AAT ACC ATT AAA AAG CTC ACC         1962
Ser Asp Arg Gly Gly Ser Ser Lys His Asn Thr Ile Lys Lys Leu Thr
                 570              575              580

TTG CAG AGC GCC AAG TCC CGA GTG GCC TTC TTT GAA GAG CTC                 2004
Leu Gln Ser Ala Lys Ser Arg Val Ala Phe Phe Glu Glu Leu
```

FIG.3E

```
                         585              590              595
TAGCAGGTGA CCCAGCCACC CCAGGACCTG CCACTTCTCC TGCTACCGGG ACCGCGGGAT    2064

GGACCAGATA TCAAGAGAGC CATCCATAGG GAGCTGGCTG GGGGTTTCCG TGGGAGCTCC    2124

AGAACTTTCC CCAGCTGAGT GAAGAGCCCA GCCCTCTTA TGTGCAATTG CCTTGAACTA     2184

CGACCCTGTA GAGATTTCTC TCATGGCGTT CTAGTTCTCT GACCTGAGTC TTTGTTTTAA    2244

GAAGTATTTG TCT                                                        2257
```

```
Human Moesin      401                                                          E         EA  Q Q  E         500
Mouse Radixin           EA  LA   EAE                             E          EA       AE  K L    P
Human Ezrin            EEA  L      AE    I  A                    E       E  R  E    EA       K L    P
Human Merlin           EEA  L     A       A                      E    E  R  E        EA       K L
Ech.mult. tegument   ITEEEAKLLAQKAAEAEQEMQRIKATAIRTEEEKRLMEQKVLEAEVLALKMAEESERRAKEADQLKQDLQEAREAERRAKQKL  LEIATKPT
Human eryth. 4.1         L                     K    EE    E         E Q        A    RR   K         T
                                          KR                   M E      E Human Moesin      501 P                  S DL     M      E E      EK    Q L L E
Mouse Radixin        PP  P               S  L            E E V    K     QL L E                         TA D  H EN   R G 600 T
Human Ezrin          P   P               S  L            E        EK    Q QL L E                       T  D LH EN      G  K  T
Human Merlin       YPPMNPIPAPLPPDIPSFNLIGDSLSFDFKDTD MKRLSMEIEKEKVEYMEKSKHLQEQLNELKTEIEALKLER           T  DI HNEN  R G  K  T
Ech.mult. tegument          S            K              E V    K   LQ L LK E                         ETALDILHNENSDRGSSKHNT
Human eryth. 4.1         P                 D                  E       E    K I       E        R         D  H N  R G  K  T
                                                                                                           DI H 601                              623
Human Moesin             K R   FE *
Mouse Radixin            K     FE *
Human Ezrin              K R   FE L*
Human Merlin         IKKLTLQSAKSRVAFFEEL*
Ech.mult. tegument       RV FE  *
Human eryth. 4.1         K V    E    *
```

FIG. 7B

```
                    200                                          240
Human Merlin    R D E A E M E Y L K I A Q D L E M Y G V N Y F A I R N K K G T E L L L G V D A L G
Human Moesin    R E D A V L E Y L K I A Q D L E M Y G V N Y F S I K N K K G S E L W L G V D A L G
Human Ezrin     K D N A M L E Y L K I A Q D L E M Y G I N Y F E I K N K K G T D L W L G V D A L G
Mouse Radixin   R E D S M M E Y L K I A Q D L E M Y G V N Y F E I K N K K G T E L W L G V D A L G
```

FIG. 12

```
AGTGCAGAGA AAAGGTTTTA TTAATGATTT TTGCTCACAG TGTCCTTCCC CATTGGTTTG    60
TTATTGCAGA TGAAGTGGAA AGGGAAGGAC CTCTTTGATT TGGTGTGCCG GACTCTGGGG   120
CTCCGAGAAA CCTGGTTCTT TGGACTGCAG TACACAATCA AGGACACAGT GGCCTGGCTC   180
AAAATGGACA AGAAGGTTGG GCTAGAACTC GATGAAACTG GTGGGGCTGA CGTGAGCTTT   240
CCA                                                                243
```

FIG.15A

```
GCTTCTTTGA GGGTAGCACA GGAGGAAGTG CCAATATANN GTGTGTTTGT CTTTTGCTCT    60
GCAATTCTGC AGGTACTGGA TCATGATGTT TCAAAGGAAG AACCAGTCAC CTTTCACTTC   120
TTGGCCAAAT TTTATCCTGA GAATGCTGAA GAGGAGCTGG TTCAGGAGAT CACACAACAT   180
TTATTCTTCT TACAGGTACA TCAGTCAAGG CTACCCCCCA GTTCTGAGAG AGAACTTGCC   240
CAGGAGTGGT TGCAGAGTTG GCCTCAGAGT TGACC                             275
```

FIG.15B

```
GCTAAAGGGC TCAGAGTGCA GGCCGTGGGG CGCGAGGGTC CCGGGCCTGA GCCCCGCGCC    60
ATGGCCGGGG CCATCGCTTC CCGCATGAGC TTCAGCTCTC TCAAGAGGAA GCAACCCAAG   120
ACGTTCACCG TGAGGATCGT CACCATGGAC GCCGAGATGG AGTTCAATTG CGACGTAACC   180
GGCCGGCAGC CCCGACTGCT GCGGTGACAG TCGAGGTGGA AGCTCGAGAG GTTCTC       236
```

FIG.15C

```
CCTCACTTCC CCTCACAGAG TATCATGTCT CCCTTGTTGC TCCTTTCAGG TAAAGAAGCA    60
GATTTTAGAT GAAAAGATCT ACTGCCCTCC TGAGGCTTCT GTGCTCCTGG CTTCTTACGC   120
CGTCCAGGCC AAGGTAGGCT CAAAGAAGAA AAATGTATTT TTNNCTGGGC GTTAATTTGG   180
GTCATGGG                                                            188
```

FIG.15D

```
TGGCAGTTAT CTTTAGAATC TCAATCGCCT GCTCTCCCTT TCTTCTTTCC AGATGGTGA     60
CTACGACCCC AGTGTTCACA AGCGGGGATT TTTGGCCCAA GAGGAATTGC TTCCAAAAAG   120
GGTAAGAGAT TAAATTCCCT TTTCAGGAAG ACATAGCAGA TATGTGGTCT AAAAGAAAGC   180
TAACCAAAGG ACTTGAAGGA                                               200
```

FIG.15E

```
TCTGTGTGAC TACTCCTGGT GTAGCTTTAA AATAGCTTTA CTGTTTGTAA AATGATGCAT    60
AATTATAAAA GTGGCAAACA ATACCAAATT TACTTCATGT GTAGGTTTTT TATTTTGCTC   120
TATTTTTTGG TAGGTAATAA ATCTGTATCA GATGACTCCG GAAATGTGGG AGGAGAGAAT   180
TACTGCTTGG TACGCAGAGC ACCGAGGCCG AGCCAGGTGA GGCCCATTCA TTGTTGGTTT   240
ACATTCCTTT ATGGGC                                                   256
```

FIG.15F

| | |
|---|---|
| GAATGCTTGA TTTGGTGGCC CACCCGCTCT CCACCCATCT CACTTAGCTC CAATGACAGT | 60 |
| GTCTTCCGTT CTCCCCACAG GGATGAAGCT GAAATGGAAT ATCTGAAGAT AGCTCAGGAC | 120 |
| CTGGAGATGT ACGGTGTGAA CTACTTTGCA ATCCGGTGT GTTGAAACCT CTCTGAGCTC | 180 |
| CTTGTGTAGT AGACAGAGAC TGAGTGAGGG CCAGGACTGC TAAAATGGTT ACTTCTTCAT | 240 |

FIG.15G

| | |
|---|---|
| TCTGTGGACC TGCTGAACTG CACATGTGAC AGTGTGTGCC AGATTCTTTG GAAGGTTGAA | 60 |
| TAAAATTTTG AGCCTCAGCT GGCGCTTACA GTAGCTGTTC TTATTGGATC CACAGAATAA | 120 |
| AAACGGCACA GAGCTGCTGC TTGGAGTGGA TGCCCTGGGG CTTCACATTT ATGACCCTGA | 180 |
| GAACAGACTG ACCCCCAAGA TCTCCTTCCC GTGGAATGAA ATCCGAAACA TCTCGTACAG | 240 |
| TGACAAGGAG GTAGGACATG TGTGTACTGC AGATGGGTCC AGCAGATCTT TCCCTGTCTG | 300 |
| CCCCCCTCAC TGGAGCCTCC CCAGCCAGGG CATCTCCTTG TTATTCATAG AGTCCTTTAA | 360 |
| TTCCCAGGCT TTGAGGGTGT GGTTGTT | 387 |

FIG.15H

| | |
|---|---|
| GACTTGGTGC TCCTAATTCC CTGAGGTTTA GTGCCTGGAT ACTGGGAAGC CAGNACAAGG | 60 |
| GCATAACNTC ATGCTGGTCT GTGGCCAGTG TGGTTGCCGCA TTTGTGGAAT TNCCAATTGC | 120 |
| TGCTAACATT CCAGGCTGTC GGACTGAAAC TGTGTTCTGC TTCATTCTTC CAGTTTACTA | 180 |
| TTAAACCACT GGATAAGAAA ATTGATGTCT TCAAGTTTAA CTCCTCAAAG CTTCGTGTTA | 240 |
| ATAAGCTGGT AAGTTGAGAT CCTGGTAAGT TGAGATCCTG GTTTTCATTA CTGATAATGG | 300 |

FIG.15I

| | |
|---|---:|
| TGCTACCTGC AAGAGCTCAA ACTGCTATGG CACTAGTGGG CCAGTAGGCA GTGAAGTAAA | 60 |
| TTTGTGGATA TTAACCTTTT TGTCTGCTTC TGTGGCCACA GATTCTCCAG CTATGTATCG | 120 |
| GGAACCATGA TCTATTTATG AGGAGAAGGA AAGCCCATTC TTTGGAAGTT CAGCAGATGA | 180 |
| AAGCCCAGGC CAGGGAGGAG AAGGCTAGAA AGCAGGTGAG CACAACCTTG TTTTAACTGA | 240 |
| TGATGTCACT GTGTGGTCAG | 260 |

FIG.15J

| | |
|---|---:|
| TCTTTGGCCC TTGTGGCACC CTAGGTCTCG AGCCCTGTGA TTCAATGACT GTTTTTCTTC | 60 |
| ACCCCTCGCA GATGGAGCGG CAGCGCCTCG CTCGAGAGAA GCAGATGAGG GAGGAGGCTG | 120 |
| AACGCACGAG GGATGAGTTG GAGAGGAGGC TGCTGCAGAT GAAAGAAGAA GCAACAATGG | 180 |
| CCAACGAAGC ACTGGTGATT TCTGAGGGGC TGGGGTTCCA GGAGGCTACT TGGGGACTTC | 240 |
| CTTGGCTTTT CTGGAGCTTG GTCTCCTGAA AACATGAGTT AGCAGCGTTT GC | 292 |

FIG.15K

| | |
|---|---:|
| CGGGAGAACA GCACATGATC CCACTTCAGC TAAGAGCACT GTGCCCTCCA GATGCGGTCT | 60 |
| GAGGAGACAG CTGACCTGTT GGCTGAAAAG GCCCAGATCA CCGAGGAGGA GGCAAAACTT | 120 |
| CTGGCCCAGA AGGCCGCAGA GGCTGAGCAG GAAATGCAGC GCATCAAGGC CACAGCGATT | 180 |
| CGCACGGAGG AGGAGAAGCG CCTGATGGAG CAGAAGGTGC TGGAAGCCGAG GTGCTGGCA | 240 |
| CTGAAGATGG CTGAGGAGTC AGAGAGGAGG TGAGGGGGCA CCGGGCACCA GACTGGCGAG | 300 |
| GAGGCTGGCG AAGGGCCGCA GACCAGCCTG CCCTGAGGCT GACCTCTACA GCAGTTGTCC | 360 |
| TCAAG | 365 |

FIG.15L

```
GGTGTCTTTT CCTGCTACCT GCCCTCTTCT GTGAAGCTGA CATCTCATCC TTTCCTTGCA    60

CGGCCAAAGA GGCAGATCAG CTGAAGCAGG ACCTGCAGGA AGCACGCGAG GCGGAGCGAA   120

GAGCCAAGCA GAAGCTCCTG GAGATTGCCA CCAAGCCCAC GTACCCGGTG AGCCTGGGGG   180

CCACCAGCTG GGGCTGCCTT AGTCCTGGTG ATGTTCTCTT TCCTCCC                 227
```

FIG.15M

```
TGTGCCATTG CCTCTGTGGC TGCTGGAGGA TCGGTTGTCA ACACAGTAGT GTCCTTCTGT    60

GCTTGTATGA CCCAAGCTCC TAATCCGAAA TTTCTCATTA ACACCCCATG AACCCAATTC   120

CAGCACCGTT GCCTCCTGAC ATACCAAGCT TCAACCTCAT TGGTGACAGC CTGTCTTTCG   180

ACTTCAAAGA TACTGACATG AAGCGGCTTT CCATGGAGAT AGAGAAAGAA AAGTATGTAG   240

CCCCCTGTGC CCTGCTGTGG GCTTGCTGTG AACTAGACTG A                      281
```

FIG.15N

```
TGGCCAAGTA GAGACGTGAN NCCAGCNTNA AACCCTAGAT CGCACACCAA GCAGCTTGTG    60

GGCCACAGAG CACCTGAGCC GTGTCTCACT GTCTGCCCAA GCCCTGATGC ATGATACCCT   120

CTTGCCGGCA CAGTGGAATA CATGGAAAAG AGCAAGCATC TGCAGGAGCA GCTCAATGAA   180

CTCAAGACAG AAATCGAGGC CTTGAAACTG AAAGAGAGGG AGACAGCTCT GGATATTCTG   240

CACAATGAGA ACTCCGACAG GGGTGGCAGC AGCAAGCACA ATACCATTAA AAAGGTACCC   300

AGGGTCTCTT TCTTGTATTT TGCTGATCAG GACCA                              335
```

FIG.15O

```
CAAACAAAAT CACTCATCAC GATNTCAGGC CTATCCAAGC ATTTTGCANA TGGCACTTAT    60

GGCATTGTTG ATATCACAGG GTATGTTTTT GTTTTTCTTC ATTTTATTTT GCTGGTTTAG|  120

CCTCAAGCCC AAGGCAGAAG ACCTATCTGC ATTTGAGCCC TCAAAGTAGC TTGTTCCCAG   180

GTACTCTCTA TGTGGTGATG GTGCTGCCCT CTGTGATACT AACCCGTGCA TGAGNTTGCC   240

TGTCTCTGTC TCGG                                                    254
```

FIG.15P

```
AGGACCCTGT GAGACAGAGC GGAGGTCNNG TGCCCTCTCA GCTTCTTCTC TGCTTTCTTA    60

CAGCTCACCT TGCAGAGCGC CAAGTCCCGA GTGGCCTTCT TTGAAGAGCT CTAGCAGGTG   120

ACCCAGCCAC CCCAGGACCT GCCACTTCTC CTGCTACCGG GACCGCGGGA TGGACCAGAT   180

ATCAAGAGAG CCATCCATAG GGAGCTGGCT GGGGGTTTCC GTGGGAGCTC CAGAACTTTC   240

CCCAGCTGAG TGAAGAGCCC AGCCCCTCTT ATGTGCAATT GCCTTGAACT ACGACCCTGT   300

AGAGATTTCT CTCATGGCGT TCTAGTTCTC TGACCTGAG                         339
```
* 3' BOUNDARY NOT DETERMINED

FIG.15Q

TUMOR SUPPRESSOR MERLIN AND ANTIBODIES THEREOF

This is a division of application Ser. No. 08/171,718, filed Dec. 22, 1993; which is a continuation-in-part of application Ser. No. 08/108,808, filed Aug. 19, 1993 (abandoned); which is a continuation-in-part of application Ser. No. 08/026,063, filed Mar. 4, 1993 (abandoned); which is a continuation-in-part of application Ser. No. 08/022,034, filed Feb. 25, 1993 (abandoned).

Part of the work performed during development of this invention utilized U.S. Government funds; the U.S. Government has certain rights in this invention.

FIELD OF THE INVENTION

The invention is in the field of genetic disease diagnosis, tumor detection and treatment, and genetic therapy. Specifically, the invention is directed to the merlin gene, merlin protein, and the use of the gene and/or protein for (1) detecting a predisposition to develop tumors especially neurofibromatosis-2, (2) diagnosing certain tumors, especially neurofibromatosis-2, (3) treating tumors, especially neurofibromatosis-2, (4) monitoring the course of tumor treatment, especially neurofibromatosis-2 treatment, and (5) gene replacement in affected non-tumor tissues or cells.

BACKGROUND OF THE INVENTION

Neurofibromatosis (NF) describes two major human genetic disorders that display autosomal dominant inheritance, involve tumors of the nervous system, and which are distinct clinical entities (Mulvihill, J. J. et al. *Ann. Intern. Med.* 113:39–52 (1990)). NF1, or von Recklinghausen NF, is more common (incidence of 1/4,000) and is characterized by the highly variable expression of an array of features that include neurofibromas, cafe-au-lait macules, Lisch nodules of the iris, and a predisposition to certain malignant tumors (Riccardi, V. M. et al., *N. Engl. J. Med.* 305:1617–1627 (1981); Riccardi, V. M. et al., "Neurofibromatosis: Phenotype, Natural History, and Pathogenesis," Johns Hopkins Univ. Press, Baltimore, Md. (1986)). It is caused by defects in a gene on chromosome 17 that has recently been isolated and characterized (Viskochil, D. et al., *Cell* 62:187–192 (1990); Cawthon, R. M. et al., *Cell* 62:193–201 (1990); Wallace, M. R. et al., *Science* 249:183–186 (1990)). The NF1 gene product, neurofibromin, is a large protein with a GAP-related domain and is presumably involved in modulating a signal transduction pathway whose disruption can lead to tumor formation (Ballester, R. et al., *Cell* 63:851–859 (1990); Buchberg, A. M. et al., *Nature* 347:291–294 (1990); Xu, G. et al., *Cell* 62:599–608 (1990); DeClue, J. E. et al., *Cell* 69:265–273 (1992); Basu, T. N. et al., *Nature* 356:713–715 (1992)).

In contrast, neurofibromatosis-2 (NF2), which occurs in about 1/40,000 livebirths (Evans, D. G. R. et al., *J. Med. Genet.* 29:841–846 (1992)), is characterized by bilateral schwannomas that develop on the vestibular branch of the 8th cranial nerve. Pressure from these tumors often causes hearing loss and vestibular symptoms in the second and third decade. Other tumors of the brain, especially meningiomas and schwannomas of other cranial nerves and spinal nerve roots (Martuza, R. L. et al., N. Engl. J. Med. 318:684–688 (1988)), and posterior capsular lens opacities (Kaiser-Kupfer, M. I. et al., *Arch. Ophthalmol.* 107:541–544 (1989) are commonly present in the young affected adult.

The NF2 gene is highly penetrant. Ninety-five percent of persons with the genotype develop bilateral vestibular schwannomas. NF2 is often more severe than NF1. Teenage or early adulthood onset of multiple slow growing tumors that can gradually cause deafness, balance disorder, paralysis or increasing neurologic problems necessitating repeated surgical procedures, characterizes NF2.

NF2 has been shown to be genetically distinct from NF1 by linkage studies that assigned the NF2 gene to chromosome 22 (Rouleau, G. A. et al., *Nature* 329:246–248 (1987); Wertelecki, W. et al. *N. Engl. J. Med.* 319:278–283 (1988); Rouleau, G. A. et al., *Am. J. Hum. Genet.* 46:323–328 (1990); Narod, S. A. et al., *Am. J. Hum. Genet.* 51:486–496 (1992)). The tumor types that occur in NF2 can be seen in the general population as solitary, sporadic tumors. Since frequent loss of alleles on chromosome 22 from both sporadic vestibular schwannomas and meningiomas, and from their counterparts in NF2 had been noted previously, the localization of the inherited defect to the same chromosome region suggested that the NF2 locus encodes a recessive tumor suppressor gene (Knudson, A. G. et al., *Proc. Natl. Acad. Sci. U.S.A.* 68:820–823 (1971)) whose inactivation leads to tumor formation (Seizinger, B. R. et al., *Nature* 322:644–647 (1986); Seizinger, B. R. et al., *Science* 236:317–319 (1987); Seizinger, B. R. et al., *Proc. Natl. Acad. Sci. U.S.A.* 84:5419–5423 (1987)).

A number of studies of sporadic tumors and tumors from NF2 patients have provided support for this hypothesis (Couturier, J. et al., *Cancer Genet. Cytogenet.* 45:55–62 (1990); Rouleau, G. A. et al., *Am. J. Hum. Genet.* 46:323–328 (1990); Fiedler, W. et al., *Genomics* 10:786–791 (1991); Fontaine, B. et al., *Ann. Neurol.* 29:183–196 (1991); Fontaine, B. et al., *Genomics* 10:280–283 (1991); Bijlsma, E. K. et al., *Genes Chromosom. Cancer* 5:201–205 (1992); Wolff, R. K. et al., *Am. J. Hum. Genet.* 51:478–485 (1992)). The combined use of family studies and tumor deletion mapping has progressively narrowed the location of NF2 within the q12 band of chromosome 22, and defined a candidate region in which to search for the NF2 genetic defect (Rouleau, G. A. et al., *Am. J. Hum. Genet.* 46:323–328 (1990); Wolff, R. K. et al., *Am. J. Hum. Genet.* 51:478–485 (1992)).

5'CAGATTGTTCATTCCAAGTGG3' [SEQ ID No: 1] and

5'ACCCTGAGGAATCCACTACC3' [SEQ ID No: 2], product size—124 bp) and 96T7

(5'TGCACACACATCCTTTTCAC3' [SEQ ID No: 3], and

5'GAGAGAGACTGCTGTCTCAAAAA3' [SEQ ID No: 4], product size-92 bp) are sequence-tagged site assay (STS)-derived from the T3 and T7 ends of 96C10, respectively.

X-XhoI recognition site. Arrows indicate the orientation of transcription and approximate genomic coverage of CDNA JJR-1.

FIGS. 3A–3F. Complete nucleotide and predicted amino acid sequence of merlin JJR-1 CDNA clone [SEQ ID No: 15 and 16, respectively]. Common moesin-ezrin-radixin domain spans amino acid residues 1–358. Arrow indicates where poly-A addition has occurred in two independent clones (JJR-6 and JJR-9).

Figure 4:
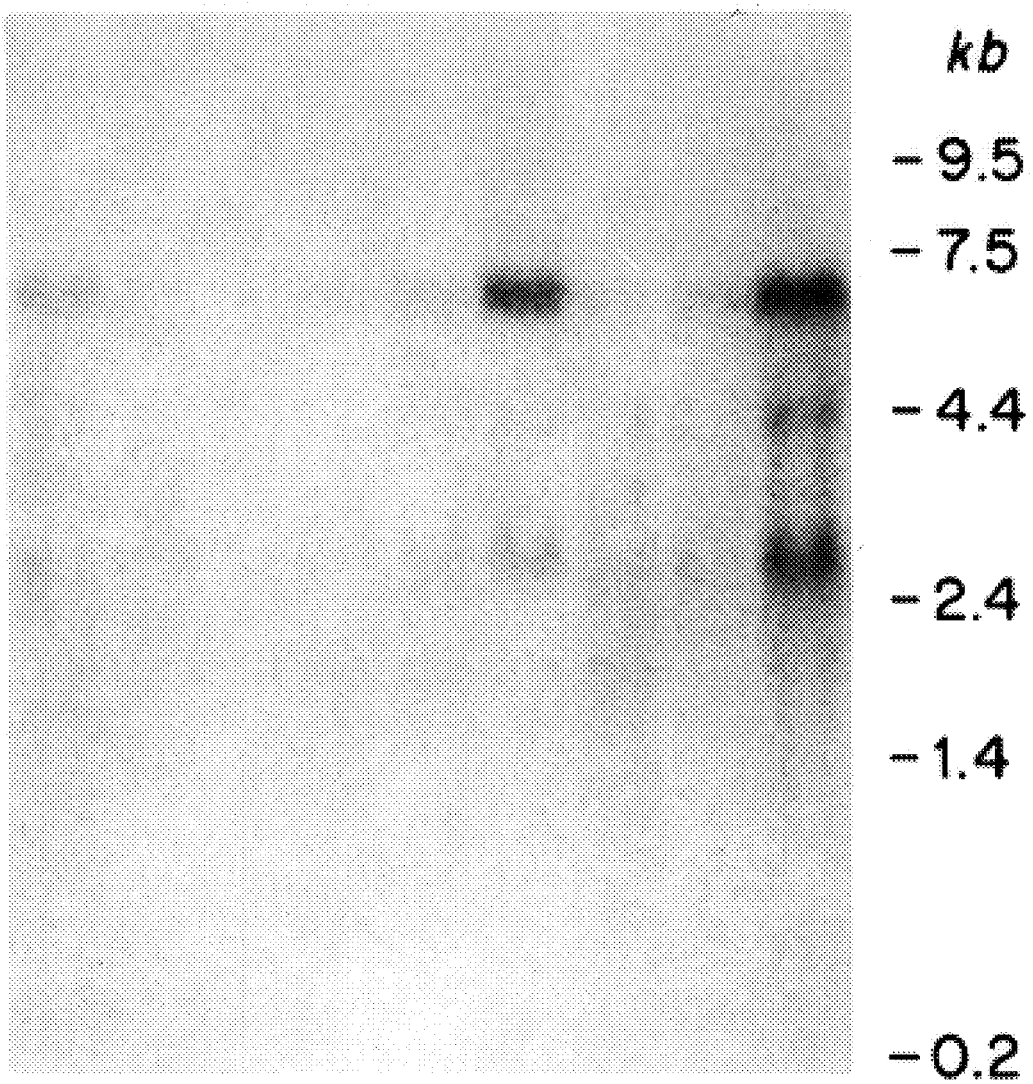

FIG. 4. Northern blot analysis of RNA derived from human tumor cell lines. RNA was size-fractionated by electrophoresis in formaldehyde-agarose, blotted and hybridized as described in Experimental Procedures. The blot was hybridized with a radiolabeled probe corresponding to bases 1253–1942 of the JJR-1 cDNA. Lane 1, SK-N-NB neuroblastoma; lane 2, T98G glioblastoma; lane 3, WERI retinoblastoma; lane 4, MCF-7 breast carcinoma; lane 5, HOS osteosarcoma; lane 6, HEPG2, liver carcinoma; lane 7, CATA4 kidney carcinoma; lane 8, SW480 colon carcinoma; lane 9, EJ bladder carcinoma.

Figure 5:
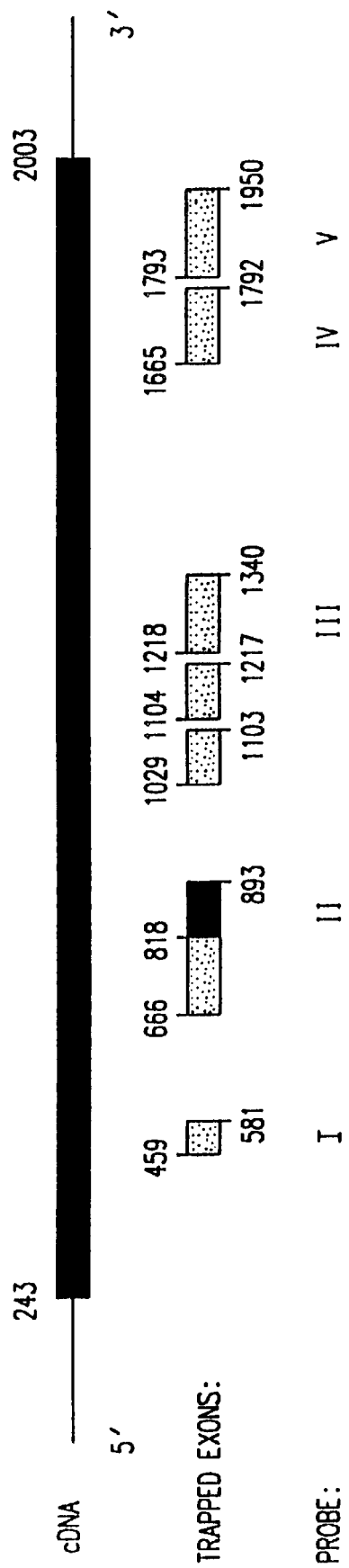
Figure 5A:

FIG. 5. Location of trapped exons in JJR-1 cDNA. The blackened box in the cDNA indicates open reading frame; a thin line indicates both 5' and 3' untranslated regions. Probe names correspond to those used in FIGS. 5A and B. Probe II (5A) represents bp 818–893 of JJR-1 and is overlapped by another trapped product. These overlapping products may have arisen from partial digestion of the cosmid or alternative splicing in COS7 cells occurring during exon amplification analysis.

FIGS. 5A–5E (probes I and II). Southern blot analysis of GUS5069 X hamster hybrid cell lines harboring the altered chromosome 22. DNA samples were digested with BamHI, size-fractionated in agarose gels, blotted and hybridized with radiolabeled probes indicated above each panel. Lane 1, GUS1323 (human control); lane 2, CHTG49 (hamster control); lane 3, GUSH134A3 (hybrid with deleted homolog); lane 4, GUSH134B1 (hybrid with deleted homolog); lane 5, GM 10888 (chromosome 22-only hybrid); lane 6, Eye3A6 (hybrid containing chromosome 22 and smaller portions of two to three other chromosomes).

Figure 5B:
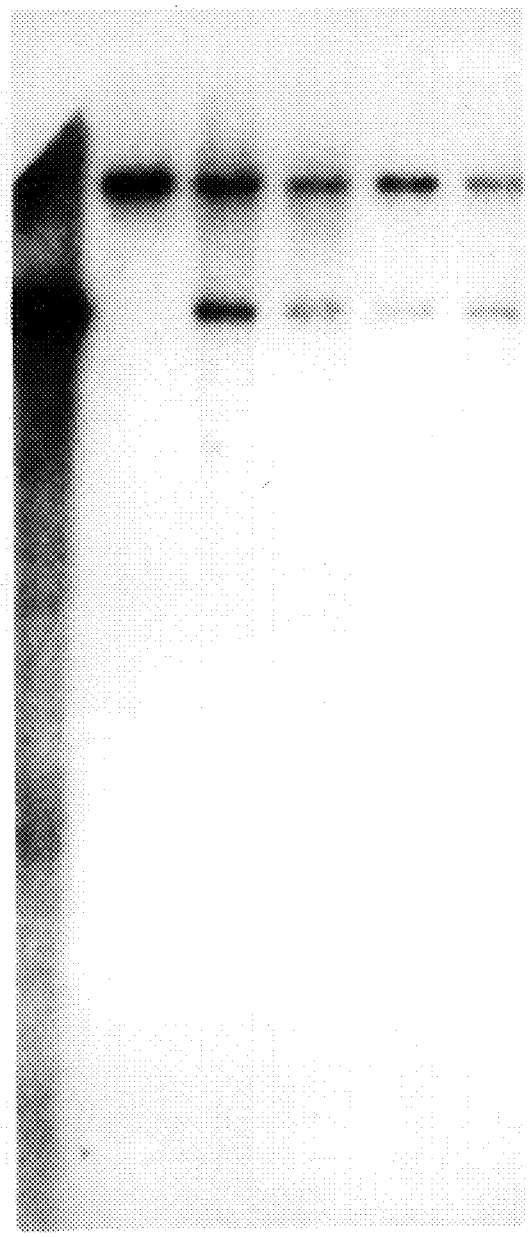
Figure 5C:
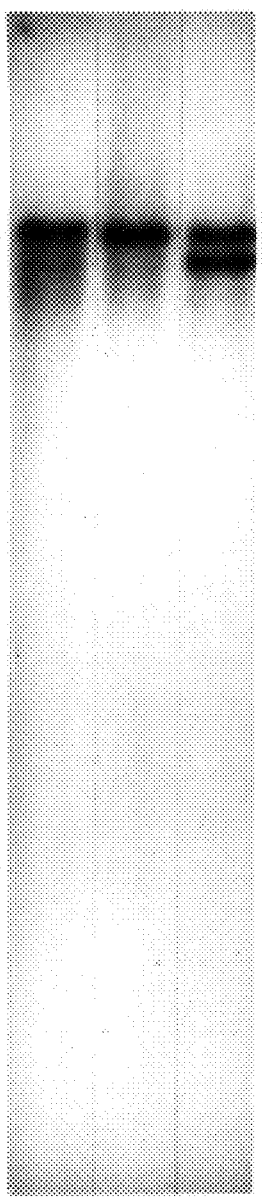
Figure 5D:
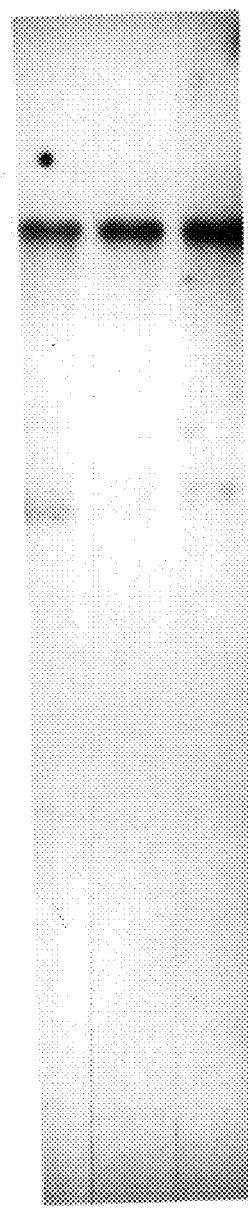
Figure 5E:
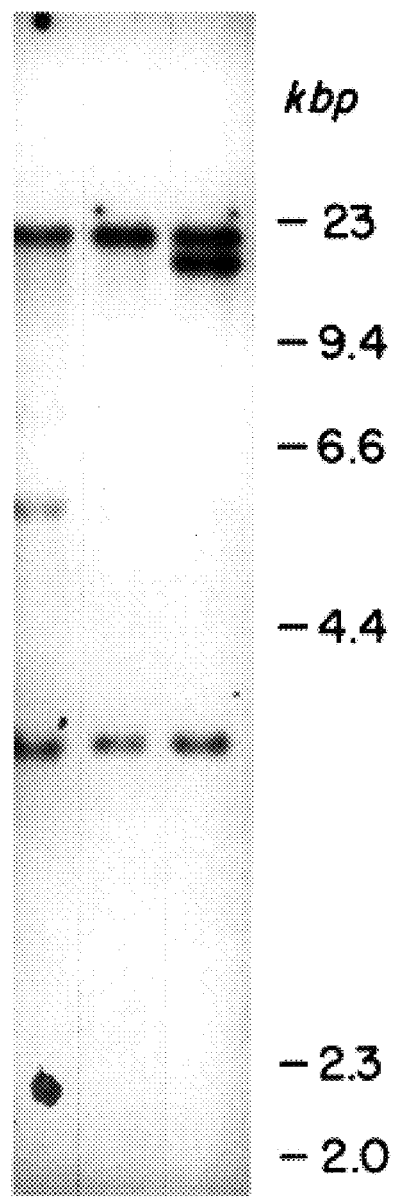

FIG. 5B (probes III, IV and V). Southern blot analysis of NF2 patient lymphoblast DNA. Samples were digested with EcoRI, size-fractionated, blotted and hybridized with radiolabeled probes indicated above each panel. Lane 1, GUS1323 (human control); lane 2, GUS5069 (NF2 affected); lane 3, GUS5722 (NF2 affected). Probe V is comprised of multiple exons and recognizes multiple genomic fragments.

Figure 6:
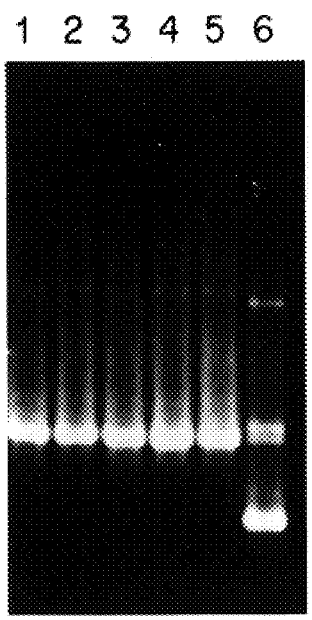

FIG. 6. PCR analysis of RNA from lymphoblasts of affected NF2 patients. RNA-PCR was performed as described in Experimental Procedures. Samples were subjected to electrophoresis in a 1.5% agarose gel and visualized by staining with ethidium bromide and ultraviolet illumination. The products seen correspond to the RNA sequence encompassed by bases 1258 to 1947 (Primer pair:

5'AGGAGGCTGAACGCACGAG3' [SEQ ID No: 5] and

5'TGGTATTGTGCTGCTGCTG3' [SEQ ID No: 6].

Lanes 1, 2, 4, lymphoblasts from independent NF2 patients: lane 3, GUS5068; lane 5, normal control lymphoblast; lane 6, GUS5722.

Figure 6A:
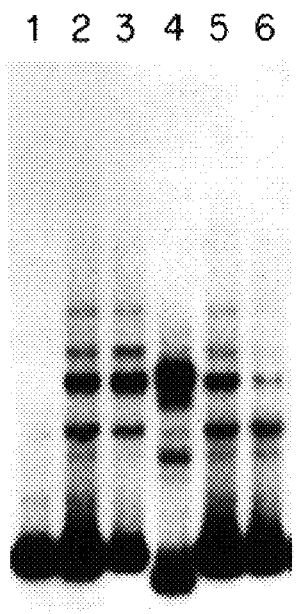
Figure 6B:

FIGS. 6A and 6B. SSCP analysis of RNA samples derived from primary cultures of meningioma tumors from NF2 patients. Lane 1, undenatured PCR product from the tumor in lane 2; lanes 2, 3, 4, and 5, denatured PCR product from independent primary NF2 meningiomas; lane 6, denatured PCR product from GUS5068 lymphoblast. The PCR reactions amplified the following segments: FIG. 6A. bp 1709–1947 (Primer pair:

5'CTTCAACCTGATTGGTGACAG3' [SEQ ID No: 7] and

5'TGGTATTGTGCTTGCTGGTG3' [SEQ ID No: 8]

and FIG. 6B: bp 457–730 (Primer pair:

5'AGGTACTGGATCATGATGTTTC3' [SEQ ID No: 9] and

5'TTTGGAAGCAATTCCTCTTGG3') [SEQ ID No: 10].

All lanes contain a proportion of undenatured product, detected by comparison with lane 1.

FIGS. 7A–7B. Comparison of sequence identities in merlin-related proteins. The program PILEUP of the GCG package (Devereux, J. et al., Nucleic Acids Res. 12:387–395 (1984)) was used to generate an optimal alignment of the protein products translated from the following GenBank files: Human Moesin (M69066); Human Ezrin (X51521); Mouse Radixin (S66820); Echinococcus multilocularis tegument protein (M61186); human erythrocyte protein 4.1 (M14993). Only amino acid identities are shown; non-identical residues are indicated by "." and gaps introduced by the program are represented by empty spaces.

Figure 8:
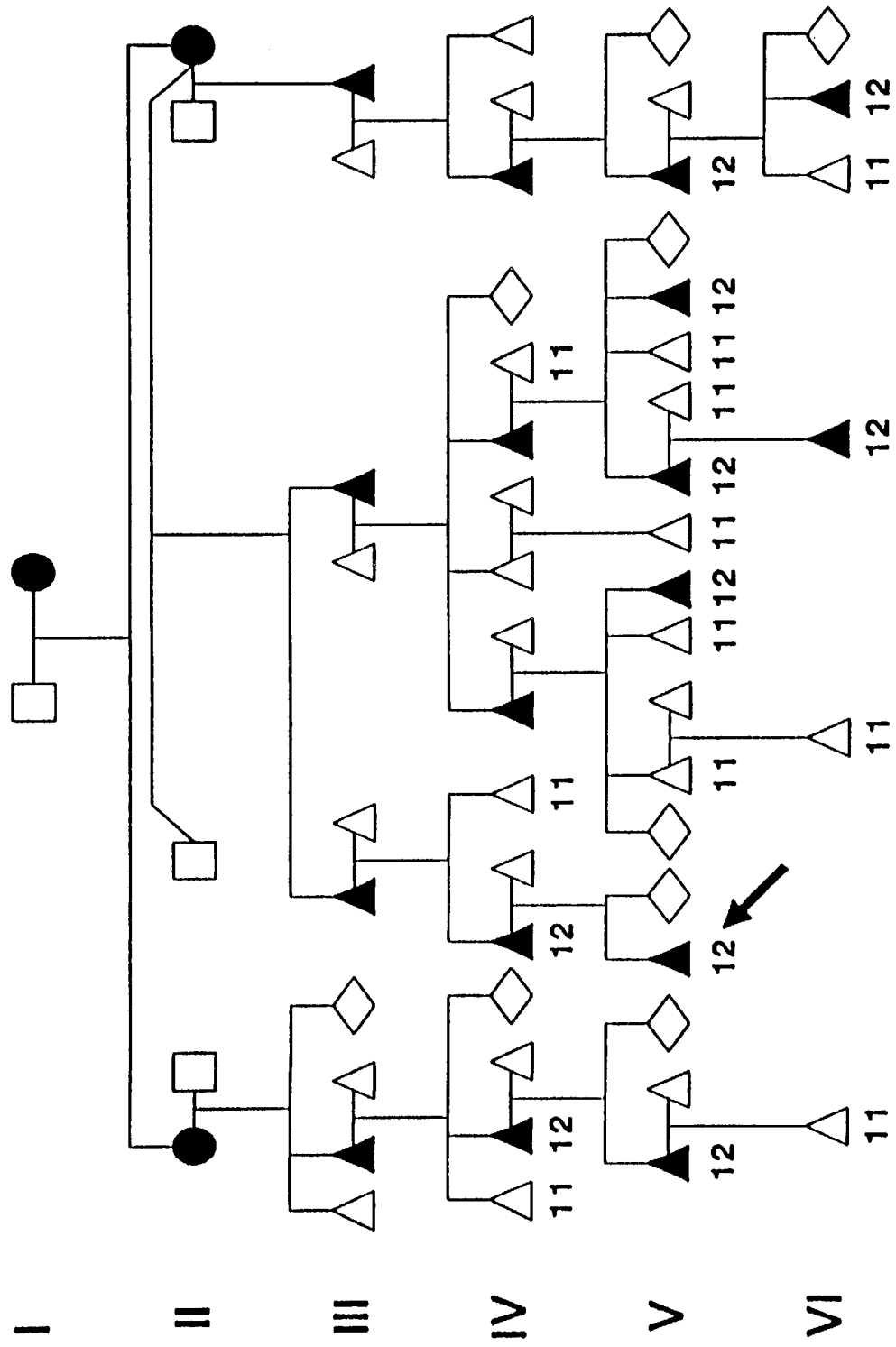

FIG. 8. Pedigree of family with neurofibromatosis type 2.

Only a portion of the large NF2 family described in detail previously (Wertelecki, W. et al., New Engl. J. Med. 319:278–283 (1988)) is presented here schematically. Affected individuals are shown by a filled symbol. The sex for each individual in generations III through VI is not given to protect confidentiality. Diamond symbols indicate the presence of one or more additional offspring in a sibship, with no indication of NF2 status being presented, again to disguise the pedigree and provide confidentiality. The deduced genotypes for selected individuals are shown below the corresponding symbol as "1 1" (homozygous for the normal Asn220 codon) and "1 2" (heterozygous with one normal Asn220 codon, and one mutated Tyr220 codon). The arrow indicates the affected individual used in the initial screen to detect the putative mutation.

Figure 9:
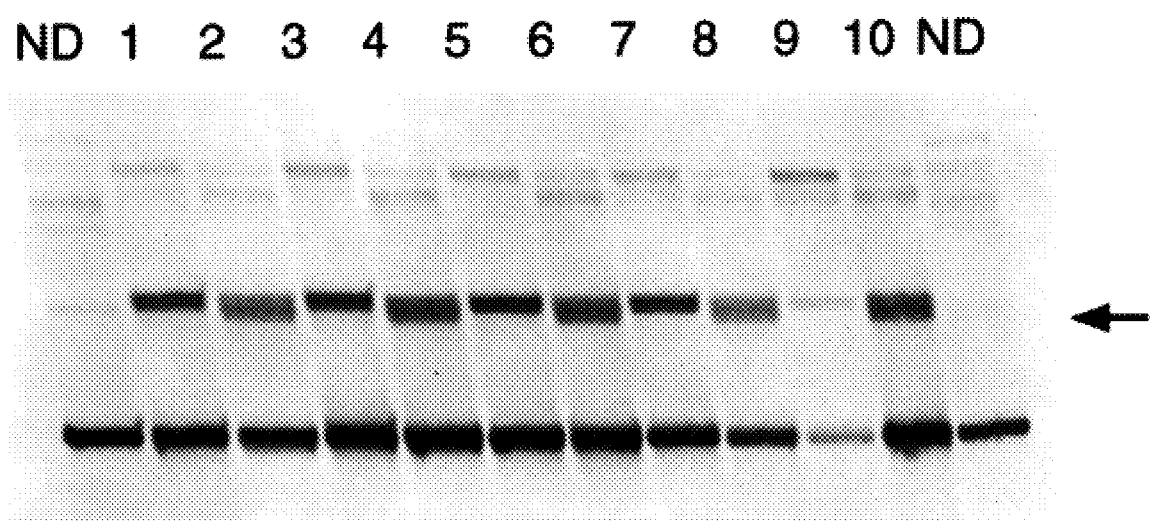

FIG. 9. SSCP analysis of affected and unaffected individuals.

A non-denatured sample (ND) was run to identify the mobility of residual double stranded PCR product. Bands of abnormal mobility appear in lanes containing DNA derived from affected individuals and are identified by a small arrowhead. Samples represent paired sibs, with the odd numbered samples being from unaffecteds, and the even numbered samples deriving from affecteds.

Figures 10A, 10B:
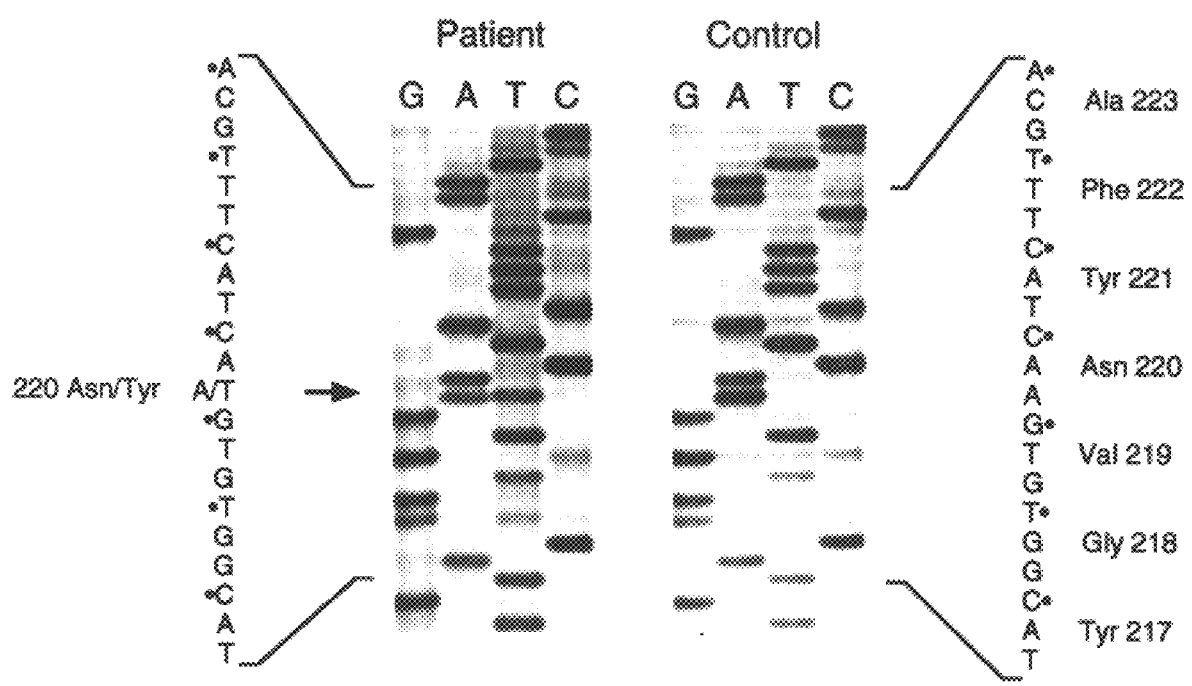

FIGS. 10A–10B. Direct DNA sequence analysis of the alteration.

The DNA sequence surrounding the site of the putative mutation is shown for both a patient [SEQ ID NO:97] and normal control sample [SEQ ID NO:98], with the corresponding protein sequence [SEQ ID NO:99] aligned by codon. The patient displays both an A and a T residue as the first base of codon 220 indicating the presence of a Tyr codon in addition to the normal Asn codon.

Figure 11:
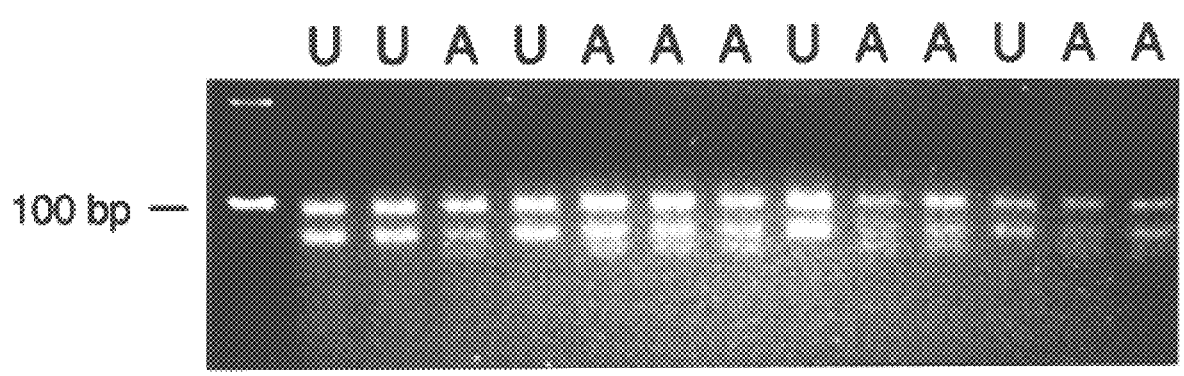

FIG. 11. RsaI digestion to confirm the presence of the Asn220/Tyr mutation in affected individuals.

The amplified PCR products containing exon 7 from affected (A) and unaffected (U) individuals were digested with the restriction enzyme RsaI and the fragments visualized on ethidium bromide stained 4% agarose gel (3% Nu-Sieve GTG agarose containing 1% Seakem agarose, FMC Bioproducts). The PCR products from unaffected individuals yield two fragments of 96 bp and 76 bp, due to digestion of a RsaI site at crossing codons 216–217. The PCR products from affected individuals produce an additional fragment of 67 bp due to digestion of the new RsaI site at codons 219–220.

FIG. 12. Conserved sequence domain affected by the putative mutation.

The amino acid sequence from residues 200–240 of the merlin protein is shown relative to the homologous regions for human moesin, human ezrin and mouse radixin (Trofatter, J. et al., Cell 72:791–800 (1993)). The Asn residue (N) altered to a Tyr by the putative NF2 mutation is starred.

Figure 13A:
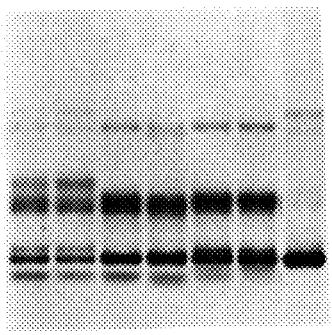
Figure 13B:
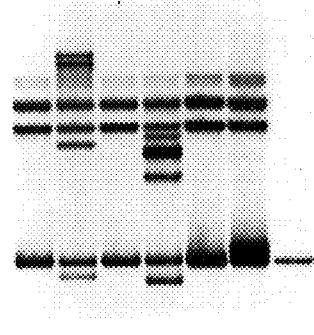
Figure 13C:
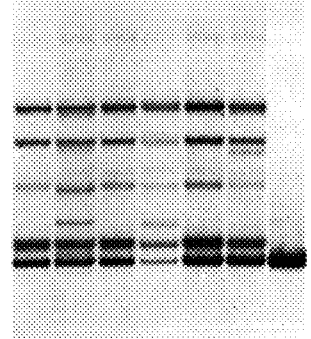

FIGS. 13A–13C. Representative SSCP analyses.

For each exon, control blood (B) and tumor (T) DNAs were analyzed and a nondenatured sample (ND) was included. Abnormal migration patterns are observed for each tumor DNA. Two blood DNAs from NF2 patients, S11 and S33, show the same alterations in E2 as the tumor DNAs, suggesting that these shifts represent germline mutations.

Figure 14A:
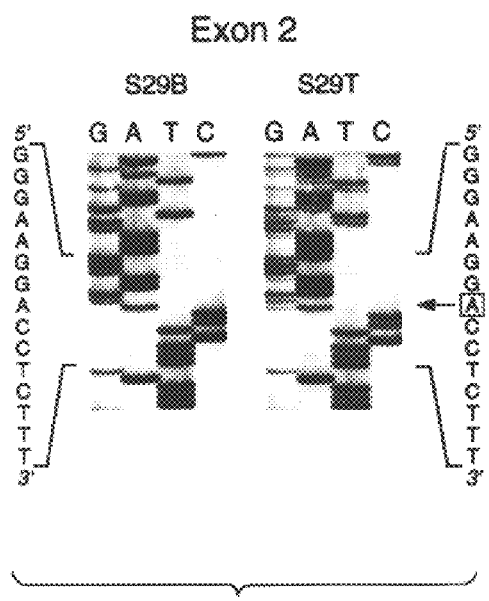
Figure 14B:
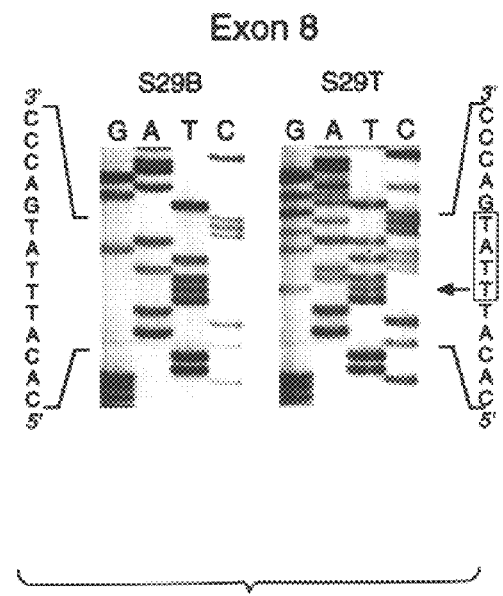

FIGS. 14A–14B. Direct DNA sequence analysis of two alterations in S29.

The DNA sequences surrounding the sites of two mutations are shown for tumor DNA (T) [SEQ ID NOS: 119 and 120] and control blood DNA (B) [SEQ ID NOS: 100 and 101] from patient S29. The tumor is heterozygous for each of a one base pair deletion in exon 2[SEQ ID NO: 119] and a four base pair deletion in exon 8,[SEQ ID NO: 120] (shown in boxes). These deletions are predicted to generate premature stop codons at positions 123 and 251, respectively.

FIGS. 15A through 15Q. Exon sequences in the merlin gene with intron boundary sequences.

15A: Exon 1 [SEQ ID NO: 102].
15B: Exon 2 [SEQ ID NO: 103].
15C: Exon 3 [SEQ ID NO: 104].
15D: Exon 4 [SEQ ID NO: 105].
15E: Exon 5 [SEQ ID NO: 106].
15F: Exon 6 [SEQ ID NO: 107].
15G: Exon 7 [SEQ ID NO: 108].
15H: Exon 8 [SEQ ID NO: 109].
15I: Exon 9 [SEQ ID NO: 110].
15J: Exon 10 [SEQ ID NO: 111].
15K: Exon 11 [SEQ ID NO: 112].
15L: Exon 12 [SEQ ID NO: 113].
15M: Exon 13 [SEQ ID NO: 114].
15N: Exon 14 [SEQ ID NO: 115].
15O: Exon 15 [SEQ ID NO: 116].
15P: Exon 16 [SEQ ID NO: 117].
15Q: Exon 17 [SEQ ID NO: 118].

The vertical line on the left indicates the 5' intron exon boundary. The vertical line on the right indicates the intron exon 3' boundary. The designation "N" indicates that the nucleotide is not definitively determined.

SUMMARY OF THE INVENTION

The invention is directed to the protein merlin, mutants thereof, nucleic acid encoding this protein, nucleic acid encoding merlin regulatory regions and exons, mutant nucleic acid sequences, and uses thereof.

Accordingly, in a first embodiment, the invention is directed to purified preparations of the protein merlin, or mutants thereof.

In a further embodiment, the invention is directed to an isolated nucleic acid sequence encoding merlin, or mutants thereof.

In a further embodiment, the invention is directed to a recombinant construct containing nucleic acid encoding merlin, or mutants thereof.

In a further embodiment, the invention is directed to a vector containing nucleic acid encoding merlin, or mutants thereof.

In a further embodiment, the invention is directed to a host transformed with the vector.

In a further embodiment, the invention is directed to a method for producing merlin from the recombinant host.

In a further embodiment, the invention is directed to a method for diagnosing a merlin-associated tumor, such tumor being a tumor characterized by a loss, alteration, or decrease of the activity of the merlin tumor suppressor in the cells of said tumor, and especially by a loss or mutation of the merlin gene, in such cells. In one specific embodiment, the mutation is a change from A→T in the first position (base) of the amino acid at position 220 according to FIG. 3, especially wherein tyrosine is substituted for asparagine at amino acid position 220. The nucleic acid change can be detected by RsaI. In more general embodiments, the mutations include the genetic sequence alterations in the merlin gene, described in Example 6 herein, and which contribute to tumor formation and especially NF2.

In a further embodiment, the invention is directed to a method for treating a merlin-associated tumor in a patient, where the growth of such tumor reflects a functional change in merlin, a decreased level, or lack of merlin tumor suppressor activity in the tumor cell, the method comprising providing a functional merlin gene to the tumor cells of the patient, in a manner that permits the expression of the merlin protein provided by the gene, for a time and in a quantity sufficient to inhibit the growth of the tumor in the patient.

In a further embodiment, the invention is directed to a method of gene therapy of a symptomatic or presymptomatic patient, the method comprising providing a functional merlin gene to the relevant cells of the patient, both normal or tumor, in need of the therapy, in a manner that permits the expression of the merlin protein provided by the gene, for a time and in a quantity sufficient to provide the tumor suppressor function of merlin to the cells of the patient.

In a further embodiment, the invention is directed to a method for diagnosing NF2, the method comprising detecting a mutation in, or loss of, the merlin gene, or merlin protein, in a sample of non-tumor biological material from the subject to be diagnosed. This includes but is not limited to patients and single cells, such as embryonic cells or pre-natal cells from amniotic fluid. In a specific embodiment, the detection is of a mutant merlin protein encoded by a mutation of A T at the first position (base) of amino acid 220, especially where tyrosine has been substituted for asparagine at amino acid position 220, or of a mutated nucleotide coding sequence involving an A→T transversion at position the first base of amino acid 220, detectable by RsaI digestion. In a more general embodiment, the detection is of a mutant merlin protein encoded by DNA containing mutations including those described in Example 6 herein and which produce an altered merlin protein.

In a further embodiment, the invention is directed to a method for screening an individual for future likelihood of developing merlin-associated tumors, or the disease NF2, the method comprising detecting a mutation in, or loss of, the merlin gene, or merlin protein, in a sample of biological material from the individual. In a specific embodiment, the detection is of a mutant merlin protein encoded by a mutation of A→T at the first position (base) of amino acid 220, especially where tyrosine has been substituted for asparagine at amino acid position 220, or of a mutated nucleotide coding sequence involving an A→T transversion at the first base of amino acid 220, detectable by RsaI digestion. In more general embodiments, the detection is of a mutant merlin protein or mutant merlin DNA, wherein the mutation includes but is not limited to any of the mutations described herein, and that are clinically relevant.

In a further embodiment, the invention is directed to a method for treating NF2 in a patient, the method comprising providing a functional merlin gene to the desired cells of the patient, in a manner that permits the expression of the merlin protein provided by the gene, for a time and in a quantity sufficient to treat the patient.

In a preferred embodiment, a method is provided for identifying DNA sequence differences representing potential mutations within amplified coding sequences using single stranded conformational polymorphism analysis (SSCP). In this method, individual exons from the patient's DNA are first amplified by PCR. The amplification products are then denatured to separate the complementary strands and diluted to allow each single-stranded DNA molecule to assume a secondary structure conformation by folding on itself. Gel electrophoresis under non-denaturing conditions allows the detection of sequence changes compared to the normal (non-mutant) sequence.

In a further preferred embodiment, mutations discovered by application of the above method are used as standards of comparison for DNA from individuals suspected of being affected or known to be affected, so as to identify the mutation (if any) without full application of the above method. Knowledge of the exact mutation then allows the design of molecular therapeutic vehicles for gene therapy.

DETAILED DESCRIPTION OF THE PREFERRED EMBODIMENTS

In the following description, reference will be made to various methodologies known to those of skill in the art of molecular genetics and biology. Publications and other materials setting forth these known methodologies to which reference is made are incorporated herein by reference in their entireties as though set forth in full.

The "merlin" gene described herein is a gene found on human chromosome 22 that, as shown herein, contains non-overlapping and interstitial deletions in four independent NF2 patients and a single base change in affected individuals from five sibling pairs within an affected kindred; these results form the basis for concluding that this gene encodes a protein called "merlin," which possesses a tumor suppressor activity merlin has previously been termed "the NF2 tumor suppressor." The merlin gene, therefore, includes the DNA sequences shown in FIGS. 3 and 15A–Q herein and all functional equivalents. The gene includes not only the coding sequences, but all regulatory regions specifically controlling the expression of the merlin coding sequence, including promoter, enhancer, and terminator regions. In addition, introns and other DNA sequences which are spliced from the final merlin RNA transcript are also considered part of the merlin gene as encompassed herein. For example, the merlin gene encompasses the exonic and intronic sequences shown in FIGS. 15A–Q. Additionally, it is to be understood that the merlin gene includes the corresponding genetic and functional sequences in non-human animal species.

The merlin gene of the invention encodes a novel protein, merlin, that is related to the moesin-ezrin-radixin family of cytoskeleton-associated proteins (Gould, K. L. et al., *EMBO J.* 8:4133–4142 (1989); Turunen, O. et al., *J. Biol. Chem.* 264:16727–16732 (1989); Funayama, N. et al., *J. Cell Biol.* 115: 1039–1048 (1991); Lankes, W. T. et al., *Proc. Natl. Acad. Sci. U.S.A.* 88:8297–8301 (1991); Sato, N. et al., *J. Cell. Sci.* 103:131–143 (1992)). This protein, which is herein named "merlin" (moesin-ezrin-radixin-like protein), represents a new class of tumor suppressor whose function is mediated by interactions with the cytoskeleton. Merlin is found on human chromosome 22 between the known markers D22S1 and D22S28.

I. Cloning of Merlin DNA and Expression of Merlin Protein

The identification of merlin CDNA and protein as the mutated or missing gene in tumors from NF2 patients is exemplified below. In addition to utilizing the exemplified methods and results for the identification of additional mutations or deletions of the merlin gene in NF2 patients, and for the isolation of the native human merlin gene, the sequence information presented in FIGS. 3 and 15A–Q represents nucleic acid and protein sequences, that, when inserted into a linear or circular recombinant nucleic acid construct such as a vector, and used to transform a host cell, will provide copies of merlin DNA and merlin protein that are useful sources for the merlin DNA and merlin protein for the methods of the invention. Such methods are known in the art and are briefly outlined below.

The process for genetically engineering the merlin coding sequence, for expression under a desired promoter, is facilitated through the cloning of genetic sequences which are capable of encoding the merlin protein. These cloning technologies can utilize techniques known in the art for construction of a DNA sequence encoding the merlin protein, such as polymerase chain reaction technologies utilizing the merlin sequence disclosed herein to isolate the merlin gene de novo, or polynucleotide synthesis methods to construct the nucleotide sequence using chemical methods. Expression of the cloned merlin DNA provides merlin protein.

As used herein, the term "genetic sequences" is intended to refer to a nucleic acid molecule (preferably DNA). Genetic sequences that are capable of being operably linked to DNA encoding merlin protein, so as to provide for its expression and maintenance in a host cell, are obtained from a variety of sources, including commercial sources, genomic DNA, CDNA, synthetic DNA, and combinations thereof. Since the genetic code is universal, it is to be expected that any DNA encoding the merlin amino acid sequence of the invention will be useful to express merlin protein in any host, including prokaryotic (bacterial) and eukaryotic (plants, mammals (especially human), insects, yeast, and especially cultured cell populations).

If it is desired to select a gene encoding merlin de novo from a library that is thought to contain a merlin gene, the library can be screened and the desired gene sequence identified by any means which specifically selects for a sequence coding for the merlin gene or expressed merlin protein such as, a) by hybridization (under stringent conditions for DNA:DNA hybridization) with an appropriate merlin DNA probe(s) containing a sequence specific for the DNA of this protein, the sequence being that provided in FIG. 3 or a functional derivative thereof (that is, a shortened form that is of sufficient length to identify a clone containing the merlin gene), or b) by hybridization-selected translational analysis in which native merlin mRNA which hybridizes to the clone in question is translated in vitro and the translation products are further characterized for the presence of a biological activity of merlin, or, c) by immunoprecipitation of a translated merlin protein product from the host expressing the merlin protein.

When a human allele does not encode the identical sequence to that of FIGS. 3 or 15A–Q, it can be isolated and identified as being merlin DNA using the same techniques used herein. Many polymorphic probes useful in the fine localization of genes on chromosome 22 are known and available (see, for example, "ATCC/NIH Repository Catalogue of Human and Mouse DNA Probes and Libraries," fifth edition, 1991, pages 23–24; "Human gene mapping 10: tenth international workshop on human gene mapping," *Cytogenet. Cell Genet* 51:1–1148 (1989) and Rouleau, G. A. et al., "A genetic linkage map of the long arm of human chromosome 22," Genomics 4:1–6 (1989)).

A useful D22S1 probe is clone designation pMS3-18, a BglII-RFLP (allele 1: 8.2 kb; allele 2: 3.6 kb); as described in Fontaine, B. et al., *Ann. Neurol* 29:183–186 (1991) and Barker et al., *Cell* 36:131–138 (1984). An equivalent D22S1 probe, pEDF139, is available from the ATCC (ATCC 59688 and ATCC 59689).

Other useful probes include: D22S28 (clone W23C: ATCC 61636 and ATCC 61637); D22S15; D22S32 (plasmid pEZF31: ATCC 50274 and ATCC 59275); D22S42; D22S46; D22S56, LIF (the leukemia inhibitory factor gene); and NEFH (the neurofilament heavy chain gene).

Human chromosome 22-specific libraries are known in the art and available from the ATCC for the isolation of probes ("ATCC/NIH Repository Catalogue of Human and Mouse DNA Probes and Libraries," fifth edition, 1991, pages 72–73). Especially, LL22NS01, (ATCC 57714; Budarf et al., *Genomics* 10:996–1002 (1991)) is useful for these purposes (Frazer, K. A. et al., *Genomics* 14:574–584 (1992)).

It is not necessary to utilize the exact vector constructs exemplified in the invention; equivalent vectors can be constructed using techniques known in the art. For example, the sequence of the NEFH probe on plasmid pJL215 is published (see FIG. 3 in Lees, J. L. et al., EMBO J. 7:1947–1955 (1988)). Since it is this sequence that provides the specificity for the NEFH gene, it is only necessary that a desired probe contain this sequence, or a portion thereof sufficient to provide a positive indication of the presence of the NEFH gene.

Merlin genomic DNA may or may not include naturally occurring introns. Moreover, the genomic DNA can be obtained in association with the native merlin 5' promoter region of the gene sequences and/or with the native merlin 3' transcriptional termination region.

Merlin genomic DNA can also be obtained in association with the genetic sequences which encode the 5' non-translated region of the merlin mRNA and/or with the genetic sequences which encode the merlin 3' non-translated region. To the extent that a host cell can recognize the transcriptional and/or translational regulatory signals associated with the expression of merlin mRNA and protein, then the 5' and/or 3' non-transcribed regions of the native merlin gene, and/or, the 5' and/or 3' non-translated regions of the merlin mRNA can be retained and employed for transcriptional and translational regulation.

Genomic DNA can be extracted and purified from any host cell, especially a human host cell possessing the long arm of chromosome 22, by means well known in the art. Genomic DNA can be shortened by means known in the art, such as physical shearing or restriction enzyme digestion, to isolate the desired merlin gene from a chromosomal region that otherwise would contain more information than necessary for the utilization of the merlin gene in the hosts of the invention. For example, restriction digestion can be utilized to cleave the full-length sequence at a desired location. Alternatively, or in addition, nucleases that cleave from the 3'-end of a DNA molecule can be used to digest a certain sequence to a shortened form, the desired length then being identified and purified by polymerase chain reaction technologies, gel electrophoresis, and DNA sequencing. Such nucleases include, but are not limited to, Exonuclease III and Bal31. Other nucleases are well known in the art.

Alternatively, if it is known that a certain host cell population expresses merlin protein, then cDNA techniques known in the art can be utilized to synthesize a CDNA copy of the merlin mRNA present in such population.

For cloning the genomic or cDNA nucleic acid that encodes the amino acid sequence of the merlin protein into a vector, the DNA preparation can be ligated into an appropriate vector. The DNA sequence encoding merlin protein can be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and-ligation with appropriate ligases. Techniques for such manipulations are well known in the art.

When the merlin DNA coding sequence and an operably linked promoter are introduced into a recipient eukaryotic cell (preferably a human host cell) as a non-replicating, non-integrating, molecule, the expression of the encoded merlin protein can occur through the transient (nonstable) expression of the introduced sequence.

Preferably the coding sequence is introduced on a DNA molecule, such as a closed circular or linear molecule that is capable of autonomous replication. If integration into the host chromosome is desired, it is preferable to use a linear molecule. If stable maintenance of the merlin gene is desired on an extrachromosomal element, then it is preferable to use a circular plasmid form, with the appropriate plasmid element for autonomous replication in the desired host.

The desired gene construct, providing a gene coding for the merlin protein, and the necessary regulatory elements operably linked thereto, can be introduced into desired host cells by transformation, transfection, or any method capable of providing the construct to the host cell. A marker gene for the detection of a host cell that has accepted the merlin DNA can be on the same vector as the merlin DNA or on a separate construct for co-transformation with the merlin coding sequence construct into the host cell. The nature of the vector will depend on the host organism.

Suitable selection markers will depend upon the host cell. For example, the marker can provide biocide resistance, e.g., resistance to antibiotics, or heavy metals, such as copper, or the like.

Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species.

When it is desired to use *S. cerevisiae* as a host for a shuttle vector, preferred *S. cerevisiae* yeast plasmids include those containing the 2-micron circle, etc., or their derivatives. Such plasmids are well known in the art and are commercially available.

Oligonucleotide probes specific for the merlin sequence can be used to identify clones to merlin and can be designed de novo from the knowledge of the amino acid sequence of the protein as provided herein in FIG. 3 or from the knowledge of the nucleic acid sequence of the DNA encoding such protein as provided herein in FIGS. 3 and 15A–15Q or of a related protein. Alternatively, antibodies can be raised against the merlin protein and used to identify the presence of unique protein determinants in transformants that express the desired cloned protein.

A nucleic acid molecule, such as DNA, is said to be "capable of expressing" a merlin protein if that nucleic acid contains expression control sequences which contain transcriptional regulatory information and such sequences are "operably linked" to the merlin nucleotide sequence which encode the merlin polypeptide.

An operable linkage is a linkage in which a sequence is connected to a regulatory sequence (or sequences) in such a way as to place expression of the sequence under the influence or control of the regulatory sequence. If the two DNA sequences are a coding sequence and a promoter region sequence linked to the 5' end of the coding sequence, they are operably linked if induction of promoter function results in the transcription of mRNA encoding the desired protein and if the nature of the linkage between the two DNA sequences does not (1) result in the introduction of a frame-shift mutation, (2) interfere with the ability of the expression regulatory sequences to direct the expression of the protein, antisense RNA, or (3) interfere with the ability of the DNA template to be transcribed. Thus, a promoter region is operably linked to a DNA sequence if the promoter is capable of effecting transcription of that DNA sequence.

The precise nature of the regulatory regions needed for gene expression can vary between species or cell types, but includes, as necessary, 5' non-transcribing and 5' non-translating (non-coding) sequences involved with initiation of transcription and translation respectively, such as the TATA box, capping sequence, CAAT sequence, and the like, with those elements necessary for the promoter sequence being provided by the promoters of the invention. Such transcriptional control sequences can also include enhancer sequences or upstream activator sequences, as desired.

The vectors of the invention can further comprise other operably linked regulatory elements such as DNA elements which confer antibiotic resistance, or origins of replication for maintenance of the vector in one or more host cells.

In another embodiment, especially for maintenance of the vectors of the invention in prokaryotic cells, or in yeast *S. cerevisiae* cells, the introduced sequence is incorporated into a plasmid or viral vector capable of autonomous replication in the recipient host. Any of a wide variety of vectors can be employed for this purpose. En Bacillus hosts, integration of the desired DNA may be necessary.

Expression of a protein in eukaryotic hosts such as a human cell requires the use of regulatory regions functional in such hosts. A wide variety of transcriptional and translational regulatory sequences can be employed, depending upon the nature of the host. Preferably, these regulatory signals are associated in their native state with a particular gene which is capable of a high level of expression in the specific host cell, such as a specific human tissue type. In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell.

If desired, the non-transcribed and/or non-translated regions 3' to the sequence coding for the merlin protein can be obtained by the above-described cloning methods. The 3'-non-transcribed region of the native human merlin gene can be retained for its transcriptional termination regulatory sequence elements, or for those elements which direct polyadenylation in eukaryotic cells. Where the native expression control sequences signals do not function satisfactorily in a host cell, sequences functional in the host cell can be substituted.

It may be desired to construct a fusion product that contains a partial coding sequence (usually at the amino terminal end) of a first protein or small peptide and a second coding sequence (partial or complete) of the merlin protein at the carboxyl end. The coding sequence of the first protein can, for example, function as a signal sequence for secretion of the merlin protein from the host cell. Such first protein can also provide for tissue targeting or localization of the merlin protein if it is to be made in one cell type in a multicellular organism and delivered to another cell type in the same organism. Such fusion protein sequences can be designed with or without specific protease sites such that a desired peptide sequence is amenable to subsequent removal.

The expressed merlin protein can be isolated and purified from the medium of the host in accordance with conventional conditions, such as extraction, precipitation, chromatography, affinity chromatography, electrophoresis, or the like. For example, affinity purification with anti-merlin antibody can be used. A protein having the amino acid sequence shown in FIG. 3 can be made, or a shortened peptide of this sequence can be made, and used to raised antibodies using methods well known in the art. These antibodies can be used to affinity purify or quantitate merlin protein from any desired source.

If it is necessary to extract merlin protein from the intracellular regions of the host cells, the host cells can be collected by centrifugation, or with suitable buffers, lysed, and the protein isolated by column chromatography, for example, on DEAE-cellulose, phosphocellulose, polyribocytidylic acid-agarose, hydroxyapatite or by electrophoresis or immunoprecipitation.

It is to be understood that all of the above procedures that are applicable to cloning and expressing merlin sequences apply equally to normal and mutant sequences. Mutations may be in any of the regions, i.e., coding, non-coding, exonic, intronic, regulatory and the like.

II. Characterization of Mutations in an Affected Individual

The definition of the sequence alteration predicted to change the sequence of the merlin protein in the extended NF2 family originally employed to map the genetic defect on chromosome 22 is exemplified below (Wertelecki, W. et al., *New Engl. J. Med.* 319:278–283 (1988); Narod, S. A. et al., *Am. J. Hum. Genet.* 51:486–496 (1992)). The characterization of this mutation allows the early detection of the disorder in "at risk" family members before clinical symptoms appear. Although the exemplary material is directed to the detection of the disorder in a specific kindred, the exemplary methods can be applied to any family to define the precise molecular lesion underlying NF2, and this information can then be used to accurately determine whether at-risk members of the family have inherited the disorder.

Further, this information can be used to assess any given individual for the merlin genotype in that individual. Therefore, affected or other (e.g., carrier) individuals can be assayed for the presence of new mutations as well as for the presence of mutations that are previously defined. Accordingly, the exemplary material shows a preferred approach to isolating and characterizing the mutations associated with NF2 or other Merlin-dependent pathologies.

New mutations in any desired kindred or affected individual or individual suspected of being affected can be defined using single-strand conformational polymorphism (SSCP) and sequence analysis of DNA amplified from the NF2 gene merlin. DNA alterations in the merlin coding sequence cause a shift on SSCP gels that is characteristic of the disease chromosome being transmitted with the disorder and present in only affected members of the pedigree. For example, as described below, an A→T transversion causes substitution of a tyrosine for an asparagine at position 220 of the merlin protein, in a region highly conserved in closely related members of the family of cytoskeletal-associated proteins. This alteration caused a shift on SSCP gels that was characteristic of the disease chromosome in this NF2 pedigree, being transmitted with the disorder, present only in affected members of the pedigree, absent in unaffected members of the family and absent from 158 unrelated individuals. Because of this identification, it is now possible to significantly alter the management of "at risk" members of this extended kindred, based on a precise definition of which individuals carry the disease gene, and which have escaped inheritance of the defect. A similar approach is applicable to defining the underlying lesion/DNA defect and thereby improving presymptomatic or prenatal diagnosis in any other NF2 family that does not have this specific mutation. As shown below in the exemplary material, an array of various mutations have been associated with the merlin locus. Accordingly, any of these relevant mutations may be used for purposes of diagnosis in specific kindreds or individuals.

Accordingly, a combination of amplification, for example using the polymerase chain reaction (PCR) with SSCP, permits the identification of other mutations in a merlin gene as simple as single base changes. Any regions of the merlin gene can be assessed by this procedure: The sequence now made available by the inventors allows the design of primers and amplification of any desired region including coding, intronic, and regulatory non-coding or non-transcribed.

The SSCP technique uses strategically placed primer sets to amplify small regions of the NF2 gene directly from genomic DNA using PCR. The double-stranded PCR product containing the amplified region can then be used as a template to generate single strands by priming multiple rounds of DNA synthesis with one of the oligonucleotides previously used in a double strand reaction. The amplified products can be used for SSCP analysis, cloned, and sequenced.

The amplification products, denatured to separate the complementary DNA strands, are diluted to allow each single-stranded DNA molecule to assume a secondary structure conformation by folding on itself. The single-stranded molecules are then subjected to electrophoresis, for example by polyacrylamide, under non-denaturing conditions. The secondary structure, which is highly dependent on the precise DNA sequence, affects mobility of the strand on the gel. Even a single base change or deletion can produce a visible shift in the final band position on the gel. Altered SSCP patterns thus can be analyzed based on a comparison with the SSCP patterns from affected family members, unrelated individuals, sporadic tumors, et cetera. The altered SSCP fragment pattern can then be correlated with inheritance of the disorder and associated with affected members of the pedigree.

Following SSCP analysis, the precise DNA alteration that causes the shifting mobility pattern can be ascertained by direct DNA sequencing of the PCR amplification product from which the altered single-stranded molecule was derived.

After a specific mutation is confirmed following PCR and SSCP analysis and direct sequencing, the presence of this mutation can be rapidly confirmed for any desired member of the kindred or otherwise by performing the same type of analysis.

Alternatively, an approach may be taken exploiting restriction enzyme digestion following PCR amplification in the area of the defined mutation. If the defined mutation creates a new restriction site, the presence of this mutation can be rapidly confirmed in other members of the kindred or otherwise by using primers in the area of mutation to amplify sequences that include the mutation and which, when subjected to restriction enzyme digestion, create restriction fragments that are specific to affected individuals and absent in non-affected individuals. Thus, following PCR, the fragments from affected individuals may be subjected to electrophoresis and merely stained by ethidium bromide without the resort to cumbersome radiolabeling or other labeling techniques.

In a specific disclosed embodiment, the genomic DNA of patients and unaffected control individuals was amplified using primers in the intron flanking exon 7. SSCP analysis was then performed. The amplified products were also cloned and sequenced. Intron DNA sequence flanking each exon was determined. DNA primers that permit amplification of the exon sequences from genomic DNA using PCR were developed. A mobility shift was detected in the amplification products of exon 7 comprising base pair 819 to 894 of the merlin coding sequence. DNA sequencing was used to confirm the precise DNA alteration that caused the shifted mobility pattern in the SSCP analysis.

Normal merlin DNA displays an AAC codon encoding asparagine at position 220 of the merlin protein. The DNA with the shifted mobility reveals both an A and a T residue at the first position of this codon, suggesting a normal AAC codon on one chromosome and a mutated TAC on the other. The TAC would substitute a tyrosine at position 220.

The sequence change created a GTAC stretch that can be recognized by the restriction endonuclease RsaI. The site created nine base pairs 3' to a preexisting RsaI site in this exon. Rsa digests on the amplified PCR product confirm the presence of the same DNA change in other affected members of the family, its cotransmission with NF2, and its absence in unaffected members of the pedigree. Unaffected members display two RsaI fragments of 96 base pairs and 76 base pairs, whereas the affected individuals produce an additional third fragment of 67 base pairs generated from the Rsa site created by the A→T change at codon 220.

Accordingly, in one embodiment of the invention, this specific mutation could be identified in individuals having or suspected of having NF2 by simple assays, e.g., Southern blots, involving restriction enzyme digestion with RsaI. Similarly, if mutations in merlin create or abolish other restriction enzyme sites, this alteration can be exploited to recognize the mutation in individuals other than the one in whom the mutation was discovered by restriction enzyme cleavage assays.

In specific embodiments of the invention, SSCP analysis was performed to scan all seventeen exons of the entire merlin gene for mutations. In schwannomas from NF2 patients, base changes, deletions, and insertions were observed at various locations which resulted in missense, frameshift, and possible splice donor and splice acceptor alterations. The NF2 gene was also examined in sporadic schwannomas. Deletions, base changes, and insertions were observed in various locations in both intron and exon sequences. These mutations created frameshift, nonsense, and missense mutations, as well as actual or presumed alterations in the splice acceptor site, splice donor site, or acceptor branch site. Accordingly, in specific embodiments of the invention, these mutations may be useful as standards of comparison for the examination of at-risk individuals.

III. Use of Merlin for Diagnostic and Treatment Purposes

It is to be understood that although the following discussion is specifically directed to human patients, the teachings are also applicable to any animal that expresses merlin and in which loss or mutation of merlin leads to pathological manifestations as in the human patient.

It is also to be understood that the methods referred to herein are applicable to any merlin-associated tumor or subject suspected of developing or having such a tumor, whether such tumor is sporadic or associated with a condition such as NF2.

A "merlin-associated" tumor is a tumor characterized in that the growth of such tumor reflects a decrease, functional alteration, or lack of merlin activity, especially if the decrease, change, or lack of merlin activity reflects a mutation or loss of the Merlin gene or its regulatory regions. An example of such a tumor would include, but is not limited to, a schwannoma, (such as, for example, a vestibular schwannoma, and especially a bilateral vestibular schwannoma, a schwannoma of a cranial nerve, especially on the vestibular branch of the eighth cranial nerve, or a schwannoma of a spinal nerve root), or a meningioma (such as, for example, a meningioma of a cranial nerve, a vestibular meningioma, or a meningioma of a spinal nerve root).

The diagnostic and screening methods of the invention are especially useful for a person suspected of being at risk for developing merlin-associated tumor or disease and/or NF2 based on family history, or a person in which it is desired to diagnose or eliminate the presence of a merlin-associated condition or tumor or the NF2 condition as a causative agent behind a tumor growth.

By "predisposition to develop a merlin-associated tumor" is intended a genotype wherein a subject has the tendency to develop a genotype leading to the expression of an aberrant merlin gene. This could involve a subject heterozygous for a merlin mutation who subsequently becomes homozygous for the mutation such that the mutation is now expressed. Such a predisposition can be detected by molecular assays capable of detecting mutations or molecular changes in DNA, RNA, or merlin protein. Thus, even though a subject may be heterozygous for the merlin mutation, the mutation, if expressed on the affected chromosome, could then be detected, or, alternatively, the mutation in the aberrant chromosome could be directly detected at the nucleic acid level.

Patients suspected of having NF2 will generally first present with a diagnosis of NF2 made according to the criteria set forward by the National Institutes of Health Consensus Development Conference on Neurofibromatosis (*Arch. Neurol.* 45:575–578 (1988); Mulvihill, J. J. et al., *Ann. Intern. Med.* 113:39–52 (1990). Specifically, for NF2, the NIHCDCN diagnostic criteria are met if a person has either of the following:

1) Bilateral eighth nerve masses seen with appropriate imaging techniques (for example, computerized tomographic or magnetic resonance imaging);

2) A first-degree relative with NF2 and either unilateral eighth nerve mass or two of the following: neurofibroma, meningioma, glioma, schwannoma, and juvenile posterior subcapsular lenticular opacity.

According to the invention, presymptomatic screening of an individual in need of such screening is now possible using DNA encoding the merlin protein of the invention, and specifically, DNA having the sequence of the native human merlin gene. The screening method of the invention allows a presymptomatic diagnosis, including prenatal diagnosis, of the presence of a missing or aberrant merlin gene in individuals, and thus an opinion concerning the likelihood that such individual would develop or has developed merlin-associated tumors and/or NF2. This is especially valuable for the identification of carriers of altered or missing merlin genes, for example, from individuals with a family history of merlin-associated tumors and/or NF2. This is also especially valuable for those patients where the chances of hearing preservation are optimal with early microsurgical removal of a vestibular schwannoma. Early diagnosis is also desired to maximize appropriate timely intervention as to any expected sequelae of the patient's tumor growth and lens opacities.

For example, in the method of screening, a tissue sample would be taken from such individual, and screened for (1) the presence of the 'normal' human merlin gene; (2) the presence of merlin mRNA and/or (3) the presence of merlin protein. The normal human gene can be characterized based upon, for example, detection of restriction digestion patterns in 'normal' versus the patient's DNA, including RFLP analysis, using DNA probes prepared against the merlin sequence (or a functional fragment thereof) taught in the invention. Similarly, merlin mRNA can be characterized and compared to normal merlin mRNA (a) levels and/or (b) size as found in a human population not at risk of developing merlin-associated tumors and/or NF2 using similar probes. Lastly, merlin protein can be (a) detected and/or (b) quantitated using a biological assay for merlin activity (its ability to suppress tumor growth) or using an immunological assay and anti-merlin antibodies. When assaying merlin protein, the immunological assay is preferred for its speed.

An (1) aberrant merlin DNA size pattern or sequence, and/or (2) aberrant Merlin mRNA size, level, or sequence, and/or (3) aberrant merlin protein or level thereof would indicate that the patient is at risk for developing a merlin-associated tumor and/or NF2 and is likely to develop a merlin-associated tumor and/or NF2.

Similarly, if the tissue sample was derived from a tumor taken from a patient suspected of having a merlin-associated tumor and/or NF2, then (1) aberrant merlin DNA size, pattern, or sequence, and/or (2) aberrant merlin mRNA size, sequence, or level and/or (3) aberrant merlin protein or levels thereof would indicate that the patient has developed a merlin-associated tumor and/or NF2. These tumors can be treated with the methods of the invention as described below.

In accordance with the inventors' characterization of a specific merlin mutation in a particular kindred, and the guidance provided to extend the knowledge and approaches disclosed herein to the identification of other mutations and the identification of the mutation disclosed herein in other kindreds, preferred methods of screening tissue samples from presymptomatic, asymptomatic, or symptomatic individuals involve, rather than comparison with normal merlin protein, DNA, or RNA, direct detection of abnormal merlin genes and gene products.

Accordingly, a preferred strategy for identifying DNA sequences representing potential mutations within amplified coding sequences is the use of SSCP analysis combined with amplification and DNA sequencing. Accordingly, screening individual exons from a subject's DNA that have been amplified by PCR is a first approach. SSCP followed by direct DNA sequencing is then performed. In more preferred embodiments, mutations previously identified using this protocol provide a standard for comparison of the tissue sample to be assayed. The sample is thus amplified using primers known to be adjacent to the mutation and the amplification product either subjected to SSCP or subjected to restriction enzyme analysis in the case wherein the mutation creates or abolishes restriction sites found in the normal merlin gene.

Similarly, mutant mRNAs may also be the basis for assay of a subject's RNA in Northern blots where the abnormal RNA has a characteristic pattern as in electrophoresis. Alternatively, CDNA transcripts from the RNA of a subject can be analyzed by comparing such transcripts to the transcripts from known mutant merlin genes.

Alternatively, aberrant merlin proteins with characterized mutations may serve as the basis for comparison with proteins derived from the individual undergoing the diagnostic treatment. Thus, recognition by monoclonal or polyclonal antibodies using standard immunological assays may reveal the presence of mutated proteins that can be identified by comparison with previous mutations. Alternatively, methods of identifying mutant proteins using known mutants as comparisons include, but are not limited to, tryptic peptide digests.

Accordingly, a repository of mutant DNA, RNA/cDNA and protein patterns gathered from an analysis of the NF2 mutations from various kindreds may serve as standards for rapid and accurate identification of affected cells or individuals.

The screening and diagnostic methods of the invention do not require that the entire merlin DNA coding sequence be used as a probe. Rather, it is only necessary to use a fragment or length of nucleic acid that is sufficient to detect the presence of the merlin gene in a DNA preparation from a normal or affected individual, the absence of such gene, or an altered physical property of such gene (such as a change in electrophoretic migration pattern).

Prenatal diagnosis can be performed when desired, using any known method to obtain fetal cells, including amniocentesis, chorionic villous sampling, and fetoscopy. Prenatal chromosome analysis can be used to determine if the portion of chromosome 22 possessing the normal merlin gene is present in a heterozygous state.

The merlin DNA can be synthesized, and, if desired, labeled with a radioactive or nonradioactive reporter group, using techniques known in the art (for example, see Eckstein, F., ed., *Oligonucleotides and Analogues: A Practical Approach,* IRS Press at Oxford University Press, New York, 1992); and Kricka, L. J., ed., Nonisotopic DNA Probe Techniques, Academic Press, San Diego, (1992)).

Although the method is specifically described for DNA—DNA probes, it is to be understood that RNA possessing the same sequence information as the DNA of the invention can be used when desired.

In the method of treating NF2 in a patient in need of such treatment, functional merlin DNA is provided to the cells of such patient, especially the tumor cells, in a manner and amount that permits the expression of the merlin protein provided by such gene, for a time and in a quantity sufficient to treat such patient. Many vector systems are known in the art to provide such delivery to human patients in need of a gene or protein missing from the cell, For example, retrovirus systems can be used, especially modified retrovirus systems and especially herpes-simplex virus systems, such as those described in U.S. application Ser. No. 07/913,977 (filed Jul. 16, 1992); U.S. application Ser. No. 07/956,949 (filed Oct. 6, 1992), U.S. application Ser. No. 07/895,364 (filed Jun. 9, 1992); each incorporated herein fully by reference. In addition, such methods are provided for, in, for example, the teachings of Breakefield, X. A. et al., *The New Biologist* 3:203–218 (1991); Huang, Q. et al., *Experimental Neurology* 115:303–316 (1992), WO93/03743 and WO90/09441 each incorporated herein fully by reference.

Delivery of a DNA sequence encoding a functional merlin protein, such as the amino acid encoding sequence of FIGS. 3 and 15A–15Q, will effectively replace the missing or mutated merlin gene of the invention, and inhibit, and/or stop and/or regress tumor growth that arose due to the loss of the merlin tumor suppressor.

This method is especially effective in the tumor types such as those classically associated with NF2, and especially with a schwannoma, (such as, for example, a bilateral vestibular schwannoma, a schwannoma of a cranial nerve, especially on the vestibular branch of the eighth cranial nerve, or a schwannoma of a spinal nerve root), meningiomas (such as, for example, a meningioma of a cranial nerve, a vestibular meningioma, or a meningioma of a spinal nerve root).

The method of the invention is also useful to treat conditions such as posterior capsular lens opacities, deafness, balance disorder, paralysis or other neurological problem when such problem is due to the presence of a merlin-associated tumor or NF2 condition.

The manner and method of carrying out the present invention can be more fully understood by those of skill by reference to the following examples, which examples are not intended in any manner to limit the scope of the present invention or of the claims directed thereto.

EXAMPLES

Experimental Procedure for Examples 1–4
NF2 Cell Lines

Lymphoblast cell lines were established (Anderson, M. A. et al., *In Vitro* 20:856–858 (1984)) from affected members of NF2 pedigrees and from their unaffected relatives. Diagnosis of NF2 conformed to the criteria set forward by the National Institutes of Health Consensus Development Conference on Neurofibromatosis (Mulvihill, J. J. et al., *Ann. Intern. Med.* 113:39–52 (1990)), except for the patient whose meningioma displayed a 4 bp deletion. This patient had a right vestibular schwannoma, and multiple meningiomas. Although she did not have a history of NIF2, she probably represents a new mutation. Primary meningioma cells were cultured as described (Logan, J. A. et al., *Cancer Genet. Cytogenet.* 45:41–47 (1990)) and analyzed after less than five passages.

Somatic cell hybrids were prepared by fusing GUS5069 lymphoblasts with a Chinese hamster cell line deficient in HPRT activity (CHTG49); Athwall, R. S. et al., *Proc. Natl. Acad. Sci. U.S.A.* 74:2943–2947 (1977)) using GIBCO PEG 4,000. Fused cell lines were selected by their ability to grow in media containing hypoxanthine, aminopterin and thymidine (HAT). Hybrids were screened for the chromosome 22 homologues using the polymorphic SSR marker, TOP1P2 (Trofatter, J. A. et al., *Hum. Mol. Genet.* 1:455 (1992)). Control hybrids GM10888 and Eye3FA6 (NA10027) are described in the listing the NIGMS Human Genetic Mutant Cell Repository collection (Coriell Institute, Camden, N.J.).
DNA/RNA Blotting DNA was prepared from cultured cells and DNA blots prepared and hybridized as described (Gusella, J. F. et al., *Proc. Natl. Acad. Sci. U.S.A.* 76:5239–5243 (1979); Gusella, J. F. et al., *Nature* 306:234–238 (1983)). For pulsed-field gel analysis, agarose DNA plug preparation, and electrophoresis were carried out as described (Bucan, M. et al., *Genomics* 6:1–15 (1990)). RNA was prepared and Northern blotting performed as described in Buckler et al. Buckler, A. J. et al., *Proc. Natl. Acad. Sci. U.S.A.* 88:4005–4009 (1991).

Cosmid Walking

The NEFH probe used for blot analysis and to initiate cosmid walking was pJL215, representing a 4.4 kb KpnI/XbaI genomic fragment containing exon 4 and 3'UTR (Lees, J. F. et al., *EMBO J.* 7:1947–1955 (1988)). The NEFH probe pJL215 was obtained from Dr. Greg Elder and Dr. Robert Lazzarini, The Laboratory of Molecular Genetics, National Institute of Neurological and Communicative Disorders and Stroke, National Institutes of Health, Bethesda, Md., 29892. Cosmid walking was performed in an arrayed cosmid library prepared from DNA of flow-sorted human chromosome 22 (LL22NC03); Dr. Pieter DeJong, Lawrence Livermore National Laboratory). Cosmid overlaps were identified by either hybridization of whole cosmid DNA or isolated fragments to filter replicas of the gridded arrays, or by PCR screening of row and column DNA pools. STSs were developed by direct cosmid sequencing using the T3 or T7 end-primers (McClatchey, A. I. et al., *Hum. Mol. Genet.* 1:521–527 (1992)).

cDNA Isolation and Characterization

Human frontal cortex and hippocampus cDNA libraries in lambdaZAPII (Stratagene) were screened using exon probes isolated and prepared as described by Buckler et al. (Buckler, A. J. et al., *Proc. Natl. Acad. Sci. U.S.A.* 88:4005–4009 (1991)). cDNA clones and trapped exon were sequenced as described (Sanger, T. et al., *Proc. Natl. Acad. Sci. U.S.A.* 74:5463–5467 (1977)). Direct PCR sequencing was performed as described (McClatchey, A. I. et al., *Cell* 68:769–774 (1992)). Screening for variations by SSCP analysis followed the procedure described in Ambrose et al. (Ambrose, G. et al., *Hum. Mol. Genet.* 1:697–703 (1992)). RNA was reverse transcribed using an oligo(dT) primer (BRL reverse transcriptase) to prepare first strand cDNA. Portions of the cDNA were amplified using the following primer sets:

5'CCAGCCAGCTCCCTATGGATG3' [SEQ ID No: 11] and

5'AGCTGAAATGGAATATCTGAAG3' [SEQ ID No: 12]

to amplify bp 824–2100 and

5'GCCTTCTCCTCCCTGGCCTG3' [SEQ ID No: 13] and

5'GATGGAGTTCAATTGCGAGATG3' [SEQ ID No: 14]

to amplify bp 314–1207. These cold PCR products were then reamplified with specific regional primers for SSCP as described in the legend to FIGS. 6, 6A and 6B.

Example 1

Scanning the NF2 Candidate Region for Rearrangement

The region on chromosome 22 that was examined for the presence of the NF2 gene was between D22S1 and D22S28; this region was estimated to encompass 6 Mb of band q12 (Frazer, K. A. et al., *Genomics* 14:574–584 (1992)).

By scanning the human chromosome 22 region between D22S1 and D22S28 for loss of DNA it was determined whether some germline NF2 mutations might involve a deletion of the tumor suppressor gene as has been found in Wilms' tumor and retinoblastoma (Riccardi, V. M. et al., *Pediatrics* 61:604–610 (1978); Francke, U. et al., *Cytogenet. Cell Genet.* 24:185–192 (1979); Dryja, T. P. et al., *Proc. Natl. Acad. Sci. U.S.A.* 83:7391–7394 (1986)). Pulsed-field gel blots containing lymphoblast DNA from various NF2 patients were probed for several loci in the candidate region, including D2251, D22515, D22S28, D22S32, D22S42, D22S46, D22S56, LIF (the leukemia inhibitory factor gene) and NEFH (the neurofilament heavy chain gene). This analysis revealed that in a lymphoblast cell line (GUS5069) derived from a female NF2 patient, a probe for the NEFH locus hybridized to apparently altered fragments of reduced size with both NotI and NruI.

Figure 1:
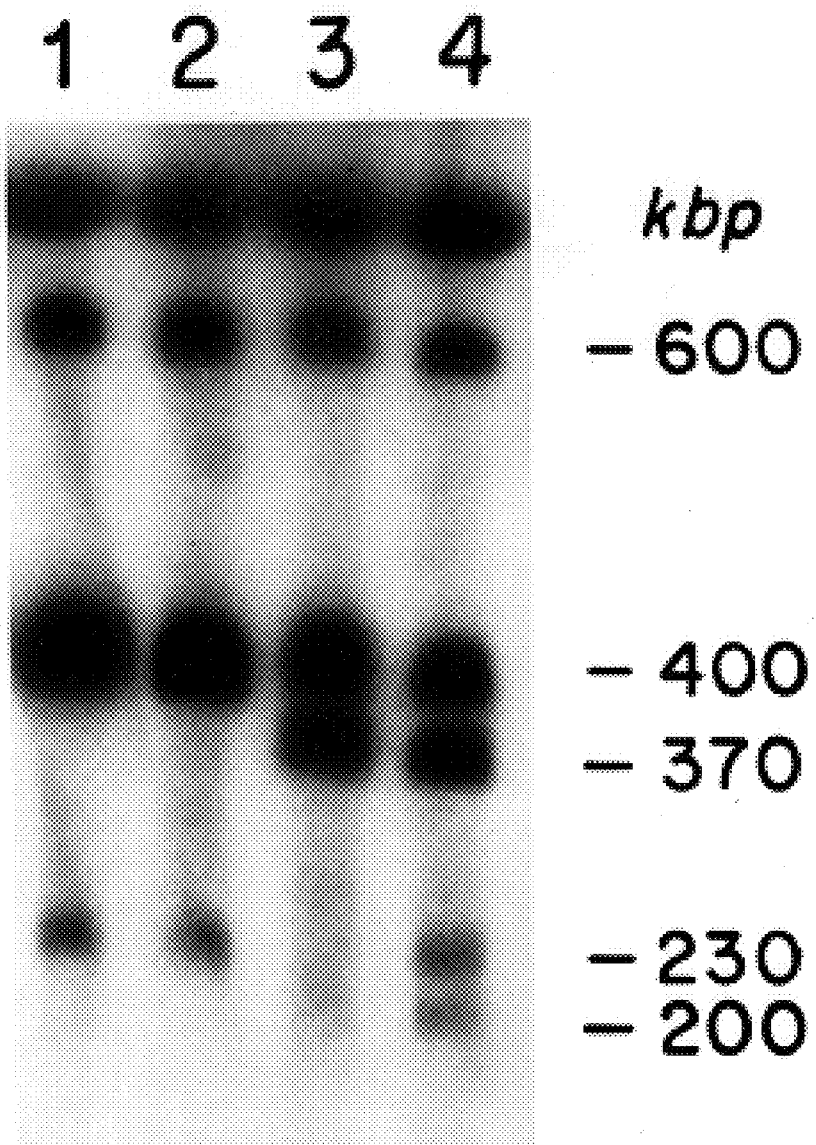
FIG. 1. Pulsed-field gel analysis of lymphoblast DNA from NF2 patients. DNA in agarose blocks was digested with NotI, subjected to electrophoresis, blotted, and hybridized to a radiolabeled 4 kbp NEFH probe. Lane 1, GUS6274 (affected NF2 unrelated to lanes 3 and 4); lane 2, GUS7870 (normal human); lane 3, GUS5068 (affected daughter); lane 4, GUS5069 (affected mother).

In NotI-digested DNA (FIG. 1), the NEFH probe detected fragments of approximately 600 kb, 400 kb and 230 kb in most lymphoblast cell lines. It was not possible to confirm that the 600 kb fragment originated from chromosome 22. Thus, it was possible that hybridization had occurred with a related locus (Menon et al., unpublished results). Variable intensity of the 230 kb fragment in many samples suggested that it resulted from partial digestion of the 400 kb fragment. In GUS5069, additional fragments of approximately 370 kb and 200 kb were observed. These results are consistent with the possibility of a deletion within the region common to the 400 kb and 230 kb fragments. The alteration was transmitted along with NF2 from the patient to her affected daughter (represented by GUS5068) (FIG. 1).

Example 2

Chromosome Walking Toward the Merlin Gene

To isolate DNA corresponding to the region of chromosome 22 apparently deleted in GUS5069, a bi-directional cosmid walk was initiated from NEFH. At each step, single restriction fragments of the cosmids were used as probes on pulsed-field gels to establish the location of the putative deletion relative to NEFH. On the 5' side of NEFH, a NotI site that was rarely cleaved in lymphoblast DNA was identified. Probes beyond the NotI site detected the same approximately 400 kb NotI fragment along with a 170 kb fragment of variable intensity. Thus, infrequent cleavage of this NotI site divides the 400 kb fragment into fragments of 230 kb and 170 kb. Since the putative deletion in GUS5069 affects the 230 kb fragment but not the 170 kb fragment, further experiments continued to walk only 3' of NEFH. Pulsed-field gel blots containing DNA from GUS5069 were again probed.

Figure 2:
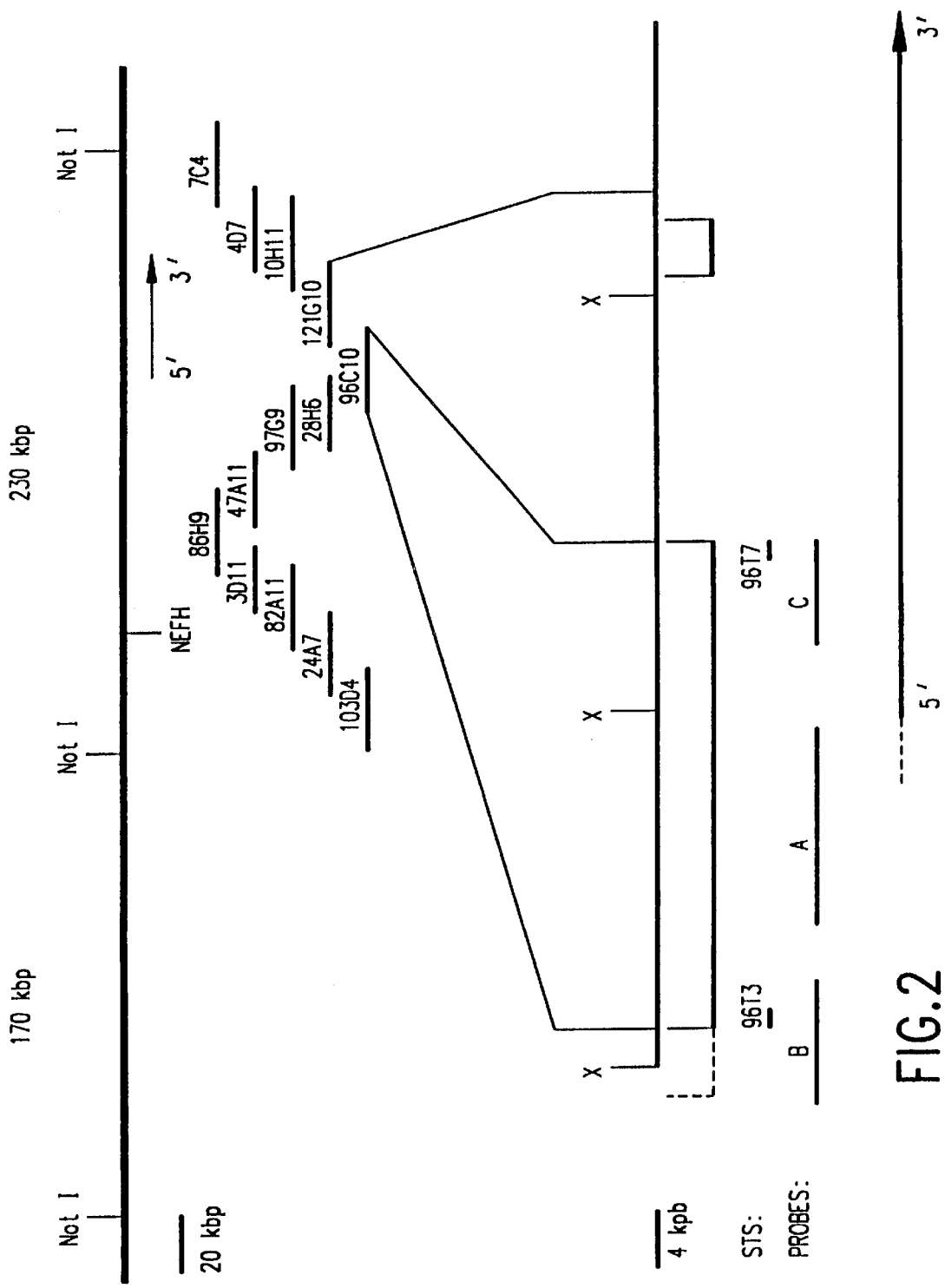
FIG. 2. Physical map of chromosome 22 region surrounding the NF2 deletions. NotI sites were determined by pulsed-field gel analysis and confirmed in cosmids. Cosmids were named according to their standardized library coordinates. The enlarged region shows details of the merlin gene vicinity with deleted regions denoted by underlying brackets. Probes used in deletion analysis: A, 14 kbp HindIII fragment from cosmid 96C10; B, 8.5 kbp HindIII fragment from 28H6 that spans the T3 end of 96C10; C, 8 kbp HindIII end-fragment from the T7 end of 96C10; 96T3 (primer pair.

The NotI pulsed-field gel map and a minimal set of clones representing the cosmid walk and the extent of the genomic deletion (see FIG. 5A) are shown in FIG. 2. The deletion was reached when a probe (FIG. 2, Probe A) was tested from cosmid 96C10 which failed to detect the altered NotI fragment in GUS5069. However, various probes from cosmid 28H6 and 121G10 did detect the altered fragment.

To estimate the extent of deletion, probes B and C (FIG. 2) were tested. Probe B is an 8 kb HindIII fragment from 28H6 which overlaps with the T3 end of 96C10. Probe C is a 9 kb HindIII fragment from the T7 end of 96C10. Probe B detected both the normal and the altered NotI PFG fragment, but probe C detected only the normal fragment.

For more precise analysis of the deletion, the altered chromosome 22 from GUS5069 was segregated from its normal counterpart in human X hamster somatic cell hybrids. STS assays for the T3 and T7 ends of 96C10 were created and hybrids containing the separated chromosomes 22 were tested. In contrast to the above hybridization results, the T3 end of 96C10 was absent in hybrid GUSH134A3, containing the deleted chromosome but present in GUSH134A10 containing the normal chromosome. Moreover, the T7 assay was positive in both hybrids. The locations of probes B and C, and of both STS assays were confirmed on the cosmid walk. Thus, the failure of probe C to detect the altered fragment suggests that the deletion spans most but not all of this sequence. Similarly, the other deletion breakpoint must occur within the region spanned by probe B. Therefore, the results of hybridization and PCR indicate that the deletion must encompass almost all of 96C10 and up to an additional 5 kb of 28H6. This 35–45 kb region is expanded below the cosmid walk in FIG. 2.

Example 3
Identification and Characterization of the Merlin cDNA

Exon amplification (Buckler, A. J. et al., *Proc. Natl. Acad. Sci. U.S.A.* 88:4005–4009 (1991)), which produces cloned "trapped exons," was applied to cosmids 28H6, 96C10, 121G10, 123F5, 10H11, and 7C4 surrounding the site of the NF2 deletion as a rapid method of obtaining exonic probes for cDNA cloning. Each exon clone can represent a single exon, or multiple exons spliced together in the trapping procedure. Twenty-four exon clones were obtained and sequenced, 6 of which displayed sequence similarity with the cytoskeleton-associated proteins moesin, ezrin and radixin (see below). The latter exons were used to screen human frontal cortex and hippocampus cDNA libraries.

FIG. 3 shows the complete DNA sequence of JJR-1, the longest clone obtained in cDNA screening. JJR-1 has been deposited with the American Type Culture Collection, 12301 Parklawn Drive, Rockville, Md. 20852 on Jul. 28, 1993 and assigned ATCC75509. This sequence contains eight of the cloned exon segments as shown in FIG. 5. The CDNA is 2,257 bp long and shows no evidence of a poly(A) tail. However, two shorter CDNA clones, JJR-6 and JJR-9, which overlapped the restriction map of JJR-1, had apparent poly(A) tails beginning at base 2231. JJR-1 contains an open reading frame of 1785 bp, encoding a predicted protein of 69 kD. There is one in-frame stop codon within 90 bp upstream of the putative initiator methionine. The JJR-1 cDNA spans at least 50 kb of genomic DNA, and is transcribed in the same orientation as NEFH as shown by the arrows in FIG. 2.

Both the JJR-1 DNA sequence and the predicted protein product were used to search for similarity in nucleic acid and protein databases using the BLAST network service of the National Center for Biotechnology Information (Altschul, S. F. et al., *J. Mol. Biol.* 215:403–410 (1990)). The DNA sequence displayed significant similarity to moesin and ezrin genes from several species, including man ($P=9.0e^{-125}$ and $9.0e^{-122}$), to mouse radixin ($1.1e^{-102}$) and to *Echinococcus multilocularis* tegument protein ($2.4e^{-21}$). Striking similarity was also detected at the amino acid level with these same proteins ($2.5e^{-146}$, $5.0e^{-46}$, $2.7e^{-145}$ and $7.6e^{-73}$, respectively) and to a potential product of a sequence tag from *Caenorhabditis elegans* ($3.7e^{-43}$). Weaker similarities were detected to the sequences of two protein tyrosine phosphatases, PTP-MEG and PTP-HI1 ($1.3e^{-17}$ and $9.6e^{-16}$, respectively), to erythrocyte protein 4.1 ($9.9e^{-14}$) and to a wide range of myosin, tropomyosin and paramyosin proteins. Because this novel gene is most closely related to moesin, ezrin and radixin (45–47% identity), it is called "merlin."

Northern blot analysis using total RNA from various cultured human tumor cell lines (FIG. 4) revealed two major hybridizing species of 2.6 kb and 7 kb, and a less intensely hybridizing RNA of 4.4 kb. A similar pattern was detected in poly(A)+RNA from various human tissues, including heart, brain, lung, skeletal muscle, kidney, pancreas and weakly in liver indicating that the merlin gene is expressed widely. The apparent poly(A) tails detected in JJR-6 and JJR-9 suggest that these clones may have derived from the approximately 2.6 kb RNA. The JJR-1 clone likely derived from one of the larger RNAs which apparently has a much longer 3' UTR. However, it cannot be excluded that the larger RNAs arise by alternative splicing that alters the length and composition of the coding sequence or by hybridization to related family members.

Example 4
Non-Overlapping Deletions Interrupt the Candidate NF2 Gene

To determine whether the deletion detected in GUS5069 interrupts the merlin gene, exon probes were prepared from across the coding sequence (FIG. 5) and Southern blots containing DNA from GUSH134A3 and GUSH134B1 (two independent hybrid lines containing the deleted chromosome 22) were analyzed. The results for probes I and II, shown in FIG. 5A, demonstrate that the probe I sequence was absent from both hybrids, while the probe 11 sequence was present in both. Thus, the genomic deletion truncates the merlin gene within the coding sequence between probes I and II, removing the 5' end.

In a search for additional alterations in the merlin gene, blots of restriction-digested DNA from 33 unrelated NF2 patients were scanned using the cDNA as probe. One patient, represented by cell line GUS5722, displayed altered fragments with several restriction enzymes suggestive of a small ~3.4 kb genomic deletion. This patient was analyzed using Southern blotting as shown in FIG. 5B. Probes III, IV and V all reside on the same 21 kb EcoRI fragment. In GUS5722, probes III and V detected both the normal EcoRI fragment and second fragment reduced in size by the deletion. Probe IV failed to detect the altered fragment in GUS5722 because it lies within the region deleted. PCR amplification of first strand CDNA from GUS5722 was performed and confirmed the presence of two types of PCR product (FIG. 6). Direct sequencing revealed that the novel PCR product was missing bases 1559 to 1792 of the cDNA, representing deletion of at least two exons. The absence of this segment would remove 78 amino acids from the protein, while leaving the reading frame intact. The GUS5722 cell line was generated from a member of a large NF2 kindred (Family 3 in Narod, S. A. et al., *Am. J. Hum. Genet.* 51:486–496 (1992)), and the deletion was present in five affected members and absent in eleven unaffected members of this pedigree.

The presence of non-overlapping deletions affecting the merlin gene in two independent families supported the conclusion that this gene represents the NF2 tumor suppressor. The presence of additional alterations were determined by single-strand conformational polymorphism (SSCP) analysis of PCR amplified first strand cDNA from tumor and lymphoblast samples. mRNA from four primary cultures of meningiomas (3 from NF2 patients with a family history of the disorder, 1 from a probable new mutation to NF2) was used and only selective regions of the mRNA were analyzed. Two of the tumors yielded aberrant patterns.

A meningioma from a female patient likely to have NF2 (see Experimental Procedures) displayed a reduced size for the expected non-denatured PCR product on SSCP gels (FIG. 6A). The vastly reduced level of the normal-sized PCR product suggests that this tumor had lost alleles in this region of chromosome 22. However, lymphocyte DNA was not available from this patient to confirm this. Direct sequence analysis of the PCR product confirmed the presence of a 4 bp deletion which removes bases 1781 to 1784. This deletion alters the reading frame and generates a shorter protein.

A meningioma from a male patient with NF2 (see Experimental Procedures) displayed an altered pattern on SSCP analysis (FIG. 6B). This meningioma was known to have lost heterozygosity on chromosome 22 based on comparison of polymorphic markers in blood and tumor DNA. Thus, the tumor suppressor model would suggest that the normal homologue had been lost and that the remaining copy of the gene represented the altered NF2 allele. Direct sequence analysis revealed a single base pair deletion at position 488 (FIG. 3) which introduces a frameshift which dramatically alters the predicted protein by introducing a stop codon within 100 bases.

Discussion

The delineation of non-overlapping deletions affecting different portions of the same chromosome 22 gene in two independent NF2 families is strong evidence that "merlin" is the NF2 tumor suppressor. Although it is possible that one or both of these deletions may affect a second gene in the area, should this gene in fact be the NF2 tumor suppressor, it would have to be affected by both deletions and must therefore be composed of exons interspersed with those of the merlin gene.

The larger of the deletions truncates the 5' end of the merlin gene, removing at least 120 amino acids. In addition, the extent of this deletion suggests that the 5' regulatory elements may also be missing. The smaller germline deletion removes 78 amino acids from the C-terminal portion of the protein. It is likely that such alterations would have drastic consequences for the function of the merlin protein.

The four base pairs and single base pair deletions in meningiomas from unrelated NF2 patients could possibly be of somatic origin and unrelated to the inherited predisposition. However, the almost exclusive expression of the altered copy of the merlin gene suggests that the normal sequence has been lost as a somatic event in tumor formation. This is consistent with the tumor suppressor model, and would suggest that the frameshift alterations actually represent germline mutations in these patients.

The merlin protein encoded at the candidate NF2 locus is a novel member of a growing family of proteins that have been proposed to act as links between the cell membrane and the cytoskeleton (Luna, E. J. et al., *Science* 258:955–964 (1992); Sato, N. et al., *J. Cell. Sci.* 103:131–143 (1992)). All members of the family (which includes moesin, ezrin, radixin, erythrocyte protein 4.1 and talin) contain a homologous domain of approximately 200 amino acids near the N-terminus followed by a segment that is predicted to be rich in a α-helix structure, and a highly charged C-terminal domain. Where they have been characterized from more than one mammalian species, members of this family are remarkably conserved. Moreover, highly related genes have been detected in the nematode, *Caenorhabditis elegans* (Waterson, R. et al., *Nature Genet.* 1:114–123 (1992)), and in the parasitic cestode, *Echinococcus multilocularis* (Frosch, P. M. et al., *Mol. Biochem. Parasitol.* 48:121–130).

Although most distantly related to merlin, protein 4.1 and talin are the best studied members of this family of proteins and have contributed the most towards understanding the function of the gene family. Protein 4.1 plays a critical role in maintaining membrane stability and cell shape in the erythrocyte by connecting the integral membrane proteins glycophorin and protein 3 (the anion channel) to the spectrin-actin lattice of the cytoskeleton (Leto, T. L. et al., *J. Biol. Chem.* 259:4603–4608 (1984); Conboy, J. et al., *Proc. Natl. Acad. Sci. U.S.A.* 83:9512–9516 (1986)). Genetic defects in protein 4.1 lead to one form of hereditary elliptocytosis (Tchernia, G. et al., *J. Clin. Invest.* 68:454–460 (1981); Delaunay, J. et al., *Nucleic Acids Res.* 12:387–395 (1984)). The binding site for glycophorin in protein 4.1 has been mapped to the N-terminal domain, suggesting that the homologous region in other family members might also bind to proteins in the membrane (Leto, T. L. et al. in *Membrane Skeletons and Cytoskeletal Membrane Associations,* Bennett et al., eds. Liss, New York (1986), pp. 201–209). Interestingly, a related domain is also found in two protein tyrosine phosphatases, PTP-MEG and PTP-H1, perhaps allowing these enzymes to associate with the membrane or the cytoskeleton (Gu, M. et al., *Proc. Natl. Acad. Sci. U.S.A.* 88:5867–5871 (1991); Yang, Q. et al., *Proc. Natl. Acad. Sci. U.S.A.* 88:5949–5953 (1991)). Binding of protein 4.1 to spectrin is mediated by the α-helical region of the protein, suggesting that the analogous segments of the other family members might also bind to cytoskeletal components (Correas, I. et al., *J. Biol. Chem.* 261:3310–3315 (1986)). Talin, a large protein found in regions of focal adhesions at cell-cell or cell-substrate contacts, appears to behave similarly, binding to the integrins in the cell membrane and to vinculin, thereby connecting the extracellular adhesion matrix to the cytoskeleton (Rees, D. J. G. et al., *Nature* 347:685–689 (1990); Luna, E. J. et al., *Science* 258:955–964 (1992)).

Moesin, ezrin and radixin are highly related proteins (~70–75% amino acid identity) that have each been postulated to provide a link between the cytoskeleton and the cell membrane. Each of these proteins shares 45–47% amino acid identity with merlin. Moesin (membrane-organizing extension spike protein), originally proposed as a receptor for heparin sulfate, has been found at or near the membrane in filopodia and other cell surface protrusions (Lankes, W. T. et al., *Proc. Natl. Acad. Sci. U.S.A.* 88:8297–8301 (1991); Furthmayr, H. et al., *Kidney Int.* 41:665–670 (1992)). Ezrin (cytovillin) has been seen in association with microvilli and cellular protrusions in many cell types (Pakkanen, R. et al., *J. Cell. Biochem.* 38:65–75 (1988); Gould, K. L. et al., *EMBO J.* 8:4133–4142 (1989); Turunen, O. et al., *J. Biol. Chem.* 264:16727–16732 (1989); Hanzel, D. et al., *EMBO J.* 10:2363–2373 (1991); Birbauer, E. et al., *J. Neurosci. Res.* 30:232–241 (1989)). Rapid redistribution of ezrin to regions of membrane remodeling, such as microvillar formation and membrane ruffling in response to growth factor stimulation, may be regulated by phosphorylation of the protein on both tyrosine and serine residues (Bretscher, A., *J. Cell Biol* 108:921–930 (1989); Krieg, J. et al., *J. Biol. Chem.* 267:19258–19265 (1992)). Radixin was isolated from the cell-cell adherents junction, where it is proposed to cap actin filaments and provide for their attachment to the cell membrane (Tchernia, G. et al., *J. Clin. Invest.* 68:454–460(1981); Funayama, N. et al., *J. Cell Biol.* 115:1039–1048 (1991)). Interestingly, in mitotic cells, radixin is concentrated at the cleavage furrow (Sato, N. et al., *J. Cell. Biol.* 113:321–320 (1991)).

Merlin possesses an N-terminal domain that is similar to protein 4.1 (28% identity), and to talin (21% identity). It is much more closely related, however, to moesin, ezrin and radixin (FIG. 7). Amino acid identity between merlin and the three latter proteins is concentrated in the first 342 residues (~63% identity). Like these other family members, the merlin protein is predicted to have a very long α-helical domain spanning 160–170 amino acids, beginning around residue 300. The first third of this domain overlaps with the region of strongest homology to moesin, ezrin and radixin. However, the remaining stretch shows limited similarity with these proteins and with a wide variety of myosins and tropomyosins. The C-terminal region of merlin contains a hydrophilic domain analogous to those of other family members. The similarity in structure of merlin to the other members of this family suggests that it too may normally act as a link between the cytoskeleton and the cell membrane and may thus represent a new class of tumor suppressor gene.

The cytoskeleton of mammalian cells is a complicated lattice-work of many different kinds of interconnected filaments (Luna, E. J. et al., *Science* 258:955–964 (1992)). It participates in a wide range of crucial cellular activities, including determining and altering shape, movement, cell division, cell-cell communication, cell anchorage, and organization of the intracellular milieu (Bernal, S. D. et al., *Crit. Rev. Oncol. Hematol* 3:191–204 (1985)). A defect in a protein which connects some component of this network to the plasma membrane could affect any of these processes, and have a consequent effect on growth control. For example, inactivation of the merlin protein may disregulate growth by disrupting a signal transduction pathway, by altering anchorage dependence, by upsetting the cell cycle regulation, or by some other mechanism remains to be determined. However, the characteristic structure of the merlin protein suggests that a search for its membrane and cytoskeletal binding targets might provide a logical route to exploring this question.

Example 5
Altered Coding Sequence of the Merlin Tumor Suppressor Permitting DNA Diagnosis in an Extended Pedigree with NF2

The objective of this example was to define the DNA mutation causing NF2 in a large, well-studied NF2 pedigree previously used to chromosomally map and to isolate the disease gene. The design was to use SSCP and sequence analysis of DNA amplified from the NF2 gene of affected and unaffected persons. The participants in the study set forth in this example were affected, unaffected, and at-risk members of a large pedigree segregating NF2. The results of the study showed a DNA alteration in the merlin coding sequence causing a shift on SSCP gels that was characteristic of the disease chromosome in this NF2 pedigree, being transmitted with the disorder, present only in affected members of the pedigree, absent in unaffected members of the family, and absent from 158 unrelated individuals. The alteration caused substitution of a tyrosine for an asparagine at position 220 of the merlin protein, in a region highly conserved in closely-related members of the family of cytoskeletal-associated proteins. The DNA change could also be detected by restriction enzyme digestion with RsaI.

A. Materials and Methods
1. Patients

The family studied in this Example has been extensively characterized clinically and described in detail previously (Wertelecki, W., et al., *New Engl. J. Med.* 319:278–283 (1988)). Medical records, histologic slides, death certificates and autopsy reports were sought for all symptomatic family members. Clinical assessments were performed including a search for signs of neurofibromatosis type 1. The results of computed tomography, MRI, and ophthalmologic and audiologic examinations were also sought. Diagnostic criteria used were those of the NIH consensus statement on neurofibromatosis (National Institutes of Health Consensus Development Conference Statement: Neurofibromatosis *Arch Neurol.* 45:575–578 (1988)). Lymphoblast lines were established from peripheral blood samples for all patients and relatives as previously described (Anderson et al., *In Vitro* 20:856–858 (1984)). DNA was isolated from peripheral or cultured leukocytes as described herein.

2. Polymerase Chain Reaction (PCR) Amplification of Exon 7

The genomic DNA of the patients and the unaffected control individuals were amplified using primers in the intron flanking exon 7. Approximately 30 ng of genomic DNA was amplified using the primer pair: 5'-CCATCTCACTTAGCTCCAATG-'3 [SEQ ID NO: 17] and 5'-CTCACTCAGTCT CTGTCTAC-'3 [SEQ ID NO: 18]. Amplification conditions include 20 $\mu$M each of dATP, dGTP, dCTP and dTTP, 4 pmoles of each primer, 0.5 units Taq polymerase, 10 mM Tris pH 8.3, 1.5 mM $MgCl_2$, 50 mM KCl, and 0.1 mg/ml gelatin in a total volume of 10 $\mu$l. Each reaction was cycled 35 times using the following steps: denaturation (at 95° C. for 1.5 minutes), primer annealing (at 60° C. for 1.5 minutes), and elongation (at 72° C. for 30 seconds).

3. Single Strand Conformational Polymorphism Analysis (SSCP)

SSCP analysis was performed according to the procedure of Orita et al. with minor modifications (Orita, M., et al., *Genomics* 5:874–879 (1989)). PCR amplification was carried out as described above except each reaction included 0.1 $\mu$l (10 mCi/ml) of $\alpha$-$^{32}$P dATP (Amersham Life Sciences). The amplified products were diluted 1:20 in 0.05% SDS, 6 mM EDTA, 40% formamide, 0.5 mg/ml xylene cyanol and 0.5 mg/ml bromphenol blue and heated to 90° C. for 3 minutes to denature the DNA. Samples were immediately cooled on ice and loaded on an 8% polyacrylamide gel containing 8% glycerol. Electrophoresis was carried out at room temperature for 12 to 16 hours at a constant power of 6–10 W. Gels were dried and exposed overnight to Kodak X-Omat AR film.

4. DNA Sequencing

The double-stranded PCR product containing the amplified exon was used as a template to generate single-strands by priming multiple rounds of DNA synthesis with one of the oligonucleotides previously used in the double-strand reaction (Gibbs, A., et al., *Proc. Natl. Acad. Sci. USA* 86:1919–1923 (1989)). Conditions for the single strand-producing reactions were identical to the PCR amplification of individual exons as described above. After 30 cycles, the product was ethanol precipitated in the presence of ammonium acetate and resuspended in 7 $\mu$l water for subsequent sequence analysis. The sequencing reactions were performed as described in Park et al. (*Hum. Mut.* 1:293–297 (1992)) utilizing Sequenase (U.S. Biochemicals). The amplified products were also cloned in T vector (Novagen) and the DNA obtained from the individual clones were sequenced using the Sequenase kit (U.S. Biochemicals).

B. Results
1. The Extended NF2 Pedigree

The NF2 gene shown in previous Examples was mapped precisely using genetic linkage analysis in an extremely large disease pedigree from which 137 blood samples were tested for polymorphic DNA markers on chromosome 22 (Wertelecki, W., et al., *New Engl. J. Med.* 319:278–283 (1988)). For this Example, a subset of the members of this kindred was selected to use for identification of the underlying NF2 mutation. The relationships of the family members used is shown in FIG. 8.

2. Scanning for NF2 Mutation Affecting Expression of Merlin

The NF2 gene has been identified herein based on non-overlapping genomic DNA deletions that altered its coding sequence in three independent NF2 families and in a meningioma from an unrelated NF2 patient. The merlin mRNA sequence consists of more than 2250 bases. The translated portion of the mRNA, an open reading frame of 1785 bases encoding the predicted 595 amino acid merlin protein is bracketed by 5' and 3' untranslated regions whose extent and variability remain to be defined completely. The merlin mRNA is spliced together from at least 17 exons that are distributed across about 100 kb of chromosome 22. In order to scan for mutations in the NF2 gene, the intron DNA sequence flanking each exon was determined, and DNA primers that permit amplification of the exon sequences from genomic DNA using the PCR have been developed.

The strategy for identifying DNA sequence differences representing potential mutations within the amplified coding sequences is the use of SSCP analysis (Orita, M., et al., Genomics 5:874–879 (1989)). In this method, individual exons from the patient's DNA are first amplified by PCR. The amplification products are then denatured to separate the complementary DNA strands and diluted to allow each single stranded DNA molecule to assume a secondary structure conformation by folding on itself. The single stranded DNA molecules are then subjected to polyacrylamide gel electrophoresis under nondenaturing conditions. The secondary structure, which is highly dependent on the precise DNA sequence, affects mobility of the strand on the gel. Even a single base change or deletion can produce a visible shift in the final band position on the gel.

The SSCP technique was applied to the DNA samples from the family in FIG. 8. A mobility shift was detected when comparing amplified PCR products from the affected family member, designated by an arrow in FIG. 8, relative to those from several normal unrelated individuals and from members of other unrelated NF2 families. This shift was detected by amplification of exon 7, comprising bp 819 to 894 of the merlin coding sequence. To confirm that this alteration is characteristic of the disease allele and transmitted with the disorder, additional affected and unaffected members of the NF2 pedigree were typed. FIG. 8 shows the deduced genotype of each family member tested in this and other analyses. FIG. 9 displays the results of one SSCP analysis in which five sibling pairs, each consisting of one affected and one unaffected individual, were tested. The altered SSCP pattern shows a clear correlation with inheritance of the disorder, and is present only in affected members of the pedigree. This SSCP pattern was not observed in a search of more an 300 independent chromosomes, derived from normal controls, other N2 families, and sporadic tumors of various types (colon, astrocytoma, schwannoma etc.).

3. Identification of the DNA Sequence Alteration Underlying the SSCP Variation

To determine the precise DNA alteration that caused the shifted mobility pattern in the SSCP analysis, direct DNA sequencing of the PCR amplification product from an affected member of the pedigree and an unrelated normal control was performed. The change in DNA sequence in the affected individual and its absence in an unaffected member of the pedigree was reconfirmed using cloned PCR product. The results of sequence analysis are shown in FIG. 10.

The control sequence displays an AAC codon encoding asparagine at position 220 of the merlin protein. The DNA from the patient reveals both an A and a T residue a the first position of this codon, suggesting a normal AAC codon on one chromosome, and a mutated TAC on the other. The TAC codon would substitute a tyrosine at position 220. Since this SSCP variation was absent from more than 300 independent chromosomes, it is unlikely that this change is simply a polymorphism. Rather, the change from the aliphatic side chain of asparagine to the bulky aromatic side chain of the tyrosine is likely to have significant consequences for the structure of the protein.

4. Confirmation of the Sequence Alteration by RsaI Digestion

The sequence change outlined above creates a GTAC stretch that is recognized and cleaved by the restriction endonuclease RsaI. This site is created 9 bp 3' to a pre-existing RsaI site in this exon. Thus, to confirm the presence of the same DNA change in other affected members of the family, its cotransmission with NF2, and its absence in unaffected members of the pedigree, we performed RsaI digests on the amplified PCR product from several family members. Typical results are shown in FIG. 11. The unaffected member of the family (U) and other control individuals display two RsaI fragments of 96 bp and 76 bp, whereas the affected individuals (A) produce an additional third fragment of 67 bp generated from the RsaI site created by the A→T change at codon 220.

Discussion

The isolation and characterization of the NF2 gene, encoding the merlin protein, creates new possibilities for accurate predictive testing in NF2. Until the NF2 gene was mapped to chromosome 22, no genetic testing was possible. Once the gene was mapped, it became possible to predict NF2 carrier status using linked DNA markers (Narod, S. A. et al., Am. J. Hum. Genet. 51:486–496 (1992)). Unfortunately, testing by linkage is limited by the availability of multiple family members for comparison, by lack of complete informativeness of linked markers, and by the diminished accuracy inherent in using a marker not located precisely within the disease gene. The precise identity of the NF2 gene discovered by the inventors now makes it possible to overcome these diagnostic hurdles by defining the exact molecular lesion associated with the disorder in any give pedigree.

Because mutations in NF2 were expected in general to inactivate the gene, they could have fallen into several different categories. DNA rearrangements, such as deletions, inversions, insertions, or duplications could be expected. Mutations that eliminate expression of the entire transcript, interfere with exon slicing, or disrupt its stability could effectively inactivate the gene. Finally, DNA sequence alterations within the coding sequence that cause premature termination of translation, yielding a truncated protein, or that result in a change in an amino acid residue critical for normal function of the merlin protein were also likely.

In this application, as shown in the exemplary material, the SSCP technique was applied as a rapid means to locate and confirm the probable molecular basis of NF2 in a large and well studied kindred (Wertelecki, W. et al., New Engl. J. Med. 319:278–283 (1988)). The technique used strategically placed primer sets to amplify small regions of the NF2 gene directly from genomic DNA using PCR. The findings were highly specific; none of the unaffected 158 control samples produced an altered SSCP pattern. As would be predicted, all samples from affected members of the same kindred produced the same altered SSCP pattern, reflecting the identical nature of the underlying molecular defect.

The sequence alteration in this family resulted in the substitution of a tyrosine residue for the asparagine at position 220 of the merlin protein. This change affects one of the most conserved stretches in the merlin protein as shown in FIG. 12. This particular asparagine residue, and all surrounding residues are present in all three closely related members of the family of cytoskeletal associated proteins, moesin, ezrin and radixin. The sequence conservation in this protein domain suggests that this region plays a crucial role in the function of the protein. A change from asparagine to tyrosine would be expected to significantly disrupt the structure of this domain. The drastic nature of this amino acid change, and the absence of the same DNA change from more than 300 independent chromosomes argue that this alteration is the cause of NF2 in this pedigree.

Example 6
Analysis of Merlin in Sporadic and Inherited Tumors

To facilitate e search for mutations in NF2 and related tumors, the exon-intron junction of the NF2 locus were sequenced, including the E16 additional exon that is alternatively spliced (Bianchi, A. B., et al., *Nature Genet.*, in press, 1994; Haase, V. H., et al., *Human Mol. Genet.*, in press, 1994). PCR assay were developed for all seventeen exons, and were used to scan the entire gene for mutations in sporadic and inherited vestibular schwannomas. The high proportion of tumors in which inactivating mutations were found indicates that the NF2 gene plays a fundamental role in schwannoma tumorigenesis.

Materials and Methods
Tissue samples

Tumor specimens were obtained at the time of surgery and frozen for DNA analysis. Blood samples were also obtained at the time of surgery to serve as normal tissue controls. High molecular weight DNA was extracted from peripheral blood leukocytes and from frozen pulverized tumor tissue by SDS-proteinase K digestion followed by phenol and chloroform extraction (Seizinger, B. R., et al., *Nature* 322:644–647 (1986)).

Design of primer pairs

Exonic primers were designed within the NF2 coding sequence near the intron-exon borders as determined by the results of exon trapping (Trofatter, J. A., et al., *Cell* 72:791–800 (1993)). For those regions not isolated by trapping, primers were synthesized at approximate 100 base pair intervals. Using these primers, an intronic sequence was obtained by directly sequencing cosmids containing the gene using a cycle sequencing kit (U.S. Biochemical). Intronic primer pair were then designed to amplify the splice donor and acceptor sites as well as the exon itself. In the case of E12, it was necessary to construct two overlapping primer sets to maintain a product length of less than 300 base pairs.

SSCP analysis

SSCP analysis was performed according to the procedure of Orita et al. (Orita, M., et al., *Genomics* 5:874–879 (1989)) with minor modifications. Approximately 50 ng of genomic DNA was amplified using appropriate intronic primer pairs (Table 2). Each 10 μl reaction contained 70 μM each of dATP, dCTP, dGTP and dTTP, 4 pmoles of each primer, 0.5 units Taq polymerase, 10 mM Tris pH 8.3, 1.5 mM MgCl$_2$, 50 mM KCl, 0.01% gelatin, and 0.1 μl α[$^{32}$P]dATP (Amersham, 10 mCi/ml). For E1, a MgCl$_2$ concentration of 0.5 mM was used. Amplification was carried out for 30 cycles as follows: 94° C. for 1 min., 55°–60° C. for 1 min., and 72° C. for 1 min., after an initial denaturation step at 94° C. for 4 min. One μl of labeled amplified DNA was diluted into 9 μl of 0.1% SDS and 10 mM EDTA, and an equal volume of loading dye (95% formamide, 0.5M EDTA, 0.05% bromphenol blue and 0.05% xylene cyanol) was added. The samples were denatured for 2 min. at 90° C. and separated on 6–8% polyacrylamide gels containing 8% glycerol for 16 hrs. at 6–8 W. Gels were dried and exposed to Kodak X-OMAT film.

DNA sequencing

For DNA sequencing, PCR amplifications were performed in 50 μl volumes as described above for SSCP analysis except that 200 μM dNTPs were added and a radioactive nucleotide was omitted. The product was sequenced by one of two methods. In the first, the double-stranded product was used as a template to generate single-strands by priming multiple rounds of DNA synthesis with one of the oligonucleotides previously used in the double-strand reaction (Gibbs, A., et al. *Proc. Natl. Acad. Sci. USA* 86:1919–1923 (1989)). Conditions for asymmetric PCR amplification were identical except that only one primer was added. The product was ethanol precipitated in the presence of ammonium acetate and resuspended in 10 μl H$_2$O for subsequent sequence analysis. The sequencing reactions were performed by the dideoxy chain-termination method using Sequenase (T7 DNA polymerase, U.S. Biochemical) under conditions recommended by the supplier. Alternatively, the PCR products were purified with BioSpin columns (BioRad) and ethanol precipitated. DNA sequencing was performed according to a standard cycle-sequencing protocol using VentR (exo-) DNA polymerase and the CircumVent Thermal Cycle kit (New England BioLabs). Both strands of exons with SSCP mobility shifts were analyzed in all cases.

Loss of heterozygosity analysis

Genomic DNA was amplified using primer pairs for the polymorphic dinucleotide repeats at markers D22S193 (Trofatter et al., in preparation) or D22S268 (Marineau, C., et al., *Hum. Mol. Genet.* 2:336 (1993)). The CA strand primer was 5' end-labeled with polynucleotide kinase and gamma-$^{32}$P ATP, and PCR was performed as described previously (Louis, D. N., et al., *Am. J. Pathol.* 141:777–782 (1992)). In some cases, loss of chromosome 22 alleles was determined by Southern blot analysis using probes at the following loci: D22S22, D22S29, D22S28, D22S15, D22S1, CRYB2, D22S10 and D22S9 (Rouleau, G. A., et al., *Genomics* 4:1–6 (1989)).

Results
Exon Structure of the NF2 Gene

The internal exons range in size from 45 base pairs to 218 base pairs, with an average of 111 base pairs. Of the fifteen internal exons, ten (E3, E5–7, E9–11, E14–16) were isolated using exon amplification, the technique described herein, which led to the isolation of the NF2 locus from cloned genomic DNA (see also Trofatter, J. A., et al., *Cell* 72:791–800 (1993)). Table 1 shows the DNA sequences immediately surrounding the intron-exon junctions, which all match the consensus for splice acceptor and donor sites. Additional intron sequences on both 5' and 3' sides that were used to design primers for PCR amplification are described herein in the section "Description of the Preferred Embodiments" (FIGS. 15A–Q herein).

PCR Assays for the Seventeen NF2 Gene Exons

For each internal exon, primers were chosen in flanking intron sequences to develop an assay for PCR amplification of the exon directly from genomic DNA. For E12, two overlapping primer sets were chosen to yield products in a size range amenable to SSCP analysis. Because E12 is 218 base pairs, two sets of primers were employed, one set spanning the 5' intron-exon junction and the 5' region of the exon and the other overlapping set spanning the remainder of the exon and the 3' exon-intron junction. In this way amplified fragments of a suitable length for SSCP analysis (140 and 284 base pairs, respectively) were generated. All of the coding region from E1 was amplified using one primer in the 5' untranslated region (UTR) and one in intron 1. For E17, a primer from the final intron was paired with a primer in the 3'UTR to amplify all of the E17 coding sequence, (along with the first 100 base pairs of 3'UTR). All assays (except that for E1) were performed according to standardized amplification conditions. As discussed in the exemplary material, E1 was amplified using a MgCl$_2$ concentration of 0.5 mM rather than 1.5 mM (to optimize the yield of PCR product). The annealing temperature was varied for optimum results. Table 2 lists the primers, annealing temperature and product size for each exon assay. In some cases (E7 and E8), an initial set of primers was used, but subsequently was replaced with a second primer pair. In some cases, the original primer was too far removed from the exon for convenient DNA sequencing or too close to the exon to detect potential intronic mutations. In such cases, primer pairs were used. In these instances both sets of primer pairs are listed.

Scanning for Mutations by SSCP Analysis of Blood-tumor Pairs

The exon PCR assays listed in Table 2 were used to scan the entire merlin coding sequence for mutations in schwannomas. SSCP analysis was applied to DNA extracted from thirty eight primary tumor specimens, including eight vestibular schwannomas from NF2 patients (Table 3), twenty-seven sporadic vestibular schwannomas (Table 4) and three sporadic spinal schwannomas (Table 4, S9, S25 and S27). DNA extracted from a blood sample of the corresponding individual was used for comparison in each case. All tumor-blood pairs were assayed for all exons.

Representative results of the SSCP analyses for three of the exons, (E2, E10 and E14) are shown in FIG. 13. For each assay, a lane of PCR product was run without denaturation (ND) to identify fully reannealed, double-stranded DNA in the test lanes. The other bands in the test lanes represent various conformations of the single-stranded DNAs in the product. For E2, the normal pattern is seen only in the blood DNA (B) of S29. S11 and S33 display mobility shifts that are detected in both blood and tumor DNA. This result indicates germline alterations. S29 displays a mobility shift only in the tumor DNA. This result indicates a somatic mutation. For E10 and E14, all blood DNAs display the normal pattern and all tumor DNAs display different mobility shifts. Both normal and altered PCR products were compared by direct sequence analysis to identify the precise base change(s) involved.

NF2 Mutations in Schwannomas

The blood and tumor DNAs were genotyped using polymorphic DNA markers to detect a loss of heterozygosity that could indicate deletion of one NF2 allele (Tables 3 and 4). General testing had predicted that at least sixteen of the thirty-eight tumors had lost one NF2 allele. Thus, the entire NF2 coding sequence for 58–60 independent alleles was examined by SSCP. No obvious polymorphism affecting coding or non-coding sequences was observed. This result indicates a remarkable degree of homogeneity for this gene sequence in the population. In contrast, mutations in both NF2 and sporadic tumors were readily detected. DNA differences from normal have been confirmed in twenty-seven of these tumors. Seven germline and twenty-five somatic alterations have been identified by sequence analysis. The results are summarized in Tables 3 and 4.

Germline mutations, present in both blood and tumor DNA, were delineated in five of the eight patients with a confirmed diagnosis of NF2 (Table 3). These changes occurred in disparate locations and included 1) point mutations creating stop codons at residues 57 and 60 of E2 (S11 and S33) and 1396 of E13 (S4); 2) a 28 base pair deletion creating a frame shift and premature stop codon in E10 (S1) and an insertion of one base into a splice donor site in E12 (S32). Two other germline alterations were found in blood and tumor DNA from individuals without a confirmed NF2 diagnosis (Table 4). These included 1) a single base change in the intron upstream of E7 in a sporadic spinal schwannoma (S9) and 2) a substitution of Cys for Arg at residue 418 in a sporadic vestibular schwannoma (S44). Although the two intron changes and the apparent missense mutation could conceivably represent polymorphisms, they were not found by SSCP analysis of 150 independent DNA samples from normal individuals or individuals with other types of tumors.

Somatic mutations were observed in tumors from five of the eight patients with NF2. These included two patients (S1 and S4) in whom a germline mutation was also detected (Table 3). In thirty sporadic tumors, a total of twenty somatic mutations were found (Table 4). In three cases in which chromosome 22 heterozygosity was maintained (S18, S24, and S29), two distinct somatic alterations were found in each tumor. For example, tumor S29 displayed small deletions of one base pair and four base pairs in E2 and E8, respectively (FIG. 14). In one tumor (S35), a complex of two adjacent deletions was detected in a single allele. One deletion removed five codons in-frame. The other deletion (beginning three base pairs downstream) caused a frameshift.

The twenty-five somatic mutations from NF2 and sporadic tumors were found throughout the gene and were associated with E1, E2, E3, E4, E7, E8, E9, E10, E12, E14 and E15. By far the most frequent lesions detected (19/25) were small deletions of one to sixty-one base pairs, that had either an obvious or presumed effect on splicing or that produced frameshifts that led to truncated proteins of altered sequence. A single mutation involved a frameshift resulting from a single base insertion (S42). The remaining five somatic changes were point mutations that either altered splice donor (S22) or acceptor (S12, S37) sites, produced a stop codon at residue 212 (S24), or generated a Met for Val substitution at residue 219 (S1).

Discussion

The results of the studies herein defining specific mutations immediately allow improved prenatal, presymptomatic and unaffected diagnosis for family members at risk. Highly accurate prenatal testing is now possible by direct examination of fetal DNA for the presence of characteristic SSCP shifts, altered DNA sequences, or gain or loss of restriction sites. Similarly, presymptomatic testing using these approaches could eliminate the need for up to half of at risk family members to undergo expensive and time consuming clinical monitoring, reducing the considerable financial and psychological burdens on these individuals. For those that test positive for the specific changes, medical care should be improved by the clarification of their status earlier in the course of their disease, which in turn might allow earlier consideration of surgical intervention. With the delineation of a larger number of mutations, it now becomes possible to discover whether the NF2 gene contains mutational "hot spots" which would simplify scanning.

NF2 is a disorder consistent with a "two-hit" model of tumorigenesis, in which homozygous inactivation of a gene that normally suppresses tumor growth is the critical event in tumor formation (Knudson, A. G., *Proc. Natl. Acad. Sci. USA* 68:820–823 (1971)). The same types of tumors that are present as multiple independent growths in NF2 patients occur as sporadic, solitary cases in the general population (Martuza and Eldridge, *New Eng. J. Med.* 318:684–688 (1988); Mulvihill, J., et al., *Ann. Intern. Med.* 113:39–52 (1990)). The familial and sporadic tumors both display frequent loss of genetic material from chromosome 22, in a region to which the NF2 gene defect has been mapped by linkage analysis (Kaiser-Kupfer, M. I., et al., *Arch. Ophthalmol.* 107:541–544 (1989); Rouleau, G. A., et al., *Nature* 329:246–248 (1987); Wertelecki, W., et al., *New Engl. J. Med.* 319:278–283 (1988); Rouleau, G. A., et al., *Am. J. Hum. Genet.* 46:323–328 (1990); Narod, S. A., et al., *Am. J. Hum. Genet.* 51:486–496 (1992); Seizinger, B. R., et al., *Nature* 322:644–647 (1986); Seizinger, B. R., et al., *Science* 236:317–319 (1987); Seizinger, B. R., et al., *Proc. Natl. Acad. Sci. USA* 84:5419–5423 (1987); Couturier, J., et al., *Cancer Genet. Cytogenet.* 45:55–62 (1990); Bijlsma, E. K., et al., *Genes Chromosom. Cancer* 5:201–205 (1992); Fontaine, B., et al., *Ann. Neurol.* 29:183–196 (1991); Fontaine, B., et al., *Genomics* 10:280–283 (1991); Fiedler, W., et al., *Genomics* 10:786–791 (1991); Wolff, R. K., et al., *Am. J. Hum. Genet.* 51:478–485 (1992)). Thus, it is presumed that the NF2 locus encodes a tumor suppressor and that inactivation of both alleles by loss or mutation in specific cells results in unregulated proliferation. However, only specific cell types are affected in this way as the vast majority of tumors seen in NF2 are schwannomas, and particularly vestibular schwannomas and meningiomas.

The results herein implicate merlin as a tumor suppressor. Whereas germline mutations are present in both blood and tumor DNA from NF2 patients, somatic mutation of merlin is a frequent event in schwannomas. In several cases, two inactivating mutations were detected in the same tumor. In many others, a single mutant allele remained following the loss of the second copy of the locus. The alterations occured throughout the NF2 gene. Most exons displayed at least one mutation.

One alteration, conversion of the Arg codon at position 57 to a stop codon, has been seen twice before in independent NF2 patients (Rouleau, G. A., et al., *Nature* 363:515–521 (1993)), suggesting that this site containing a cCpG dinucleotide may be particularly prone to C→T transitions. The presence of this change in the blood DNA of S11 combined with this absence from either parent demonstrate that this is a case of a new mutation to NF2.

Two new missense mutations were identified, Val219Met and Arg418Cys, which may target these residues as particularly important in merlin's tumor suppressor function. The Val at position 219, one residue away from the previously reported Asn220Tyr mutation, is located within the protein 4.1 domain that is characteristic of this family and is conserved in human moesin, radixin, and protein 4.1, but changed to lie in human ezrin. The Arg at position 418 is located in the long α-helical domain that comprises most of the C-terminal half of merlin and its relatives but is not strictly conserved in the other human members of this protein family.

A surprising number of somatic mutations involve changes in intron sequences. These may occur at a distance from the exon-intron junction. The absence of these alterations in blood-derived DNA of the same individuals, and the failure to detect the same change in any other individuals, indicate that these mutations are de novo events associated with tumor formation.

In addition to expanding the number and variety of germline NF2 mutations described, the examples herein suggest that germline alterations occur in patients not yet diagnosed clinically with NF2. One patient, with a single spinal schwannoma, displayed a single base alteration in an intron sequence. Another with a single vestibular schwannoma, displayed the Arg418Cys change described above. Careful clinical follow-up is indicated for these patients. It is possible that they represent a class of individuals with mutations that only mildly affect normal merlin function, and consequently do not produce the full NF2 phenotype.

The development of reliable PCR assays for each exon of the NF2 gene should facilitate greatly the cataloging of mutations in NF2 patients and their tumors by genomic scanning. It can be expected that a detailed mutational analysis of the NF2 gene, identifying sites particularly prone to alteration, pinpointing amino acid residues crucial for normal function, and providing a basis for relating specific alterations with variations in phenotype will result. Perhaps most important, however, the ability to rapidly scan the NF2 gene for mutations will accelerate the assessment of a role for merlin in other tumor types.

TABLE 1

Intron-Exon Boundaries of the NF2 Gene

| Exon | Splice Acceptor | Start (bp)[1] | Exon Start | Exon Length | Exon End | End (bp) | Splice Donor |
|---|---|---|---|---|---|---|---|
| 1 | | | | | GAG | 114 | GTAACCGGCC |
| 2 | GTTATTGCAG | 115 | ATG | 126 | AAG | 240 | GTTGGGCTAG |
| 3 | AATTCTGCAG | 241 | GTA | 123 | CAG | 363 | GTACATCAGT |
| 4 | CTCCTTTCAG | 364 | GTA | 84 | AAG | 447 | GTAGGCTCAA |
| 5 | TTCTTTCCAG | 448 | TAT | 69 | AGG | 516 | GTAAGAGATT |
| 6 | TTTTTGGTAG | 517 | GTA | 83 | CAG | 599 | GTGAGGCCCA |
| 7 | CTCCCCACAG | 600 | GGA | 76 | CGG | 675 | GTGTGTTGAA |
| 8 | GGATCCACAG | 676 | AAT | 135 | GAG | 810 | GTAGGACATG |
| 9 | ATTCTTCCAG | 811 | TTT | 75 | CTG | 885 | GTAAGTTGAG |
| 10 | GTGGCCACAG | 886 | ATT | 114 | CAG | 999 | GTGAGCACAA |
| 11 | CCCCTCGCAG | 1000 | ATG | 123 | CTG | 1122 | GTGATTTCTG |
| 12 | TGCCCTCCAG | 1123 | ATG | 218 | GAG | 1340 | GTGAGGGGGC |
| 13 | TTCCTTGCAG | 1341 | GGC | 106 | CCG | 1446 | GTGAGCCTGG |
| 14 | TCATTAACAG | 1447 | CCC | 128 | AAA | 1574 | GTATGTAGCC |
| 15 | TTGCCGGCAG | 1575 | AGT | 163 | AAG | 1737 | GTACCCAGGG |
| 16 | GCTGGTTTAG | 1738 | CCT | 45 | AAA | 1782 | GTAGGTTGTT |
| 17 | TTTCTTACAG | 1783 | CTC | | | | |

[1]Base pair numbering is based on #1 being the A of the initiator ATG

| Exon | Splice Acceptor | Splice Donor |
|---|---|---|
| 1 |  | SEQ ID NO: 19 |
| 2 | SEQ ID NO: 20 | SEQ ID NO: 21 |
| 3 | SEQ ID NO: 22 | SEQ ID NO: 23 |
| 4 | SEQ ID NO: 24 | SEQ ID NO: 25 |
| 5 | SEQ ID NO: 26 | SEQ ID NO: 27 |
| 6 | SEQ ID NO: 28 | SEQ ID NO: 29 |
| 7 | SEQ ID NO: 30 | SEQ ID NO: 31 |
| 8 | SEQ ID NO: 32 | SEQ ID NO: 33 |
| 9 | SEQ ID NO: 34 | SEQ ID NO: 35 |
| 10 | SEQ ID NO: 36 | SEQ ID NO: 37 |
| 11 | SEQ ID NO: 38 | SEQ ID NO: 39 |
| 12 | SEQ ID NO: 40 | SEQ ID NO: 41 |
| 13 | SEQ ID NO: 42 | SEQ ID NO: 43 |
| 14 | SEQ ID NO: 44 | SEQ ID NO: 45 |
| 15 | SEQ ID NO: 46 | SEQ ID NO: 47 |
| 16 | SEQ ID NO: 48 | SEQ ID NO: 49 |
| 17 | SEQ ID NO: 50 |  |

-continued

| Exon | Product | Primer #1 | Primer #2 |
|---|---|---|---|
| 6 | 161 | SEQ ID NO: 65 | SEQ ID NO: 66 |
| 7 | 173 | SEQ ID NO: 67 | SEQ ID NO: 68 |
|  | 170 | SEQ ID NO: 69 | SEQ ID NO: 70 |
| 8 | 247 | SEQ ID NO: 71 | SEQ ID NO: 72 |
|  | 232 | SEQ ID NO: 73 | SEQ ID NO: 74 |
| 9 | 300 | SEQ ID NO: 75 | SEQ ID NO: 76 |
| 10 | 260 | SEQ ID NO: 77 | SEQ ID NO: 78 |
| 11 | 268 | SEQ ID NO: 79 | SEQ ID NO: 80 |
| 12A | 140 | SEQ ID NO: 81 | SEQ ID NO: 82 |
| 12B | 284 | SEQ ID NO: 83 | SEQ ID NO: 84 |
| 13 | 228 | SEQ ID NO: 85 | SEQ ID NO: 86 |
| 14 | 254 | SEQ ID NO: 87 | SEQ ID NO: 88 |
| 15 | 317 | SEQ ID NO: 89 | SEQ ID NO: 90 |
|  | 248 | SEQ ID NO: 91 | SEQ ID NO: 92 |
| 16 | 148 | SEQ ID NO: 93 | SEQ ID NO: 94 |
| 17 | 177 | SEQ ID NO: 95 | SEQ ID NO: 96 |

TABLE 2

Primers for Exon PCR Assays

| Exon[1] | Product | Temp[2] (°C.) | Primer #1 (5'–3') | Primer #2 (5'–3') |
|---|---|---|---|---|
| 1 | 235 | 58 | GCTAAAGGGCTCAGAGTGCAG | GAGAACCTCTCGAGCTTCCAC |
| 2 | 182 | 60 | TGTCCTTCCCCATTGGTTTG | CAGTTTCATCGAGTTCTAGCC |
|  | 244 | 58 | AGTGCAGAGAAAAGGTTTTATTAATGAT | TGGAAAGCTCACGTCAGCC |
| 3 | 272 | 60 | GCTTCTTTGAGGGTAGCACA | GGTCAACTCTGAGGCCAACT |
| 4 | 188 | 59 | CCTCACTTCCCCTCACAGAG | CCCATGACCCAAATTAACGC |
| 5 | 148 | 60 | GCTCTCCCTTTCTTCTTTCC | TCCTTCAAGTCCTTTGGTTAGC |
|  | 171 | 58 | TGGCAGTTATCTTTAGAATCTC | TTAGACCACATATCTGCTATG |
| 6 | 161 | 60 | CATGTGTAGGTTTTTTATTTTGC | GCCCATAAAGGAATGTAAACC |
| 7 | 173 | 60 | CCATCTCACTTAGCTCCAATG | CTCACTCAGTCTCTGTCTAC |
|  | 170 | 60 | GAATGCTTGATTTGGTGCCC | GAGGTTTCAACACACCCGGA |
| 8 | 247 | 60 | GAAGGTTGAATAAAATTTTGAGCCTC | GACAGGGAAAGATCTGCTGGACC |
|  | 232 | 60 | CTGTTCTTATTGGATCCACAG | AACAACCACACCCTCAAAGC |
| 9 | 300 | 58 | GACTTGGTGCTCCTAATTCCC | CCATTATCAGTAATGAAAACCAGG |
| 10 | 260 | 59 | TGCTACCTGCAAGAGCTCAA | CTGACCACACAGTGACATC |
| 11 | 268 | 60 | TCTTTGGCCCTTGTGGCAC | CAGGAGACCAAGCTCCAGAA |
| 12A | 140 | 60 | TTCAGCTAAGAGCACTGTGC | CGCTGCATTTCCTGCTCAG |
| 12B | 284 | 58 | GCTGAAAAGGCCCAGATCA | CTTGAGGACAACTGCTGTAG |
| 13 | 228 | 60 | GGTGTCTTTTCCTGCTACCT | GGGAGGAAAGAGAACATCAC |
| 14 | 254 | 60 | TGTGCCATTGCCTCTGTG | AGGGCACAGGGGGCTACA |
| 15 | 317 | 58 | TGGCCAAGTAGAGACGTGA | TACAAGAAAGAGACCCTGGG |
|  | 248 | 58 | TCTGCCCAAGCCCTGATGC | TGGTCCTGATCAGCAAAATAC |
| 16 | 148 | 60 | GGCATTGTTGATATCACAGGG | GGCAGCACCATCACCACATA |
| 17 | 177 | 60 | CTCTCAGCTTCTTCTCTGCT | CCAGCCAGCTCCTATGGATG |

[1]All exons were scanned by single PCR assays except exon 12, for which overlapping assays (12A and 12B) were required. For exons 2, 5, 7, 8 and 15, two different PCR assays were developed.
[2]Annealing temperature for PCR reaction

| Exon | Product | Primer #1 | Primer #2 |
|---|---|---|---|
| 1 | 235 | SEQ ID NO: 51 | SEQ ID NO: 52 |
| 2 | 182 | SEQ ID NO: 53 | SEQ ID NO: 54 |
|  | 244 | SEQ ID NO: 55 | SEQ ID NO: 56 |
| 3 | 272 | SEQ ID NO: 57 | SEQ ID NO: 58 |
| 4 | 188 | SEQ ID NO: 59 | SEQ ID NO: 60 |
| 5 | 148 | SEQ ID NO: 61 | SEQ ID NO: 62 |
|  | 171 | SEQ ID NO: 63 | SEQ ID NO: 64 |

TABLE 3

NF2 Gene Mutations in Schwannomas from NF2 Patients

| Tumor | Exon | DNA Sequence Alteration[1] | Codon Change[2] | Consequence | Origin[3] | Alleles[4] |
|---|---|---|---|---|---|---|
| S1 | E7 | 655 G → A | Val219Met | Missense | S | 2 |
| S1 | E10 | 904/6 to 931/3 del 28 bp | Gly302fs > 322X | Frameshift |  |  |
| S4 | E3 | 353 to 363 + 19 del 30 bp |  | Splice donor site | S | 2 |
| S4 | E13 | 1396 C → T | Arg466X | Nonsense | G |  |
| S10 | E9 | 844 del 1 bp (G) | Val282fs > 296X | Frameshift | S | 2 |
| S11 | E2 | 169 C → T | Arg57X | Nonsense | G | 2 |
| S32 | E12 | 1340 + 2 inst 1 bp (t) |  | Splice donor? | G | 2 |
| S33 | E2 | 179 G → A | Trp60X | Nonsense | G | 1 |
| S34 | E14 | 1451 to 1452 del 2 bp (TG) | Met484fs > 494X | Frameshift | S | NI |
| S36 | E7 | 600–28 to −5 del 24 bp |  | Splice acceptor? | S | 2 |

[1]Numbering of bases showing alteration is given relative to the cDNA sequence with the initiator ATG beginning at base 1. All coding sequence bases are given in upper case. When the alteration affects intronic sequence, it is presented in lower case and numbered as "−" (5' intron) or "+" (3' intron) the requisite number of bases from the first or last base of the exon, respectively. For deletions, the span of deleted bases (numbered as above) is given, followed by the deletion size ("del"). For deletions of less than 5 bp, the deleted base are also named. Where the start position of the deletion is uncertain, the alternative ranges of bases deleted are shown. Insertion is indicated by "ins" followed by the number of bases inserted, and their identity.
[2]Original amino acid and position of the residues in the protein (numbered from the initiator Met as 1) is followed by new amino acid for missense mutation, X for nonsense mutation, or fs for frameshift, followed by the position of the next in-frame stop codon.
[3]S = somatic mutation; G = germline mutation.
[4]Number of NF2 alleles in tumor predicted by heterozygosity testing with Chr 22 DNA markers. NI = not informative.

TABLE 4

NF2 Gene Mutations in Sporadic Schwannomas[1]

| Tumor | Exon | DNA Sequence Alteration | Codon Change | Consequence | Origin | Alleles |
|---|---|---|---|---|---|---|
| S2 | E3 | 241–22 to −13 del 10 bp |  | Splice acceptor? | S | 1 |
| S3 |  |  |  |  |  | NI |
| S5 |  |  |  |  |  | 1 |
| S6 |  |  |  |  |  | 2 |
| S9 | E7 | 600–32 t → a |  | Acceptor-branch site? | G | 2 |
| S12 | E7 | 600–1 g → a |  | Splice acceptor site | S | 1 |
| S13 |  |  |  |  |  | 2 |
| S14 |  |  |  |  |  | 1 |
| S15 | E15 | 1634/6 to 1694/6 del 61 bp | Ile546fs > 550X | Frameshift | S | 1 |
| S16 | E4 | 439 del 1 (C) | Gln147fs > 174X | Frameshift | S | 2 |
| S17 |  |  |  |  |  | 2 |
| S18 | E8 | 676–10 to 726 del 61 bp |  | Splice acceptor site | S | 2 |
|  | E12 | 1266 to 1267 del 2 (GA) | Glu422fs > 442X | Frameshift | S |  |
| S19 | E15 | 1575–26/−27 to 1581/2 del 34 bp |  | Splice acceptor site | S | 1 |
| S22 | E7 | 675 + 1 g → t |  | Splice donor site | S | 1 |
| S23 |  |  |  |  |  | 1 |
| S24 | E7 | 634 C → T | Gln212X | Nonsense | S | 2 |
|  | E10 | 905 to 912 del 8 bp | Gly302fs > 331X | Frameshift | S |  |
| S25 | E10 | 992 to 999 + 1 del 9 bp |  | Splice donor Site | S | 1 |
| S26 |  |  |  |  |  | 1 |
| S27 |  |  |  |  |  | 2 |
| S29 | E2 | 134 del 1 (A) | Asp45fs > 123X | Frameshift | S | 2 |
|  | E8 | 729 to 732 del 4 (TTAT) | Ile243fs > 251X | Frameshift | S |  |

TABLE 4-continued

NF2 Gene Mutations in Sporadic Schwannomas[1]

| Tumor | Exon | DNA Sequence Alteration | Codon Change | Consequence | Origin | Alleles |
|---|---|---|---|---|---|---|
| S30 | E4 | 447 or 447 + 1 del 1 (G or g) | Lys149fs > 174X | Framehift or splice donor site | S | 1 |
| S31 | | | | | | 1 |
| S35 | E1 | 65/70 to 79/84 del 15 bp | del 5 aa | | S | 1 |
| | | 88 to 109 del 22 bp | Asp30fs > 40X | Frameshift | | |
| S37 | E4 | 364–2 a → g | | Splice acceptor site | S | 2 |
| S38 | E10 | 933 del 1 (G) | Arg311fs > 322X | Frameshift | S | 2 |
| S39 | E12 | 1223 to 1227 del 5 bp | Glu408fs > 442X | Frameshift | S | 1 |
| S40 | | | | | | 1 |
| S42 | E14 | 1517/20 ins 1 (T) | Phe507fs > 513X | Frameshift | S | 2 |
| S43 | E14 | 1571/4 del 1 (A) | Lye525fs > 550X | Frameshift | S | 2 |
| S44 | E12 | 1252 C → T | Arg418Cys | Missense | G | 2 |

[1]Explanation of all symbols can be found in Table 3.

Having now fully described the invention, it will be understood by those with skill in the art that the scope may be performed within a wide and equivalent range of conditions, parameters, and the like, without affecting the spirit or scope of the invention or of any embodiment thereof.

```

What is claimed is:

1. Substantially purified human merlin protein, wherein said human merlin protein is encoded by a merlin gene on human chromosome 22, between positions D22S1 and D22S28, and further wherein said merlin protein has tumor suppressor activity.

2. Substantially purified merlin protein comprising the amino acid sequence shown in SEQ ID NO: 16.

3. An anti-merlin antibody.

4. A substantially purified merlin protein encoded by a DNA molecule comprising a nucleotide sequence encoding the amino acid sequence of SEQ ID NO 16.

5. A fusion protein comprising a first coding sequence and a second coding sequence, wherein said first coding sequence is a signal sequence for secretion, tissue targeting, or cellular localization, and said second coding sequence comprises the amino acid sequence shown in SEQ ID NO: 16.

6. A mutant of the merlin protein as claimed in claim 1, wherein said mutant comprises a mutation associated with neurofibromatosis-2.

7. The mutant merlin protein as claimed in claim 6, wherein said mutation is a substitution of Tyr for Asn at amino acid position 220 of SEQ ID NO:16.

8. The mutant merlin protein as claimed in claim 6, wherein said mutation is selected from the group consisting of: (1) the truncation of said mutant merlin protein at amino acid position 57 of SEQ ID NO: 16; (2) the substitution of a Met for a Val at amino acid position 219 of SEQ ID NO: 16; and (3) the substitution of a Cys for an Arg at amino acid position 418 of SEQ ID NO:16.

9. A method of making a merlin protein having tumor suppressor activity, comprising:
   a) transforming a host cell with a nucleic acid molecule capable of expressing a merlin protein having tumor suppressor activity;
   b) expressing said merlin protein in said host cell; and
   c) obtaining said merlin protein from a cell culture comprising said host cells.

10. The method of making a merlin protein as claimed in claim 9, wherein said nucleic acid molecule encodes the amino acid sequence of SEQ ID NO: 16.

11. A method of making a mutant merlin protein, comprising:
   a) transforming a host cell with a nucleic acid molecule comprising a mutant merlin gene having a mutation associated with neurofibromatosis-2;
   b) expressing said mutant merlin protein in said host cells; and
   c) obtaining said mutant merlin protein from a cell culture comprising said host cells.

12. The method of making a mutant merlin protein as claimed in claim 11, wherein said mutant merlin gene comprises an A to T transversion at the first base encoding amino acid 220 of the amino acid sequence shown in SEQ ID NO: 16.

13. The method of making a mutant merlin protein as claimed in claim 11, wherein said mutant merlin gene comprises a mutation selected from the group consisting of: (1) a conversion of the Arg codon corresponding to amino acid position 57 of SEQ ID NO: 16 to a stop codon; (2) a conversion of a Val codon corresponding to amino acid 219 of SEQ ID NO: 16 to a Met codon; and (3) a conversion of an Arg codon corresponding to amino acid position 418 of SEQ ID NO: 16 to a Cys codon.

14. An anti-merlin antibody as claimed in claim 3, wherein said antibody is capable of binding a merlin protein having the amino acid sequence shown in SEQ ID NO: 16.

15. An anti-merlin antibody as claimed in claim 3, wherein said antibody is capable of binding a mutant merlin protein comprising a mutation associated with neurofibromatosis-2.

16. An anti-merlin antibody as claimed in claim 15, wherein said mutation is the substitution of Tyr for Asn at amino acid position 220 of SEQ ID NO: 16.

* * * * *

                         SEQUENCE LISTING (1) GENERAL INFORMATION:

(iii) NUMBER OF SEQUENCES: 120

(2) INFORMATION FOR SEQ ID NO:1:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (xi) SEQUENCE DESCRIPTION: SEQ ID NO:1:

CAGATTGTTC ATTCCAAGTG G                                                 21

(2) INFORMATION FOR SEQ ID NO:2:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:2:

ACCCTGAGGA ATCCACTACC                                                   20

(2) INFORMATION FOR SEQ ID NO:3:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:3:

TGCACACACA TCCTTTTCAC                                                   20
```

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:4:

```
GAGAGAGACT GCTGTCTCAA AAA                                              23
```

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:5:

```
AGGAGGCTGA ACGCACGAG                                                   19
```

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:6:

```
TGGTATTGTG CTTGCTGCTG                                                  20
```

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:7:

```
CTTCAACCTG ATTGGTGACA G                                                21
```

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:8:

```
TGGTATTGTG CTTGCTGGTG                                                  20
```

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:9:

```
AGGTACTGGA TCATGATGTT TC                                               22
```

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:10:

TTTGGAAGCA ATTCCTCTTG G                         21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:11:

CCAGCCAGCT CCCTATGGAT G                         21

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:12:

AGCTGAAATG GAATATCTGA AG                       22

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:13:

GCCTTCTCCT CCCTGGCCTG                          20

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:14:

GATGGAGTTC AATTGCGAGA TG                       22

(2) INFORMATION FOR SEQ ID NO:15:

(i) SEQUENCE CHARACTERISTICS:
        (A) LENGTH: 2257 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 220..2004

(xi) SEQUENCE DESCRIPTION: SEQ ID NO:15:

```
                                                           -continued

ACGGCAGCCG TCAGGGACCG TCCCCCAACT CCCCTTTCCG CTCAGGCAGG GTCCTCGCGG      60

CCCATGCTGG CCGCTGGGGA CCCGCGCAGC CCAGACCGTT CCCGGGCCGG CCAGCCGGCA     120

CCATGGTGGC CCTGAGGCCT GTGCAGCAAC TCCAGGGGGG CTAAAGGGCT CAGAGTGCAG     180

GCCGTGGGGC GCGAGGGTCC CGGGCCTGAG CCCCGCGCC ATG GCC GGG GCC ATC        234
                                            Met Ala Gly Ala Ile
                                              1               5

GCT TCC CGC ATG AGC TTC AGC TCT CTC AAG AGG AAG CAA CCC AAG ACG       282
Ala Ser Arg Met Ser Phe Ser Ser Leu Lys Arg Lys Gln Pro Lys Thr
             10                  15                  20

TTC ACC GTG AGG ATC GTC ACC ATG GAC GCC GAG ATG GAG TTC AAT TGC       330
Phe Thr Val Arg Ile Val Thr Met Asp Ala Glu Met Glu Phe Asn Cys
             25                  30                  35

GAG ATG AAG TGG AAA GGG AAG GAC CTC TTT GAT TTG GTG TGC CGG ACT       378
Glu Met Lys Trp Lys Gly Lys Asp Leu Phe Asp Leu Val Cys Arg Thr
             40                  45                  50

CTG GGG CTC CGA GAA ACC TGG TTC TTT GGA CTG CAG TAC ACA ATC AAG       426
Leu Gly Leu Arg Glu Thr Trp Phe Phe Gly Leu Gln Tyr Thr Ile Lys
         55                  60                  65

GAC ACA GTG GCC TGG CTC AAA ATG GAC AAG AAG GTA CTG GAT CAT GAT       474
Asp Thr Val Ala Trp Leu Lys Met Asp Lys Lys Val Leu Asp His Asp
70                   75                  80                  85

GTT TCA AAG GAA GAA CCA GTC ACC TTT CAC TTC TTG GCC AAA TTT TAT       522
Val Ser Lys Glu Glu Pro Val Thr Phe His Phe Leu Ala Lys Phe Tyr
                 90                  95                 100

CCT GAG AAT GCT GAA GAG GAG CTG GTT CAG GAG ATC ACA CAA CAT TTA       570
Pro Glu Asn Ala Glu Glu Glu Leu Val Gln Glu Ile Thr Gln His Leu
            105                 110                 115

TTC TTC TTA CAG GTA AAG AAG CAG ATT TTA GAT GAA AAG ATC TAC TGC       618
Phe Phe Leu Gln Val Lys Lys Gln Ile Leu Asp Glu Lys Ile Tyr Cys
            120                 125                 130

CCT CCT GAG GCT TCT GTG CTC CTG GCT TCT TAC GCC GTC CAG GCC AAG       666
Pro Pro Glu Ala Ser Val Leu Leu Ala Ser Tyr Ala Val Gln Ala Lys
        135                 140                 145

TAT GGT GAC TAC GAC CCC AGT GTT CAC AAG CGG GGA TTT TTG GCC CAA       714
Tyr Gly Asp Tyr Asp Pro Ser Val His Lys Arg Gly Phe Leu Ala Gln
150                 155                 160                 165

GAG GAA TTG CTT CCA AAA AGG GTA ATA AAT CTG TAT CAG ATG ACT CCG       762
Glu Glu Leu Leu Pro Lys Arg Val Ile Asn Leu Tyr Gln Met Thr Pro
                170                 175                 180

GAA ATG TGG GAG GAG AGA ATT ACT GCT TGG TAC GCA GAG CAC CGA GGC       810
Glu Met Trp Glu Glu Arg Ile Thr Ala Trp Tyr Ala Glu His Arg Gly
            185                 190                 195

CGA GCC AGG GAT GAA GCT GAA ATG GAA TAT CTG AAG ATA GCT CAG GAC       858
Arg Ala Arg Asp Glu Ala Glu Met Glu Tyr Leu Lys Ile Ala Gln Asp
            200                 205                 210

CTG GAG ATG TAC GGT GTG AAC TAC TTT GCA ATC CGG AAT AAA AAG GGC       906
Leu Glu Met Tyr Gly Val Asn Tyr Phe Ala Ile Arg Asn Lys Lys Gly
        215                 220                 225

ACA GAG CTG CTG CTT GGA GTG GAT GCC CTG GGG CTT CAC ATT TAT GAC       954
Thr Glu Leu Leu Leu Gly Val Asp Ala Leu Gly Leu His Ile Tyr Asp
230                 235                 240                 245

CCT GAG AAC AGA CTG ACC CCC AAG ATC TCC TTC CCG TGG AAT GAA ATC      1002
Pro Glu Asn Arg Leu Thr Pro Lys Ile Ser Phe Pro Trp Asn Glu Ile
                250                 255                 260

CGA AAC ATC TCG TAC AGT GAC AAG GAG TTT ACT ATT AAA CCA CTG GAT      1050
Arg Asn Ile Ser Tyr Ser Asp Lys Glu Phe Thr Ile Lys Pro Leu Asp
            265                 270                 275

AAG AAA ATT GAT GTC TTC AAG TTT AAC TCC TCA AAG CTT CGT GTT AAT      1098
```

```
                Lys Lys Ile Asp Val Phe Lys Phe Asn Ser Ser Lys Leu Arg Val Asn
                                280                 285                 290

AAG CTG ATT CTC CAG CTA TGT ATC GGG AAC CAT GAT CTA TTT ATG AGG              1146
Lys Leu Ile Leu Gln Leu Cys Ile Gly Asn His Asp Leu Phe Met Arg
            295                 300                 305

AGA AGG AAA GCC GAT TCT TTG GAA GTT CAG CAG ATG AAA GCC CAG GCC              1194
Arg Arg Lys Ala Asp Ser Leu Glu Val Gln Gln Met Lys Ala Gln Ala
310                 315                 320                 325

AGG GAG GAG AAG GCT AGA AAG CAG ATG GAG CGG CAG CGC CTC GCT CGA              1242
Arg Glu Glu Lys Ala Arg Lys Gln Met Glu Arg Gln Arg Leu Ala Arg
                330                 335                 340

GAG AAG CAG ATG AGG GAG GAG GCT GAA CGC ACG AGG GAT GAG TTG GAG              1290
Glu Lys Gln Met Arg Glu Glu Ala Glu Arg Thr Arg Asp Glu Leu Glu
            345                 350                 355

AGG AGG CTG CTG CAG ATG AAA GAA GAA GCA ACA ATG GCC AAC GAA GCA              1338
Arg Arg Leu Leu Gln Met Lys Glu Glu Ala Thr Met Ala Asn Glu Ala
        360                 365                 370

CTG ATG CGG TCT GAG GAG ACA GCT GAC CTG TTG GCT GAA AAG GCC CAG              1386
Leu Met Arg Ser Glu Glu Thr Ala Asp Leu Leu Ala Glu Lys Ala Gln
375                 380                 385

ATC ACC GAG GAG GAG GCA AAA CTT CTG GCC CAG AAG GCC GCA GAG GCT              1434
Ile Thr Glu Glu Glu Ala Lys Leu Leu Ala Gln Lys Ala Ala Glu Ala
390                 395                 400                 405

GAG CAG GAA ATG CAG CGC ATC AAG GCC ACA GCG ATT CGC ACG GAG GAG              1482
Glu Gln Glu Met Gln Arg Ile Lys Ala Thr Ala Ile Arg Thr Glu Glu
                410                 415                 420

GAG AAG CGC CTG ATG GAG CAG AAG GTG CTG GAA GCC GAG GTG CTG GCA              1530
Glu Lys Arg Leu Met Glu Gln Lys Val Leu Glu Ala Glu Val Leu Ala
            425                 430                 435

CTG AAG ATG GCT GAG GAG TCA GAG AGG AGG GCC AAA GAG GCA GAT CAG              1578
Leu Lys Met Ala Glu Glu Ser Glu Arg Arg Ala Lys Glu Ala Asp Gln
        440                 445                 450

CTG AAG CAG GAC CTG CAG GAA GCA CGC GAG GCG GAG CGA AGA GCC AAG              1626
Leu Lys Gln Asp Leu Gln Glu Ala Arg Glu Ala Glu Arg Arg Ala Lys
455                 460                 465

CAG AAG CTC CTG GAG ATT GCC ACC AAG CCC ACG TAC CCG CCC ATG AAC              1674
Gln Lys Leu Leu Glu Ile Ala Thr Lys Pro Thr Tyr Pro Pro Met Asn
470                 475                 480                 485

CCA ATT CCA GCA CCG TTG CCT CCT GAC ATA CCA AGC TTC AAC CTC ATT              1722
Pro Ile Pro Ala Pro Leu Pro Pro Asp Ile Pro Ser Phe Asn Leu Ile
                490                 495                 500

GGT GAC AGC CTG TCT TTC GAC TTC AAA GAT ACT GAC ATG AAG CGG CTT              1770
Gly Asp Ser Leu Ser Phe Asp Phe Lys Asp Thr Asp Met Lys Arg Leu
            505                 510                 515

TCC ATG GAG ATA GAG AAA GAA AAA GTG GAA TAC ATG GAA AAG AGC AAG              1818
Ser Met Glu Ile Glu Lys Glu Lys Val Glu Tyr Met Glu Lys Ser Lys
        520                 525                 530

CAT CTG CAG GAG CAG CTC AAT GAA CTC AAG ACA GAA ATC GAG GCC TTG              1866
His Leu Gln Glu Gln Leu Asn Glu Leu Lys Thr Glu Ile Glu Ala Leu
535                 540                 545

AAA CTG AAA GAG AGG GAG ACA GCT CTG GAT ATT CTG CAC AAT GAG AAC              1914
Lys Leu Lys Glu Arg Glu Thr Ala Leu Asp Ile Leu His Asn Glu Asn
550                 555                 560                 565

TCC GAC AGG GGT GGC AGC AGC AAG CAC AAT ACC ATT AAA AAG CTC ACC              1962
Ser Asp Arg Gly Gly Ser Ser Lys His Asn Thr Ile Lys Lys Leu Thr
                570                 575                 580

TTG CAG AGC GCC AAG TCC CGA GTG GCC TTC TTT GAA GAG CTC                      2004
Leu Gln Ser Ala Lys Ser Arg Val Ala Phe Phe Glu Glu Leu
            585                 590                 595
```

```
TAGCAGGTGA CCCAGCCACC CCAGGACCTG CCACTTCTCC TGCTACCGGG ACCGCGGGAT      2064

GGACCAGATA TCAAGAGAGC CATCCATAGG GAGCTGGCTG GGGGTTTCCG TGGGAGCTCC      2124

AGAACTTTCC CCAGCTGAGT GAAGAGCCCA GCCCCTCTTA TGTGCAATTG CCTTGAACTA      2184

CGACCCTGTA GAGATTTCTC TCATGGCGTT CTAGTTCTCT GACCTGAGTC TTTGTTTTAA      2244

GAAGTATTTG TCT                                                        2257
```

(2) INFORMATION FOR SEQ ID NO:16:

(i) SEQUENCE CHARACTERISTICS:
        (A) LENGTH: 595 amino acids
        (B) TYPE: amino acid
        (D) TOPOLOGY: linear (ii) MOLECULE TYPE: protein (xi) SEQUENCE DESCRIPTION: SEQ ID NO:16:

```
Met Ala Gly Ala Ile Ala Ser Arg Met Ser Phe Ser Ser Leu Lys Arg
 1               5                  10                  15

Lys Gln Pro Lys Thr Phe Thr Val Arg Ile Val Thr Met Asp Ala Glu
            20                  25                  30

Met Glu Phe Asn Cys Glu Met Lys Trp Lys Gly Lys Asp Leu Phe Asp
        35                  40                  45

Leu Val Cys Arg Thr Leu Gly Leu Arg Glu Thr Trp Phe Phe Gly Leu
    50                  55                  60

Gln Tyr Thr Ile Lys Asp Thr Val Ala Trp Leu Lys Met Asp Lys Lys
65                  70                  75                  80

Val Leu Asp His Asp Val Ser Lys Glu Glu Pro Val Thr Phe His Phe
                85                  90                  95

Leu Ala Lys Phe Tyr Pro Glu Asn Ala Glu Glu Glu Leu Val Gln Glu
            100                 105                 110

Ile Thr Gln His Leu Phe Phe Leu Gln Val Lys Lys Gln Ile Leu Asp
        115                 120                 125

Glu Lys Ile Tyr Cys Pro Pro Glu Ala Ser Val Leu Leu Ala Ser Tyr
    130                 135                 140

Ala Val Gln Ala Lys Tyr Gly Asp Tyr Asp Pro Ser Val His Lys Arg
145                 150                 155                 160

Gly Phe Leu Ala Gln Glu Glu Leu Leu Pro Lys Arg Val Ile Asn Leu
                165                 170                 175

Tyr Gln Met Thr Pro Glu Met Trp Glu Glu Arg Ile Thr Ala Trp Tyr
            180                 185                 190

Ala Glu His Arg Gly Arg Ala Arg Asp Glu Ala Glu Met Glu Tyr Leu
        195                 200                 205

Lys Ile Ala Gln Asp Leu Glu Met Tyr Gly Val Asn Tyr Phe Ala Ile
    210                 215                 220

Arg Asn Lys Lys Gly Thr Glu Leu Leu Leu Gly Val Asp Ala Leu Gly
225                 230                 235                 240

Leu His Ile Tyr Asp Pro Glu Asn Arg Leu Thr Pro Lys Ile Ser Phe
                245                 250                 255

Pro Trp Asn Glu Ile Arg Asn Ile Ser Tyr Ser Asp Lys Glu Phe Thr
            260                 265                 270

Ile Lys Pro Leu Asp Lys Lys Ile Asp Val Phe Lys Phe Asn Ser Ser
        275                 280                 285

Lys Leu Arg Val Asn Lys Leu Ile Leu Gln Leu Cys Ile Gly Asn His
    290                 295                 300
```

```
Asp Leu Phe Met Arg Arg Arg Lys Ala Asp Ser Leu Glu Val Gln Gln
305                 310                 315                 320

Met Lys Ala Gln Ala Arg Glu Glu Lys Ala Arg Lys Gln Met Glu Arg
                325                 330                 335

Gln Arg Leu Ala Arg Glu Lys Gln Met Arg Glu Glu Ala Glu Arg Thr
                340                 345                 350

Arg Asp Glu Leu Glu Arg Leu Leu Gln Met Lys Glu Glu Ala Thr
        355                 360                 365

Met Ala Asn Glu Ala Leu Met Arg Ser Glu Glu Thr Ala Asp Leu Leu
370                 375                 380

Ala Glu Lys Ala Gln Ile Thr Glu Glu Ala Lys Leu Leu Ala Gln
385                 390                 395                 400

Lys Ala Ala Glu Ala Glu Gln Glu Met Gln Arg Ile Lys Ala Thr Ala
                405                 410                 415

Ile Arg Thr Glu Glu Glu Lys Arg Leu Met Glu Gln Lys Val Leu Glu
                420                 425                 430

Ala Glu Val Leu Ala Leu Lys Met Ala Glu Glu Ser Glu Arg Arg Ala
                435                 440                 445

Lys Glu Ala Asp Gln Leu Lys Gln Asp Leu Gln Glu Ala Arg Glu Ala
                450                 455                 460

Glu Arg Arg Ala Lys Gln Lys Leu Leu Glu Ile Ala Thr Lys Pro Thr
465                 470                 475                 480

Tyr Pro Pro Met Asn Pro Ile Pro Ala Pro Leu Pro Pro Asp Ile Pro
                485                 490                 495

Ser Phe Asn Leu Ile Gly Asp Ser Leu Ser Phe Asp Phe Lys Asp Thr
                500                 505                 510

Asp Met Lys Arg Leu Ser Met Glu Ile Glu Lys Glu Lys Val Glu Tyr
                515                 520                 525

Met Glu Lys Ser Lys His Leu Gln Glu Gln Leu Asn Glu Leu Lys Thr
                530                 535                 540

Glu Ile Glu Ala Leu Lys Leu Lys Glu Arg Glu Thr Ala Leu Asp Ile
545                 550                 555                 560

Leu His Asn Glu Asn Ser Asp Arg Gly Gly Ser Ser Lys His Asn Thr
                565                 570                 575

Ile Lys Lys Leu Thr Leu Gln Ser Ala Lys Ser Arg Val Ala Phe Phe
                580                 585                 590

Glu Glu Leu
        595

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:17:

CCATCTCACT TAGCTCCAAT G                                          21

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(xi) SEQUENCE DESCRIPTION: SEQ ID NO:18:

CTCACTCAGT CTCTGTCTAC                                              20

(2) INFORMATION FOR SEQ ID NO:19:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:19:

GTAACCGGCC                                                         10

(2) INFORMATION FOR SEQ ID NO:20:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:20:

GTTATTGCAG                                                         10

(2) INFORMATION FOR SEQ ID NO:21:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:21:

GTTGGGCTAG                                                         10

(2) INFORMATION FOR SEQ ID NO:22:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:22:

AATTCTGCAG                                                         10

(2) INFORMATION FOR SEQ ID NO:23:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:23:

GTACATCAGT                                                         10

(2) INFORMATION FOR SEQ ID NO:24:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:24:

```
CTCCTTTCAG                                                              10

(2) INFORMATION FOR SEQ ID NO:25:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:25:

GTAGGCTCAA                                                              10

(2) INFORMATION FOR SEQ ID NO:26:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:26:

TTCTTTCCAG                                                              10

(2) INFORMATION FOR SEQ ID NO:27:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:27:

GTAAGAGATT                                                              10

(2) INFORMATION FOR SEQ ID NO:28:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:28:

TTTTTGGTAG                                                              10

(2) INFORMATION FOR SEQ ID NO:29:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:29:

GTGAGGCCCA                                                              10

(2) INFORMATION FOR SEQ ID NO:30:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:30:
```

CTCCCCACAG                                                                10

(2) INFORMATION FOR SEQ ID NO:31:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:31:

GTGTGTTGAA                                                                10

(2) INFORMATION FOR SEQ ID NO:32:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:32:

GGATCCACAG                                                                10

(2) INFORMATION FOR SEQ ID NO:33:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:33:

GTAGGACATG                                                                10

(2) INFORMATION FOR SEQ ID NO:34:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:34:

ATTCTTCCAG                                                                10

(2) INFORMATION FOR SEQ ID NO:35:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:35:

GTAAGTTGAG                                                                10

(2) INFORMATION FOR SEQ ID NO:36:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:36:

GTGGCCACAG                                                                10

(2) INFORMATION FOR SEQ ID NO:37:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:37:

GTGAGCACAA        10

(2) INFORMATION FOR SEQ ID NO:38:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:38:

CCCCTCGCAG        10

(2) INFORMATION FOR SEQ ID NO:39:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:39:

GTGATTTCTG        10

(2) INFORMATION FOR SEQ ID NO:40:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:40:

TGCCCTCCAG        10

(2) INFORMATION FOR SEQ ID NO:41:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:41:

GTGAGGGGGC        10

(2) INFORMATION FOR SEQ ID NO:42:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:42:

TTCCTTGCAG        10

(2) INFORMATION FOR SEQ ID NO:43:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:43:

GTGAGCCTGG                                          10

(2) INFORMATION FOR SEQ ID NO:44:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:44:

TCATTAACAG                                          10

(2) INFORMATION FOR SEQ ID NO:45:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:45:

GTATGTAGCC                                          10

(2) INFORMATION FOR SEQ ID NO:46:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:46:

TTGCCGGCAG                                          10

(2) INFORMATION FOR SEQ ID NO:47:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:47:

GTACCCAGGG                                          10

(2) INFORMATION FOR SEQ ID NO:48:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:48:

GCTGGTTTAG                                          10

(2) INFORMATION FOR SEQ ID NO:49:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:49:

GTAGGTTGTT                                          10

(2) INFORMATION FOR SEQ ID NO:50:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:50:

TTTCTTACAG                                          10

(2) INFORMATION FOR SEQ ID NO:51:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:51:

GCTAAAGGGC TCAGAGTGCA G                        21

(2) INFORMATION FOR SEQ ID NO:52:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:52:

GAGAACCTCT CGAGCTTCCA C                        21

(2) INFORMATION FOR SEQ ID NO:53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:53:

TGTCCTTCCC CATTGGTTTG                          20

(2) INFORMATION FOR SEQ ID NO:54:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:54:

CAGTTTCATC GAGTTCTAGC C                        21

(2) INFORMATION FOR SEQ ID NO:55:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (xi) SEQUENCE DESCRIPTION: SEQ ID NO:55:

AGTGCAGAGA AAAGGTTTTA TTAATGAT                                           28

(2) INFORMATION FOR SEQ ID NO:56:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:56:

TGGAAAGCTC ACGTCAGCC                                                     19

(2) INFORMATION FOR SEQ ID NO:57:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:57:

GCTTCTTTGA GGGTAGCACA                                                    20

(2) INFORMATION FOR SEQ ID NO:58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:58:

GGTCAACTCT GAGGCCAACT                                                    20

(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:59:

CCTCACTTCC CCTCACAGAG                                                    20

(2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:60:

CCCATGACCC AAATTAACGC                                                    20

(2) INFORMATION FOR SEQ ID NO:61:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:61:

GCTCTCCCTT TCTTCTTTCC                                                    20

(2) INFORMATION FOR SEQ ID NO:62:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:62:

TCCTTCAAGT CCTTTGGTTA GC                                                 22

(2) INFORMATION FOR SEQ ID NO:63:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:63:

TGGCAGTTAT CTTTAGAATC TC                                                 22

(2) INFORMATION FOR SEQ ID NO:64:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:64:

TTAGACCACA TATCTGCTAT G                                                  21

(2) INFORMATION FOR SEQ ID NO:65:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:65:

CATGTGTAGG TTTTTTATTT TGC                                                23

(2) INFORMATION FOR SEQ ID NO:66:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:66:

GCCCATAAAG GAATGTAAAC C                                                  21

(2) INFORMATION FOR SEQ ID NO:67:

(i) SEQUENCE CHARACTERISTICS:

(A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:67:

CCATCTCACT TAGCTCCAAT G                                         21

(2) INFORMATION FOR SEQ ID NO:68:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:68:

CTCACTCAGT CTCTGTCTAC                                           20

(2) INFORMATION FOR SEQ ID NO:69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:69:

GAATGCTTGA TTTGGTGCCC                                           20

(2) INFORMATION FOR SEQ ID NO:70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:70:

GAGGTTTCAA CACACCCGGA                                           20

(2) INFORMATION FOR SEQ ID NO:71:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:71:

GAAGGTTGAA TAAAATTTTG AGCCTC                                    26

(2) INFORMATION FOR SEQ ID NO:72:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:72:

GACAGGGAAA GATCTGCTGG ACC                                       23

(2) INFORMATION FOR SEQ ID NO:73:

(i) SEQUENCE CHARACTERISTICS:
        (A) LENGTH: 21 base pairs (B) TYPE: nucleic acid
          (C) STRANDEDNESS: single
          (D) TOPOLOGY: linear (xi) SEQUENCE DESCRIPTION: SEQ ID NO:73:

CTGTTCTTAT TGGATCCACA G                                           21

(2) INFORMATION FOR SEQ ID NO:74:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:74:

AACAACCACA CCCTCAAAGC                                             20

(2) INFORMATION FOR SEQ ID NO:75:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (xi) SEQUENCE DESCRIPTION: SEQ ID NO:75:

GACTTGGTGC TCCTAATTCC C                                           21

(2) INFORMATION FOR SEQ ID NO:76:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (xi) SEQUENCE DESCRIPTION: SEQ ID NO:76:

CCATTATCAG TAATGAAAAC CAGG                                        24

(2) INFORMATION FOR SEQ ID NO:77:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:77:

TGCTACCTGC AAGAGCTCAA                                             20

(2) INFORMATION FOR SEQ ID NO:78:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (xi) SEQUENCE DESCRIPTION: SEQ ID NO:78:

CTGACCACAC AGTGACATC                                              19

(2) INFORMATION FOR SEQ ID NO:79:

(i) SEQUENCE CHARACTERISTICS:
          (A) LENGTH: 19 base pairs
          (B) TYPE: nucleic acid

```
        (C) STRANDEDNESS: single
        (D) TOPOLOGY: linear (xi) SEQUENCE DESCRIPTION: SEQ ID NO:79:

TCTTTGGCCC TTGTGGCAC                                                    19

(2) INFORMATION FOR SEQ ID NO:80:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:80:

CAGGAGACCA AGCTCCAGAA                                                   20

(2) INFORMATION FOR SEQ ID NO:81:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:81:

TTCAGCTAAG AGCACTGTGC                                                   20

(2) INFORMATION FOR SEQ ID NO:82:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:82:

CGCTGCATTT CCTGCTCAG                                                    19

(2) INFORMATION FOR SEQ ID NO:83:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:83:

GCTGAAAAGG CCCAGATCA                                                    19

(2) INFORMATION FOR SEQ ID NO:84:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:84:

CTTGAGGACA ACTGCTGTAG                                                   20

(2) INFORMATION FOR SEQ ID NO:85:

(i) SEQUENCE CHARACTERISTICS:
        (A) LENGTH: 20 base pairs
        (B) TYPE: nucleic acid
        (C) STRANDEDNESS: single
```

(D) TOPOLOGY: linear (xi) SEQUENCE DESCRIPTION: SEQ ID NO:85:

GGTGTCTTTT CCTGCTACCT                                               20

(2) INFORMATION FOR SEQ ID NO:86:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:86:

GGGAGGAAAG AGAACATCAC                                               20

(2) INFORMATION FOR SEQ ID NO:87:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:87:

TGTGCCATTG CCTCTGTG                                                 18

(2) INFORMATION FOR SEQ ID NO:88:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:88:

AGGGCACAGG GGGCTACA                                                 18

(2) INFORMATION FOR SEQ ID NO:89:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:89:

TGGCCAAGTA GAGACGTGA                                                19

(2) INFORMATION FOR SEQ ID NO:90:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:90:

TACAAGAAAG AGACCCTGGG                                               20

(2) INFORMATION FOR SEQ ID NO:91:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:91:

TCTGCCCAAG CCCTGATGC                                                        19

(2) INFORMATION FOR SEQ ID NO:92:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:92:

TGGTCCTGAT CAGCAAAATA C                                                     21

(2) INFORMATION FOR SEQ ID NO:93:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:93:

GGCATTGTTG ATATCACAGG G                                                     21

(2) INFORMATION FOR SEQ ID NO:94:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:94:

GGCAGCACCA TCACCACATA                                                       20

(2) INFORMATION FOR SEQ ID NO:95:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:95:

CTCTCAGCTT CTTCTCTGCT                                                       20

(2) INFORMATION FOR SEQ ID NO:96:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:96:

CCAGCCAGCT CCTATGGATG                                                       20

(2) INFORMATION FOR SEQ ID NO:97:

(i) SEQUENCE CHARACTERISTICS:
            (A) LENGTH: 21 base pairs
            (B) TYPE: nucleic acid
            (C) STRANDEDNESS: both
            (D) TOPOLOGY: both (xi) SEQUENCE DESCRIPTION: SEQ ID NO:97:

TACGGTGTGW ACTACTTTGC A                                      21

(2) INFORMATION FOR SEQ ID NO:98:

(i) SEQUENCE CHARACTERISTICS:
           (A) LENGTH: 21 base pairs
           (B) TYPE: nucleic acid
           (C) STRANDEDNESS: both
           (D) TOPOLOGY: both (ix) FEATURE:
           (A) NAME/KEY: CDS
           (B) LOCATION: 1..21

(xi) SEQUENCE DESCRIPTION: SEQ ID NO:98:

TAC GGT GTG AAC TAC TTT GCA                                  21
Tyr Gly Val Asn Tyr Phe Ala
  1               5

(2) INFORMATION FOR SEQ ID NO:99:

(i) SEQUENCE CHARACTERISTICS:
           (A) LENGTH: 7 amino acids
           (B) TYPE: amino acid
           (D) TOPOLOGY: linear (ii) MOLECULE TYPE: protein (xi) SEQUENCE DESCRIPTION: SEQ ID NO:99:

Tyr Gly Val Asn Tyr Phe Ala
  1               5

(2) INFORMATION FOR SEQ ID NO:100:

(i) SEQUENCE CHARACTERISTICS:
           (A) LENGTH: 15 base pairs
           (B) TYPE: nucleic acid
           (C) STRANDEDNESS: both
           (D) TOPOLOGY: both (xi) SEQUENCE DESCRIPTION: SEQ ID NO:100:

GGGAAGGACC TCTTT                                             15

(2) INFORMATION FOR SEQ ID NO:101:

(i) SEQUENCE CHARACTERISTICS:
           (A) LENGTH: 14 base pairs
           (B) TYPE: nucleic acid
           (C) STRANDEDNESS: both
           (D) TOPOLOGY: both (xi) SEQUENCE DESCRIPTION: SEQ ID NO:101:

CACATTTATG ACCC                                              14

(2) INFORMATION FOR SEQ ID NO:102:

(i) SEQUENCE CHARACTERISTICS:
           (A) LENGTH: 243 base pairs
           (B) TYPE: nucleic acid
           (C) STRANDEDNESS: both
           (D) TOPOLOGY: both (xi) SEQUENCE DESCRIPTION: SEQ ID NO:102:

AGTGCAGAGA AAAGGTTTTA TTAATGATTT TTGCTCACAG TGTCCTTCCC CATTGGTTTG    60

TTATTGCAGA TGAAGTGGAA AGGGAAGGAC CTCTTTGATT TGGTGTGCCG GACTCTGGGG   120

```
CTCCGAGAAA CCTGGTTCTT TGGACTGCAG TACACAATCA AGGACACAGT GGCCTGGCTC      180

AAAATGGACA AGAAGGTTGG GCTAGAACTC GATGAAACTG GTGGGGCTGA CGTGAGCTTT      240

CCA                                                                   243

(2) INFORMATION FOR SEQ ID NO:103:

(i) SEQUENCE CHARACTERISTICS:
        (A) LENGTH: 275 base pairs
        (B) TYPE: nucleic acid
        (C) STRANDEDNESS: both
        (D) TOPOLOGY: both (xi) SEQUENCE DESCRIPTION: SEQ ID NO:103:

GCTTCTTTGA GGGTAGCACA GGAGGAAGTG CCAATATANN GTGTGTTTGT CTTTTGCTCT       60

GCAATTCTGC AGGTACTGGA TCATGATGTT TCAAAGGAAG AACCAGTCAC CTTTCACTTC      120

TTGGCCAAAT TTTATCCTGA GAATGCTGAA GAGGAGCTGG TTCAGGAGAT CACACAACAT      180

TTATTCTTCT TACAGGTACA TCAGTCAAGG CTACCCCCCA GTTCTGAGAG AGAACTTGCC      240

CAGGAGTGGT TGCAGAGTTG GCCTCAGAGT TGACC                                275

(2) INFORMATION FOR SEQ ID NO:104:

(i) SEQUENCE CHARACTERISTICS:
        (A) LENGTH: 236 base pairs
        (B) TYPE: nucleic acid
        (C) STRANDEDNESS: both
        (D) TOPOLOGY: both (xi) SEQUENCE DESCRIPTION: SEQ ID NO:104:

GCTAAAGGGC TCAGAGTGCA GGCCGTGGGG CGCGAGGGTC CCGGGCCTGA GCCCCGCGCC       60

ATGGCCGGGG CCATCGCTTC CCGCATGAGC TTCAGCTCTC TCAAGAGGAA GCAACCCAAG      120

ACGTTCACCG TGAGGATCGT CACCATGGAC GCCGAGATGG AGTTCAATTG CGAGGTAACC      180

GGCCGGCAGC CCCGACTGCT GCGGTGACAG TCGAGGTGGA AGCTCGAGAG GTTCTC         236

(2) INFORMATION FOR SEQ ID NO:105:

(i) SEQUENCE CHARACTERISTICS:
        (A) LENGTH: 188 base pairs
        (B) TYPE: nucleic acid
        (C) STRANDEDNESS: both
        (D) TOPOLOGY: both (xi) SEQUENCE DESCRIPTION: SEQ ID NO:105:

CCTCACTTCC CCTCACAGAG TATCATGTCT CCCTTGTTGC TCCTTTCAGG TAAAGAAGCA       60

GATTTTAGAT GAAAAGATCT ACTGCCCTCC TGAGGCTTCT GTGCTCCTGG CTTCTTACGC      120

CGTCCAGGCC AAGGTAGGCT CAAAGAAGAA AAATGTATTT TTNNCTGGGC GTTAATTTGG      180

GTCATGGG                                                              188

(2) INFORMATION FOR SEQ ID NO:106:

(i) SEQUENCE CHARACTERISTICS:
        (A) LENGTH: 200 base pairs
        (B) TYPE: nucleic acid
        (C) STRANDEDNESS: both
        (D) TOPOLOGY: both (xi) SEQUENCE DESCRIPTION: SEQ ID NO:106:

TGGCAGTTAT CTTTAGAATC TCAATCGCCT GCTCTCCCTT TCTTCTTTCC AGTATGGTGA       60

CTACGACCCC AGTGTTCACA AGCGGGGATT TTTGGCCCAA GAGGAATTGC TTCCAAAAAG      120
```

```
GGTAAGAGAT TAAATTCCCT TTTCAGGAAG ACATAGCAGA TATGTGGTCT AAAAGAAAGC        180

TAACCAAAGG ACTTGAAGGA                                                    200

(2) INFORMATION FOR SEQ ID NO:107:

(i) SEQUENCE CHARACTERISTICS:
        (A) LENGTH: 256 base pairs
        (B) TYPE: nucleic acid
        (C) STRANDEDNESS: both
        (D) TOPOLOGY: both (xi) SEQUENCE DESCRIPTION: SEQ ID NO:107:

TCTGTGTGAC TACTCCTGGT GTAGCTTTAA AATAGCTTTA CTGTTTGTAA AATGATGCAT         60

AATTATAAAA GTGGCAAACA ATACCAAATT TACTTCATGT GTAGGTTTTT TATTTTGCTC        120

TATTTTTTGG TAGGTAATAA ATCTGTATCA GATGACTCCG GAAATGTGGG AGGAGAGAAT       180

TACTGCTTGG TACGCAGAGC ACCGAGGCCG AGCCAGGTGA GGCCCATTCA TTGTTGGTTT       240

ACATTCCTTT ATGGGC                                                       256

(2) INFORMATION FOR SEQ ID NO:108:

(i) SEQUENCE CHARACTERISTICS:
        (A) LENGTH: 240 base pairs
        (B) TYPE: nucleic acid
        (C) STRANDEDNESS: both
        (D) TOPOLOGY: both (xi) SEQUENCE DESCRIPTION: SEQ ID NO:108:

GAATGCTTGA TTTGGTGGCC CACCCGCTCT CCACCCATCT CACTTAGCTC CAATGACAGT        60

GTCTTCCGTT CTCCCCACAG GGATGAAGCT GAAATGGAAT ATCTGAAGAT AGCTCAGGAC       120

CTGGAGATGT ACGGTGTGAA CTACTTTGCA ATCCGGGTGT GTTGAAACCT CTCTGAGCTC       180

CTTGTGTAGT AGACAGAGAC TGAGTGAGGG CCAGGACTGC TAAAATGGTT ACTTCTTCAT       240

(2) INFORMATION FOR SEQ ID NO:109:

(i) SEQUENCE CHARACTERISTICS:
        (A) LENGTH: 387 base pairs
        (B) TYPE: nucleic acid
        (C) STRANDEDNESS: both
        (D) TOPOLOGY: both (xi) SEQUENCE DESCRIPTION: SEQ ID NO:109:

TCTGTGGACC TGCTGAACTG CACATGTGAC AGTGTGTGCC AGATTCTTTG GAAGGTTGAA        60

TAAAATTTTG AGCCTCAGCT GGCGCTTACA GTAGCTGTTC TTATTGGATC CACAGAATAA      120

AAAGGGCACA GAGCTGCTGC TTGGAGTGGA TGCCCTGGGG CTTCACATTT ATGACCCTGA      180

GAACAGACTG ACCCCCAAGA TCTCCTTCCC GTGAATGAA ATCCGAAACA TCTCGTACAG       240

TGACAAGGAG GTAGGACATG TGTGTACTGC AGATGGGTCC AGCAGATCTT TCCCTGTCTG      300

CCCCCCTCAC TGGAGCCTCC CCAGCCAGGG CATCTCCTTG TTATTCATAG AGTCCTTTAA      360

TTCCCAGGCT TTGAGGGTGT GGTTGTT                                           387

(2) INFORMATION FOR SEQ ID NO:110:

(i) SEQUENCE CHARACTERISTICS:
        (A) LENGTH: 300 base pairs
        (B) TYPE: nucleic acid
        (C) STRANDEDNESS: both
        (D) TOPOLOGY: both
```

(xi) SEQUENCE DESCRIPTION: SEQ ID NO:110:

```
GACTTGGTGC TCCTAATTCC CTGAGGTTTA GTGCCTGGAT ACTGGGAAGC CAGNACAAGG      60
GCATAACNTC ATGCTGGTCT GTGGCCAGTG TGGTTGCGCA TTTGTGGAAT TNCCAATTGC     120
TGGTAACATT CCAGGCTGTC GGACTGAAAC TGTGTTCTGC TTCATTCTTC CAGTTTACTA    180
TTAAACCACT GGATAAGAAA ATTGATGTCT TCAAGTTTAA CTCCTCAAAG CTTCGTGTTA    240
ATAAGCTGGT AAGTTGAGAT CCTGGTAAGT TGAGATCCTG GTTTTCATTA CTGATAATGG    300
```

(2) INFORMATION FOR SEQ ID NO:111:

(i) SEQUENCE CHARACTERISTICS:
    (A) LENGTH: 260 base pairs
    (B) TYPE: nucleic acid
    (C) STRANDEDNESS: both
    (D) TOPOLOGY: both (xi) SEQUENCE DESCRIPTION: SEQ ID NO:111:

```
TGCTACCTGC AAGAGCTCAA ACTGCTATGG CACTAGTGGG CCAGTAGGCA GTGAAGTAAA     60
TTTGTGGATA TTAACCTTTT TGTCTGCTTC TGTGGCCACA GATTCTCCAG CTATGTATCG    120
GGAACCATGA TCTATTTATG AGGAGAAGGA AAGCCGATTC TTTGGAAGTT CAGCAGATGA    180
AAGCCCAGGC CAGGGAGGAG AAGGCTAGAA AGCAGGTGAG CACAACCTTG TTTTAACTGA    240
TGATGTCACT GTGTGGTCAG                                                260
```

(2) INFORMATION FOR SEQ ID NO:112:

(i) SEQUENCE CHARACTERISTICS:
    (A) LENGTH: 292 base pairs
    (B) TYPE: nucleic acid
    (C) STRANDEDNESS: both
    (D) TOPOLOGY: both (xi) SEQUENCE DESCRIPTION: SEQ ID NO:112:

```
TCTTTGGCCC TTGTGGCACC CTAGGTCTCG AGCCCTGTGA TTCAATGACT GTTTTTCTTC     60
ACCCCTCGCA GATGGAGCGG CAGCGCCTCG CTCGAGAGAA GCAGATGAGG GAGGAGGCTG    120
AACGCACGAG GGATGAGTTG GAGAGGAGGC TGCTGCAGAT GAAAGAAGAA GCAACAATGG    180
CCAACGAAGC ACTGGTGATT TCTGAGGGGC TGGGGTTCCA GGAGGCTACT TGGGGACTTC    240
CTTGGCTTTT CTGGAGCTTG GTCTCCTGAA AACATGAGTT AGCAGCGTTT GC            292
```

(2) INFORMATION FOR SEQ ID NO:113:

(i) SEQUENCE CHARACTERISTICS:
    (A) LENGTH: 365 base pairs
    (B) TYPE: nucleic acid
    (C) STRANDEDNESS: both
    (D) TOPOLOGY: both (xi) SEQUENCE DESCRIPTION: SEQ ID NO:113:

```
CGGGAGAACA GCACATGATC CCACTTCAGC TAAGAGCACT GTGCCCTCCA GATGCGGTCT     60
GAGGAGACAG CTGACCTGTT GGCTGAAAAG GCCCAGATCA CCGAGGAGGA GGCAAAACTT    120
CTGGCCCAGA AGGCCGCAGA GGCTGAGCAG GAAATGCAGC GCATCAAGGC CACAGCGATT    180
CGCACGGAGG AGGAGAAGCG CCTGATGGAG CAGAAGGTGC TGGAAGCCGAG GTGCTGGCA    240
CTGAAGATGG CTGAGGAGTC AGAGAGGAGG TGAGGGGCA CCGGGCACCA GACTGGCGAG    300
GAGGCTGGCG AAGGGCCGCA GACCAGCCTG CCCTGAGGCT GAGCTCTACA GCAGTTGTCC    360
TCAAG                                                                365
```

(2) INFORMATION FOR SEQ ID NO:114:

(i) SEQUENCE CHARACTERISTICS:
(A) LENGTH: 227 base pairs
(B) TYPE: nucleic acid
(C) STRANDEDNESS: both
(D) TOPOLOGY: both (xi) SEQUENCE DESCRIPTION: SEQ ID NO:114:

```
GGTGTCTTTT CCTGCTACCT GCCCTCTTCT GTGAAGCTGA CATCTCATCC TTTCCTTGCA        60
GGGCCAAAGA GGCAGATCAG CTGAAGCAGG ACCTGCAGGA AGCACGCGAG GCGGAGCGAA       120
GAGCCAAGCA GAAGCTCCTG GAGATTGCCA CCAAGCCCAC GTACCCGGTG AGCCTGGGGG       180
CCACCAGCTG GGGCTGCCTT AGTCCTGGTG ATGTTCTCTT TCCTCCC                     227
```

(2) INFORMATION FOR SEQ ID NO:115:

(i) SEQUENCE CHARACTERISTICS:
(A) LENGTH: 281 base pairs
(B) TYPE: nucleic acid
(C) STRANDEDNESS: both
(D) TOPOLOGY: both (xi) SEQUENCE DESCRIPTION: SEQ ID NO:115:

```
TGTGCCATTG CCTCTGTGGC TGCTGGAGGA TCGGTTGTCA ACACAGTAGT GTCCTTCTGT        60
GCTTGTATGA CCCAAGCTCC TAATCCGAAA TTTCTCATTA ACAGCCCATG AACCCAATTC       120
CAGCACCGTT GCCTCCTGAC ATACCAAGCT TCAACCTCAT TGGTGACAGC CTGTCTTTCG       180
ACTTCAAAGA TACTGACATG AAGCGGCTTT CCATGGAGAT AGAGAAAGAA AAGTATGTAG       240
CCCCCTGTGC CCTGCTGTGG GCTTGCTGTG AACTAGACTG A                          281
```

(2) INFORMATION FOR SEQ ID NO:116:

(i) SEQUENCE CHARACTERISTICS:
(A) LENGTH: 335 base pairs
(B) TYPE: nucleic acid
(C) STRANDEDNESS: both
(D) TOPOLOGY: both (xi) SEQUENCE DESCRIPTION: SEQ ID NO:116:

```
TGGCCAAGTA GAGACGTGAN NCCAGCNTNA AACCCTAGAT CGCACACCAA GCAGCTTGTG        60
GGCCACAGAG CACCTGAGCC GTGTCTCACT GTCTGCCCAA GCCCTGATGC ATGATACCCT       120
CTTGCCGGCA GAGTGGAATA CATGGAAAAG AGCAAGCATC TGCAGGAGCA GCTCAATGAA       180
CTCAAGACAG AAATCGAGGC CTTGAAACTG AAAGAGAGGG AGACAGCTCT GGATATTCTG       240
CACAATGAGA ACTCCGACAG GGGTGGCAGC AGCAAGCACA ATACCATTAA AAAGGTACCC       300
AGGGTCTCTT TCTTGTATTT TGCTGATCAG GACCA                                 335
```

(2) INFORMATION FOR SEQ ID NO:117:

(i) SEQUENCE CHARACTERISTICS:
(A) LENGTH: 254 base pairs
(B) TYPE: nucleic acid
(C) STRANDEDNESS: both
(D) TOPOLOGY: both (xi) SEQUENCE DESCRIPTION: SEQ ID NO:117:

```
CAAACAAAAT CACTCATCAC GATNTCAGGC CTATCCAAGC ATTTTGCANA TGGCACTTAT        60
GGCATTGTTG ATATCACAGG GTATGTTTTT GTTTTTCTTC ATTTTATTTT GCTGGTTTAG       120
CCTCAAGCCC AAGGCAGAAG ACCTATCTGC ATTTGAGCCC TCAAAGTAGC TTGTTCCCAG       180
```

```
GTACTCTCTA TGTGGTGATG GTGCTGCCCT CTGTGATACT AACCCGTGCA TGAGNTTGCC        240

TGTCTCTGTC TCGG                                                         254

(2) INFORMATION FOR SEQ ID NO:118:

(i) SEQUENCE CHARACTERISTICS:
        (A) LENGTH: 339 base pairs
        (B) TYPE: nucleic acid
        (C) STRANDEDNESS: both
        (D) TOPOLOGY: both (xi) SEQUENCE DESCRIPTION: SEQ ID NO:118:

AGGACCCTGT GAGACAGAGC GGAGGTCNNG TGCCCTCTCA GCTTCTTCTC TGCTTTCTTA         60

CAGCTCACCT TGCAGAGCGC CAAGTCCCGA GTGGCCTTCT TTGAAGAGCT CTAGCAGGTG        120

ACCCAGCCAC CCCAGGACCT GCCACTTCTC CTGCTACCGG GACCGCGGGA TGGACCAGAT        180

ATCAAGAGAG CCATCCATAG GGAGCTGGCT GGGGGTTTCC GTGGGAGCTC CAGAACTTTC        240

CCCAGCTGAG TGAAGAGCCC AGCCCCTCTT ATGTGCAATT GCCTTGAACT ACGACCCTGT        300

AGAGATTTCT CTCATGGCGT TCTAGTTCTC TGACCTGAG                              339

(2) INFORMATION FOR SEQ ID NO:119:

(i) SEQUENCE CHARACTERISTICS:
        (A) LENGTH: 14 base pairs
        (B) TYPE: nucleic acid
        (C) STRANDEDNESS: both
        (D) TOPOLOGY: both (xi) SEQUENCE DESCRIPTION: SEQ ID NO:119:

GGGAAGGCCT CTTT                                                          14

(2) INFORMATION FOR SEQ ID NO:120:

(i) SEQUENCE CHARACTERISTICS:
        (A) LENGTH: 10 base pairs
        (B) TYPE: nucleic acid
        (C) STRANDEDNESS: both
        (D) TOPOLOGY: both (xi) SEQUENCE DESCRIPTION: SEQ ID NO:120:

CACATGACCC                                                               10
```